(12) United States Patent
Sentmanat

(10) Patent No.: US 8,552,608 B2
(45) Date of Patent: *Oct. 8, 2013

(54) MODULAR MAGNETO MECHANICAL DEVICE

(75) Inventor: Martin Sentmanat, Spicewood, TX (US)

(73) Assignee: Smartin Technologies LLC, Spicewood, TX (US)

( * ) Notice: Subject to any disclaimer, the term of this patent is extended or adjusted under 35 U.S.C. 154(b) by 908 days.

This patent is subject to a terminal disclaimer.

(21) Appl. No.: 12/439,666

(22) PCT Filed: Aug. 31, 2007

(86) PCT No.: PCT/US2007/019291
§ 371 (c)(1),
(2), (4) Date: Nov. 10, 2009

(87) PCT Pub. No.: WO2008/027597
PCT Pub. Date: Mar. 6, 2008

(65) Prior Publication Data
US 2010/0152524 A1    Jun. 17, 2010

Related U.S. Application Data

(60) Provisional application No. 60/824,182, filed on Aug. 31, 2006.

(51) Int. Cl.
*H02K 1/27* (2006.01)
*A61M 1/12* (2006.01)

(52) U.S. Cl.
USPC ............... 310/156.11; 310/156.28; 600/16; 600/17

(58) Field of Classification Search
USPC ............ 310/156.01, 156.11, 156.12, 156.13, 310/156.14, 156.28, 156.29; 600/16–17
See application file for complete search history.

(56) References Cited

U.S. PATENT DOCUMENTS

| | | |
|---|---|---|
| 2,401,386 A | 6/1946 | Smellie |
| 5,507,629 A | 4/1996 | Jarvik |
| 6,100,618 A | 8/2000 | Schoeb et al. |
| 6,129,704 A | 10/2000 | Forman et al. |
| 6,244,835 B1 | 6/2001 | Antaki et al. |
| 6,280,157 B1 | 8/2001 | Cooper |

(Continued)

FOREIGN PATENT DOCUMENTS

| | | |
|---|---|---|
| JP | 11-123239 | 5/1999 |
| JP | 2000 060041 A | 2/2000 |

(Continued)

OTHER PUBLICATIONS

International Search report for PCT application PCT/US2007/019291, search report dated Jul. 18, 2008, 6 pages (2008).

*Primary Examiner* — Tran Nguyen
*Assistant Examiner* — Leda Pham
(74) *Attorney, Agent, or Firm* — Judy M. Mohr; Jacqueline F. Mahoney; McDermott Will & Emery LLP

(57) ABSTRACT

An electromechanical device has a rotor, a stator, and a module that at least partially houses the rotor. During normal operation of the electromechanical device, the stator is positioned external to and separate from the module.

18 Claims, 50 Drawing Sheets

(56) References Cited

U.S. PATENT DOCUMENTS

| | | |
|---|---|---|
| 6,293,901 B1 | 9/2001 | Prem |
| 6,447,265 B1 | 9/2002 | Antaki et al. |
| 6,447,266 B2 | 9/2002 | Antaki et al. |
| 6,447,270 B1 | 9/2002 | Schmidt et al. |
| 6,527,699 B1 | 3/2003 | Goldowsky |
| 6,547,539 B2 | 4/2003 | Izraelev |
| 6,579,315 B1 | 6/2003 | Weiss |
| 6,736,593 B2 | 5/2004 | Namiki et al. |
| 6,742,718 B2 | 6/2004 | Doebler et al. |
| 6,751,954 B2 | 6/2004 | Bridger et al. |
| 6,765,319 B1 | 7/2004 | Thompson |
| 6,784,580 B2 | 8/2004 | Yashiro et al. |
| 6,784,634 B2 | 8/2004 | Swea |
| 6,800,251 B2 | 10/2004 | Catterall et al. |
| 6,808,482 B1 | 10/2004 | Pacella et al. |
| 6,815,855 B2 | 11/2004 | Yashiro et al. |
| 6,832,888 B2 | 12/2004 | Kabasawa et al. |
| 6,847,182 B2 | 1/2005 | Ricotti |
| 6,866,881 B2 | 3/2005 | Prentice et al. |
| 6,892,534 B2 | 5/2005 | Silva et al. |
| 6,902,378 B2 | 6/2005 | Gaudet et al. |
| 6,911,757 B2 | 6/2005 | Lopatinsky et al. |
| 6,913,166 B2 | 7/2005 | Cline et al. |
| 7,638,915 B2 * | 12/2009 | Sentmanat ............ 310/156.11 |
| 7,661,932 B2 * | 2/2010 | El-Sayed et al. ............ 417/64 |
| 2001/0009645 A1 * | 7/2001 | Noda ............................ 417/355 |
| 2003/0187321 A1 * | 10/2003 | Hoffmann et al. ............. 600/16 |
| 2004/0027020 A1 * | 2/2004 | Newcomb ............ 310/156.01 |
| 2006/0058873 A1 | 3/2006 | Peralta |
| 2006/0122345 A1 | 6/2006 | Schulte et al. |
| 2006/0122456 A1 | 6/2006 | LaRose et al. |
| 2006/0241335 A1 * | 10/2006 | Benkowski et al. ............ 600/16 |

FOREIGN PATENT DOCUMENTS

| | | |
|---|---|---|
| JP | 2000-510929 A | 8/2000 |
| JP | 2004-346930 | 9/2004 |
| WO | WO 97/42414 A1 | 11/1997 |

* cited by examiner

MODULAR MAGNETO MECHANICAL DEVICE

This application is the National Stage of International Application No. PCT/US2007/019291, filed Aug. 31, 2007, which claims the benefit under 35 U.S.C. §119(e) of U.S. Provisional Application 60/824,183, filed Aug. 31, 2006, all of which are hereby incorporated by reference.

TECHNICAL FIELD

The present invention relates the art of methods and apparatuses regarding electromechanical devices, and more particularly to methods and apparatuses regarding brushless electric motors and electromotive devices.

BACKGROUND ART

It is known to have a conventional brushless motor 600 (as shown in FIG. 49) that includes a rotor 610 and a stator 630. Conventionally, the rotor 610 is positioned within the stator 630 and has a core 612 that allows the rotor 610 to rotate relative to the stator 630. The stator 630 has at least one magnetic source. Typically, the stator 630 has a plurality of magnetic sources, for example, three electromagnets 632, 633, and 634. Commonly, permanent magnets 614 are attached to the core 612 of the rotor 610 and the rotor 610 is coupled to a shaft (not shown). Typically, the shaft is mounted on a set of bearings (not shown) that allows for the rotation of the shaft. During the operation of the conventional brushless motor 600, a control assembly 602 controls the passing of current through the electromagnets 632, 633, and 634 to generate an electromagnetic field. The electromagnetic field interacts with the permanent magnets attached to the core of the rotor. The interaction between the permanent magnets and the electromagnetic field results in the rotation of the rotor relative to the stator. By alternating or otherwise controlling the polarity of the electromagnetic field generated by the current passing through the windings, the rotation of the rotor can be controlled. The rotor being coupled to the shaft, therefore allows the electric current being passed through the windings to be converted into the mechanical rotation of the shaft as a result of the interaction between the permanent magnets of the rotor and the electric field generated by the windings. Commonly, the shaft then provides a physical transfer of the mechanical energy to some other device or mechanism that may be coupled to the shaft. Conventionally, the rotor and the stator are positioned within a common motor casing 602.

It is known to control the rotation of the rotor by controlling the polarity of the electromagnets positioned within the stator. Referring to FIG. 49, typically, in a stator 630 that has three electromagnets 632, 633, and 634, the control assembly will control the direction of the current through the three electromagnets 632, 633, and 634 such that the first and second electromagnets 632, 633 will have polarities that are opposite with respect to each other, while the third electromagnet 634 will not generate any magnetic field. The permanent magnet 614 is then attracted towards one electromagnet and repulsed from the other thereby causing the rotor 610 to rotate. The control assembly may determine the position of the permanent magnet 614 by sensing a current being induced in the third electromagnet 634 by the motion of the permanent magnet 614. The controller then controls the current passing through the electromagnets 632, 633, and 634 to continue the rotation of the rotor 610.

Although known brushless motors work well for their intended purpose, several disadvantages exist. Often the wires extending from an external power source into the stator require the use of some type of seal, such as a dynamic mechanical seal, to prevent fluids from entering into and damaging the stator and its components and to prevent foreign particles from the stator from exiting into the system in which the brushless motor is immersed. Historically, most implantable electrical devices have been powered by either an implantable onboard battery or by an external hardwire power connection passing through a dermic seal into the body. In either case, the need for battery replacement or the likelihood of contracted infections has prevented such devices from being implanted on a permanent or semi-permanent basis within the human body.

Heart disease and other circulatory related ailments are disorders that plague hundreds of millions of people worldwide and claim the lives of millions more on an annual basis. Despite the extensive amount of literature pertaining to the field of artificial heart technology, many prior art devices take a primitive, yet conventional, approach with regard to the pumping of blood in biological circulatory systems. The prior art devices utilize a single centralized pumping means to circulate blood throughout a body in a manner similar to the operational utility of a natural human heart. Hence, while the existing paradigm to approaching these biomedical enigmas has been to ask the question "how to develop an artificial alternative to the human heart?" the more fundamental question to be asked is "how to develop a better circulatory system for the human body?" Although the heart may have developed in mammals and animals throughout nature as a single centralized circulatory pumping means, with regard to fundamental engineering principles concerning flow and transport phenomena the implementation of a single pumping means for conveying fluid media over a vast and complex flow network would be considered an inadequate engineering design by modern-day standards and practices. This is due to the fact that while in theory a single centralized pumping means would be sufficient to operate the flow network, in reality the presence of any subsequent flow restriction or blockage in the network would adversely affect the downstream flow thereby jeopardizing the vital operation of the entire flow network and causing an undue burden on the centralized pumping means. The application of staged pumping is a concept familiar to fluid, chemical, petrochemical, mechanical and industrial engineers that employs the use of multiple pumping means networked in series and/or in parallel in order to convey fluid media in large volumes over expansive fluid networks that may experience significant restrictions to flow and/or may be susceptible to clogging or blockage throughout the flow network.

DISCLOSURE OF THE INVENTION

There is provided a device has an electromechanical device having a rotor, a stator, a module that at least partially houses the rotor, and during normal operation of the brushless electromechanical device, the stator is positioned external to and separate from the module.

There is provided a device has an electromechanical device having a rotor, a stator, a module that at least partially houses the rotor, and during normal operation of the electromechanical device, the stator is positioned external to and separate from the module. The electromechanical device may be a brushless electric motor and may further include the rotor having a first magnet, the stator having a second magnet, and, a control assembly for use in controlling the motion of the rotor by controlling the polarity of the second magnet. The rotor may have a first permanent magnet and the stator may have a first electromagnet. Alternatively, the rotor may have a first electromagnet. The control assembly may control the orientation of the second magnet with respect to the first magnet. The module may have a first conduit for use in permitting a transportable media to pass through the module and to contact the rotor. The motion of the rotor may at least partially assist in the passage of the transportable media through the first conduit. In one embodiment, the module may have an adjustable aperture for use in controlling the flow of the transportable media through the first conduit. The motion of the rotor may at least partially control the opening and closing of the adjustable aperture.

There is provided a device has an electromechanical device having a rotor, a stator, a module that at least partially houses the rotor, and during normal operation of the electromechanical device, the stator is positioned external to and separate from the module. The electromechanical device may be a brushless electric motor and may further include the rotor having a first magnet, the stator having a second magnet, and, a control assembly for use in controlling the motion of the rotor by controlling the polarity of the second magnet. The module may have a first conduit for use in permitting a transportable media to pass through the module and to contact the rotor. The rotor may also have a spindle having a magnet receiving portion that at least partially receives the first magnet; a shaft about which the rotor rotates with respect to the module; and, a second conduit for use in permitting the transportable media to pass through the module and to contact the rotor, wherein the second conduit and the first conduit define a coaxial portal.

There is provided a device has an electromechanical device having a rotor, a stator, a module that at least partially houses the rotor, and during normal operation of the electromechanical device, the stator is positioned external to and separate from the module. The electromechanical device may be a brushless electric motor and may further include the rotor having a first magnet, the stator having a second magnet, and, a control assembly for use in controlling the motion of the rotor by controlling the polarity of the second magnet. The rotor may also have a spindle having a magnet receiving portion that at least partially receives the first magnet and a shaft about which the rotor rotates with respect to the module. The spindle may have a topographical feature formed on an outer surface of the spindle for use in contacting a transportable media. In another embodiment, the spindle may also have an independently movable element, wherein the orientation of the independently movable element with respect to the spindle is at least partially controlled by the motion of the spindle.

There is provided a device has an electromechanical device having a rotor, a stator, a module that at least partially houses the rotor, and during normal operation of the electromechanical device, the stator is positioned external to and separate from the module. The electromechanical device may be a brushless electric motor and may further include the rotor having a first magnet, the stator having a second magnet, and, a control assembly for use in controlling the motion of the rotor by controlling the polarity of the second magnet. The device may also have a conductive coil and the motion of the rotor may induce an electric current in the conductive coil.

There is provided a device has an electromechanical device having a rotor, a stator, a module that at least partially houses the rotor, and during normal operation of the electromechanical device, the stator is positioned external to and separate from the module. The electromechanical device may be a brushless electric motor and may further include the rotor having a first magnet, the stator having a second magnet, and, a control assembly for use in controlling the motion of the rotor by controlling the polarity of the second magnet. The rotor may be rotatably and linearly displaceable.

There is provided a device has an electromechanical device having a rotor, a stator, a module that at least partially houses the rotor, and during normal operation of the electromechanical device, the stator is positioned external to and separate from the module. The electromechanical device may be a brushless electric motor and may further include the rotor having a first magnet, the stator having a second magnet, and, a control assembly for use in controlling the motion of the rotor by controlling the polarity of the second magnet. The module may hermetically seal the first magnet.

There is provided a device has an electromechanical device having a rotor, a stator, a module that at least partially houses the rotor, and during normal operation of the electromechanical device, the stator is positioned external to and separate from the module. The electromechanical device may be a brushless electric motor and may further include the rotor having a first magnet, the stator having a second magnet, and, a control assembly for use in controlling the motion of the rotor by controlling the polarity of the second magnet. The device may also have a magnet assembly and the motion of the magnet assembly may at least partially be controlled by the motion of the rotor.

There is provided a device has an electromechanical device having a rotor, a stator, a module that at least partially houses the rotor, and during normal operation of the electromechanical device, the stator is positioned external to and separate from the module. The electromechanical device may be an electromotive device. The electromotive device may have a rotor having a first magnet and a stator having a first electromagnetic induction coil. During the normal operation of the electromotive device, the motion of the rotor may induce a current in the first electromagnetic induction coil. The first magnet of the rotor may be a first permanent magnet. The module may have a first conduit for use in permitting a transportable media to pass through the module and to contact the rotor. The motion of the rotor may at least partially assist in the passage of the transportable media through the first conduit. In one embodiment, the module may have an adjustable aperture for use in controlling the flow of the transportable media through the first conduit. The motion of the rotor may, in one embodiment, at least partially control the opening and closing of the adjustable aperture.

There is provided a device has an electromechanical device having a rotor, a stator, a module that at least partially houses the rotor, and during normal operation of the electromechanical device, the stator is positioned external to and separate from the module. The electromechanical device may be an electromotive device. The electromotive device may have a rotor having a first magnet and a stator having a first electromagnetic induction coil. During the normal operation of the electromotive device, the motion of the rotor may induce a current in the first electromagnetic induction coil. The module may have a first conduit for use in permitting a transportable media to pass through the module and to contact the rotor. The rotor may have a spindle. The spindle may have a magnetic receiving portion that at least partially receives the first magnet; a shaft about which the rotor rotates with respect to the module; and, a second conduit for use in permitting the transportable media to pass through the module and to contact the rotor. The first and second conduit may define a coaxial portal.

There is provided a device has an electromechanical device having a rotor, a stator, a module that at least partially houses the rotor, and during normal operation of the electromechanical device, the stator is positioned external to and separate from the module. The electromechanical device may be an electromotive device. The electromotive device may have a rotor having a first magnet and a stator having a first electromagnetic induction coil. During the normal operation of the electromotive device, the motion of the rotor may induce a current in the first electromagnetic induction coil. The rotor may have a spindle having a magnet receiving portion that at least partially receives the first magnet and a shaft about which the rotor may rotate with respect to the module. The spindle may also have a topographical feature that may be formed on the outer surface of the spindle for use in contacting a transportable media. The spindle may also have an independently movable element. The orientation of the movable element with respect to the spindle may be at least partially controlled by the motion of the spindle.

There is provided a device has an electromechanical device having a rotor, a stator, a module that at least partially houses the rotor, and during normal operation of the electromechanical device, the stator is positioned external to and separate from the module. The electromechanical device may be an electromotive device. The electromotive device may have a rotor having a first magnet and a stator having a first electromagnetic induction coil. During the normal operation of the electromotive device, the motion of the rotor may induce a current in the first electromagnetic induction coil. The rotor may be rotatable and linearly displaceable.

There is provided a device has an electromechanical device having a rotor, a stator, a module that at least partially houses the rotor, and during normal operation of the electromechanical device, the stator is positioned external to and separate from the module. The electromechanical device may be an electromotive device. The electromotive device may have a rotor having a first magnet and a stator having a first electromagnetic induction coil. During the normal operation of the electromotive device, the motion of the rotor may induce a current in the first electromagnetic induction coil. The module may hermetically seal the first magnet.

There is provided a device has an electromechanical device having a rotor, a stator, a module that at least partially houses the rotor, and during normal operation of the electromechanical device, the stator is positioned external to and separate from the module. The electromechanical device may be an electromotive device. The electromotive device may have a rotor having a first magnet and a stator having a first electromagnetic induction coil. During the normal operation of the electromotive device, the motion of the rotor may induce a current in the first electromagnetic induction coil. The device may also have a magnet assembly. The motion of the magnet assembly may be at least partially controlled by the motion of the rotor.

There is provided a device has an electromechanical device having a rotor and a stator. During the normal operation of the electromechanical device, the rotor and the stator are not positioned within a common motor casing.

There is provided a device has an electromechanical device having a rotor and a stator. During the normal operation of the electromechanical device, the rotor and the stator are not positioned within a common motor casing. The electromechanical device may be a brushless electric motor. The brushless electric motor may further have the rotor having a first magnet, the stator having a second magnet, and a control assembly for use in controlling the motion of the rotor by controlling the polarity of the second magnet.

There is provided a device has an electromechanical device having a rotor and a stator. During the normal operation of the electromechanical device, the rotor and the stator are not positioned within a common motor casing. The electromechanical device may be a brushless electric motor. The brushless electric motor may further have the rotor having a first magnet, the stator having a second magnet, and a control assembly for use in controlling the motion of the rotor by controlling the polarity of the second magnet. The rotor may have a first permanent magnet and the stator may have a first electromagnet. Alternately, the rotor may have an electromagnet. The control assembly may control the orientation of the second magnet with respect to the first magnet.

There is provided a device has an electromechanical device having a rotor and a stator. During the normal operation of the electromechanical device, the rotor and the stator are not positioned within a common motor casing. The electromechanical device may be a brushless electric motor. The brushless electric motor may further have the rotor having a first magnet, the stator having a second magnet, and a control assembly for use in controlling the motion of the rotor by controlling the polarity of the second magnet. The rotor may have a spindle having a magnet receiving portion that at last partially receives the first magnet and a shaft about which the rotor rotates with respect to the module. The spindle may also have a topographical feature formed on an outer surface of the spindle for use in contacting a transportable media.

There is provided a device has an electromechanical device having a rotor and a stator. During the normal operation of the electromechanical device, the rotor and the stator are not positioned within a common motor casing. The electromechanical device may be a brushless electric motor. The brushless electric motor may further have the rotor having a first magnet, the stator having a second magnet, and a control assembly for use in controlling the motion of the rotor by controlling the polarity of the second magnet. The device may also have a conductive coil and the motion of the rotor may induce an electric current in the conductive coil.

There is provided a device has an electromechanical device having a rotor and a stator. During the normal operation of the electromechanical device, the rotor and the stator are not positioned within a common motor casing. The electromechanical device may be a brushless electric motor. The brushless electric motor may further have the rotor having a first magnet, the stator having a second magnet, and a control assembly for use in controlling the motion of the rotor by controlling the polarity of the second magnet. The rotor may be rotatable and linearly displaceable.

There is provided a device has an electromechanical device having a rotor and a stator. During the normal operation of the electromechanical device, the rotor and the stator are not positioned within a common motor casing. The electromechanical device may be a brushless electric motor. The brushless electric motor may further have the rotor having a first magnet, the stator having a second magnet, and a control assembly for use in controlling the motion of the rotor by controlling the polarity of the second magnet. The device may also have a magnet assembly and the motion of the magnet assembly may be at least partially controlled by the motion of the rotor.

There is provided a device has an electromechanical device having a rotor and a stator. During the normal operation of the electromechanical device, the rotor and the stator are not positioned within a common motor casing. The electromechanical device may be an electromotive device. The electromotive device may have the rotor having a first magnet and the stator having a first electromagnetic induction coil. During the normal operation of the electromechanical device, the motion of the rotor may induce a current in the first electromagnetic induction coil.

There is provided a device has an electromechanical device having a rotor and a stator. During the normal operation of the electromechanical device, the rotor and the stator are not positioned within a common motor casing. The electromechanical device may be an electromotive device. The electromotive device may have the rotor having a first magnet and the stator having a first electromagnetic induction coil. During the normal operation of the electromechanical device, the motion of the rotor may induce a current in the first electromagnetic induction coil. The rotor may have a first permanent magnet.

There is provided a device has an electromechanical device having a rotor and a stator. During normal operation of the electromechanical device, the rotor is physically separated by a nongaseous barrier.

There is provided a device has an electromechanical device having a rotor and a stator. During normal operation of the electromechanical device, the rotor is physically separated by a nongaseous barrier. The electromechanical device may be a brushless electric motor. The brushless electric motor may have the rotor having a first magnet, the stator having a second magnet, and a control assembly for use in controlling the motion of the rotor by controlling the polarity of the second magnet.

There is provided a device has an electromechanical device having a rotor and a stator. During normal operation of the electromechanical device, the rotor is physically separated by a nongaseous barrier. The electromechanical device may be a brushless electric motor. The brushless electric motor may have the rotor having a first magnet, the stator having a second magnet, and a control assembly for use in controlling the motion of the rotor by controlling the polarity of the second magnet. The rotor may have a first permanent magnet and the stator may have a first electromagnet. Alternately, the rotor may have a first electromagnet.

There is provided a device has an electromechanical device having a rotor and a stator. During normal operation of the electromechanical device, the rotor is physically separated by a nongaseous barrier. The electromechanical device may be a brushless electric motor. The brushless electric motor may have the rotor having a first magnet, the stator having a second magnet, and a control assembly for use in controlling the motion of the rotor by controlling the polarity of the second magnet. The control assembly may control the orientation of the second magnet with respect to the first magnet.

There is provided a device has an electromechanical device having a rotor and a stator. During normal operation of the electromechanical device, the rotor is physically separated by a nongaseous barrier. The electromechanical device may be a brushless electric motor. The brushless electric motor may have the rotor having a first magnet, the stator having a second magnet, and a control assembly for use in controlling the motion of the rotor by controlling the polarity of the second magnet. The rotor may also have a spindle having a magnet receiving portion that at least partially receives the first magnet and a shaft about which the rotor rotates with respect to the module.

There is provided a device has an electromechanical device having a rotor and a stator. During normal operation of the electromechanical device, the rotor is physically separated by a nongaseous barrier. The electromechanical device may be a brushless electric motor. The brushless electric motor may have the rotor having a first magnet, the stator having a second magnet, and a control assembly for use in controlling the motion of the rotor by controlling the polarity of the second magnet. The nongaseous barrier may be a solid, a liquid, or a genetic substance.

There is provided a device has an electromechanical device having a rotor and a stator. During normal operation of the electromechanical device, the rotor is physically separated by a nongaseous barrier. The electromechanical device may be an electromotive device. The electromotive device may have the rotor having a first magnet and the stator having a first electromagnetic induction coil. During the normal operation of the electromechanical device, the motion of the rotor may induce a current in the first electromagnetic induction coil.

There is provided a device has an electromechanical device having a rotor and a stator. During normal operation of the electromechanical device, the rotor is physically separated by a nongaseous barrier. The electromechanical device may be an electromotive device. The electromotive device may have the rotor having a first magnet and the stator having a first electromagnetic induction coil. During the normal operation of the electromechanical device, the motion of the rotor may induce a current in the first electromagnetic induction coil. The rotor may have a first permanent magnet.

There is provided a device has an electromechanical device having a rotor and a stator. During normal operation of the electromechanical device, the rotor is physically separated by a nongaseous barrier. The electromechanical device may be an electromotive device. The electromotive device may have the rotor having a first magnet and the stator having a first electromagnetic induction coil. During the normal operation of the electromechanical device, the motion of the rotor may induce a current in the first electromagnetic induction coil. The rotor may also have a spindle having a magnet receiving portion that at least partially receives the first magnet and a shaft about which the rotor rotates with respect to the module.

There is provided a device has an electromechanical device having a rotor and a stator. During normal operation of the electromechanical device, the rotor is physically separated by a nongaseous barrier. The electromechanical device may be an electromotive device. The electromotive device may have the rotor having a first magnet and the stator having a first electromagnetic induction coil. During the normal operation of the electromechanical device, the motion of the rotor may induce a current in the first electromagnetic induction coil. The nongaseous barrier may be a solid, a liquid, or a genetic substance.

There is provided a device has an electromechanical device having a rotor, a stator, a module that at least partially houses the rotor, and during normal operation of the brushless electromechanical device, the stator is positioned external to and separate from the module. The device may also have a second electromechanical device that has a second rotor, a second stator, and a second module. During the normal operation of the second electromechanical device, the second stator is positioned external to and separate from the second module. The first electromechanical device may be functionally integrated with the second electromechanical device. The first electromechanical device may be functionally integrated with the second electromechanical device in parallel or in series.

The fundamental principles governing the operation of a modular magneto-mechanical device (hereinafter "3MD") are similar to those governing brushless motor technology. However, what distinguishes 3MD technology from a conventional brushless motor is that the source of the magnetic field controlling motion is not physically integrated within the common motor casing, but is situated external and independent to the mechanical/movable portion of the 3MD module. Unlike other functional automated mechanical devices that are coupled to a separate mechanical or electromechanical driving means (such as a drive motor, transmission or the like), with a 3MD module the functional automated mechanical device and driving means can be one in the same and hence a separate drive motor and coupling is not inherently required for its operation. Alternatively, a 3MD module may also serve as an independent driving means for controlling the motion of a separate functional mechanical device. In this manner, the mechanical/movable portion of a 3MD module can be immersed within any fluid, non-fluid, hazardous, potentially hazardous, or not-readily accessible environment regardless of temperature and/or pressure and driven by a control field completely external or hermetically sealed from said environment, thus obviating the need for dynamic mechanical seals otherwise required to protect any internal/control components (electrical or otherwise) of the driving means. Furthermore, because of its inherent design, the mechanical portion of the 3MD module can be made to be a replaceable and/or a disposable component, a particularly useful feature for 3MD applications involving hazardous or potentially hazardous media.

Disclosed herein is a new class of modular device that contains one or more magnetically charged or magnetically responsive movable elements whose motions can be controlled by an independent externally generated electromagnetic field or similar electrically charged flux source. Motion of the magnetic field defined by said magnetically charged movable elements can also be used to induce an electrical current in adjacent conductive elements. The prescribed kinematics of the movable element(s) may be of any conceivable motion that may include but is not limited to steady, stepped, ramped, oscillating, periodic and/or aperiodic rotation, linear actuation, one-, two-, or three-dimensional convolutions, or any conceivable combination of motions associated therewith. The devices may be used, controlled, and tasked singly, in tandem, or in multiple combinations to comprise a single or multi-function workflow. Each device may be coordinated or tasked independently to perform a single or multitude of conceivable functions that may include, but are not limited to, pumping, dispensing, extruding, conveying, vacuuming, extracting, separating, segregating, vortex generation, propulsion, metering, mixing, ramming, drilling, cutting, sawing, scraping, grinding, scrubbing, locomotion, mechanical motion translation and transmission, electrical power transmission, sampling and sensing/characterizing the physical properties of transportable media. Said devices may be of a range of dimensional scale on the order of picometers ($10^{-12}$) to several meters.

Still other benefits and advantages of the invention will become apparent to those skilled in the art to which it pertains upon a reading and understanding of the following detailed specification.

BRIEF DESCRIPTION OF THE DRAWINGS

FIG. 1a is a front view of the device embodiment depicted in FIG. 1.

BEST MODE FOR CARRYING OUT THE INVENTION

The following terms may be used throughout the descriptions presented herein and should generally be given the following meaning unless contradicted or elaborated upon by other descriptions set forth herein.

"Barrier" means a device or other structure that separates or holds apart.

"Electromechanical" and "electromechanical device" may be used interchangeably and describe a family of electrical/mechanical devices that can either produce a mechanical output as a result of an electrical input or can produce an electrical output as a result of an mechanical input.

"Electromotive device" means a device that produces, or tends to produce, electricity or an electric current, or causes electrical action or effects.

"Magnet" means an object that is surrounded by a magnetic field and that has the property, either natural or induced, of attracting iron or steel.

"Module" means a self-contained component, unit, or item.

Figure 1:
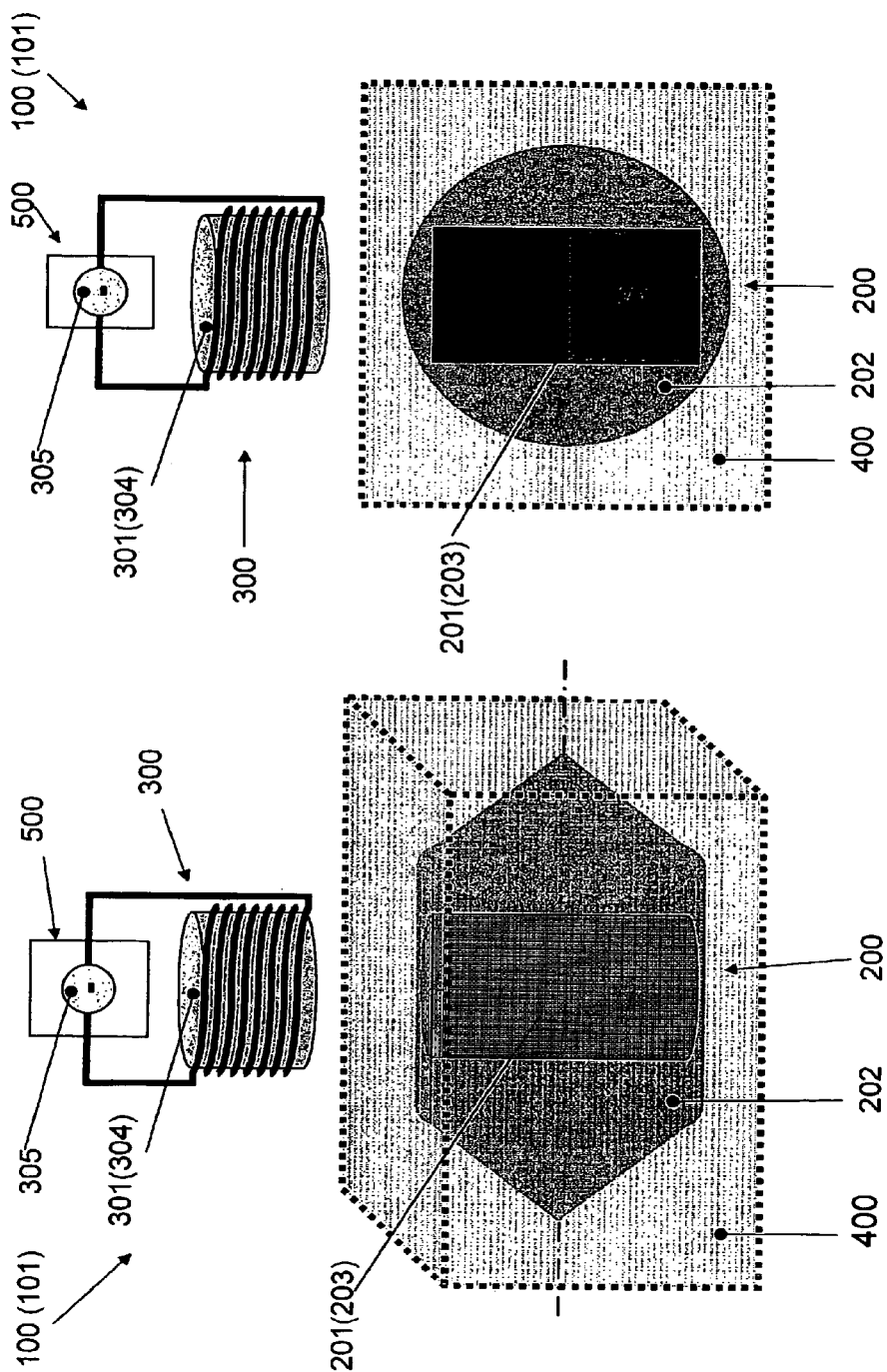
FIG. 1 is a schematic view of a modular magneto-mechanical device according to one embodiment of the invention.

A module can be used in combination with other components or other modules. Referring now to the drawings wherein the showings are for purposes of illustrating embodiments of the invention only and not for purposes of limiting the same, FIGS. 1 and 1a show a simple embodiment of a 3MD device 100, wherein the 3MD device 100 is comprised of a rotor 200, a stator 300, and a module 400. The rotor may comprise a first magnet 201. The stator 300 may comprise a second magnet 301. The module 400 may at least partially house the rotor 200 and during normal operation of the 3MD device 100 the stator 300 is positioned external to and separate from the module 400. The 3MD device 100 may be a electromechanical device. According to one embodiment of the invention, the 3MD device 100 may be a 3MD brushless electric motor device 101 and may further include a control assembly 500. In another embodiment of the invention, the 3MD device 100 may be a 3MD electromotive device 102 (as shown in FIG. 21).

Figure 2:
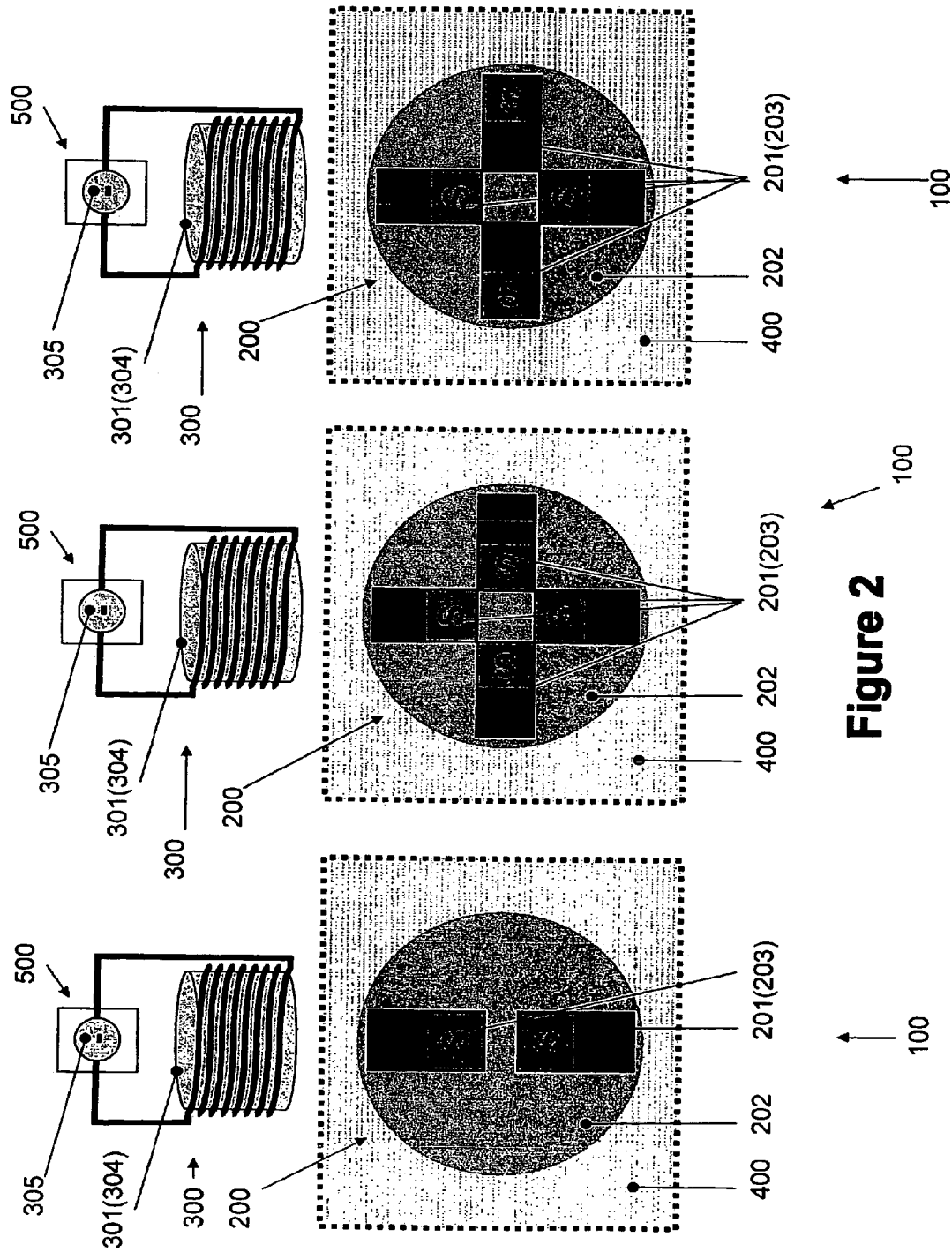
FIG. 2 is a modular magneto-mechanical device wherein the rotor and the stator each comprise a plurality of magnetic devices according to one embodiment of the invention.
Figure 3:
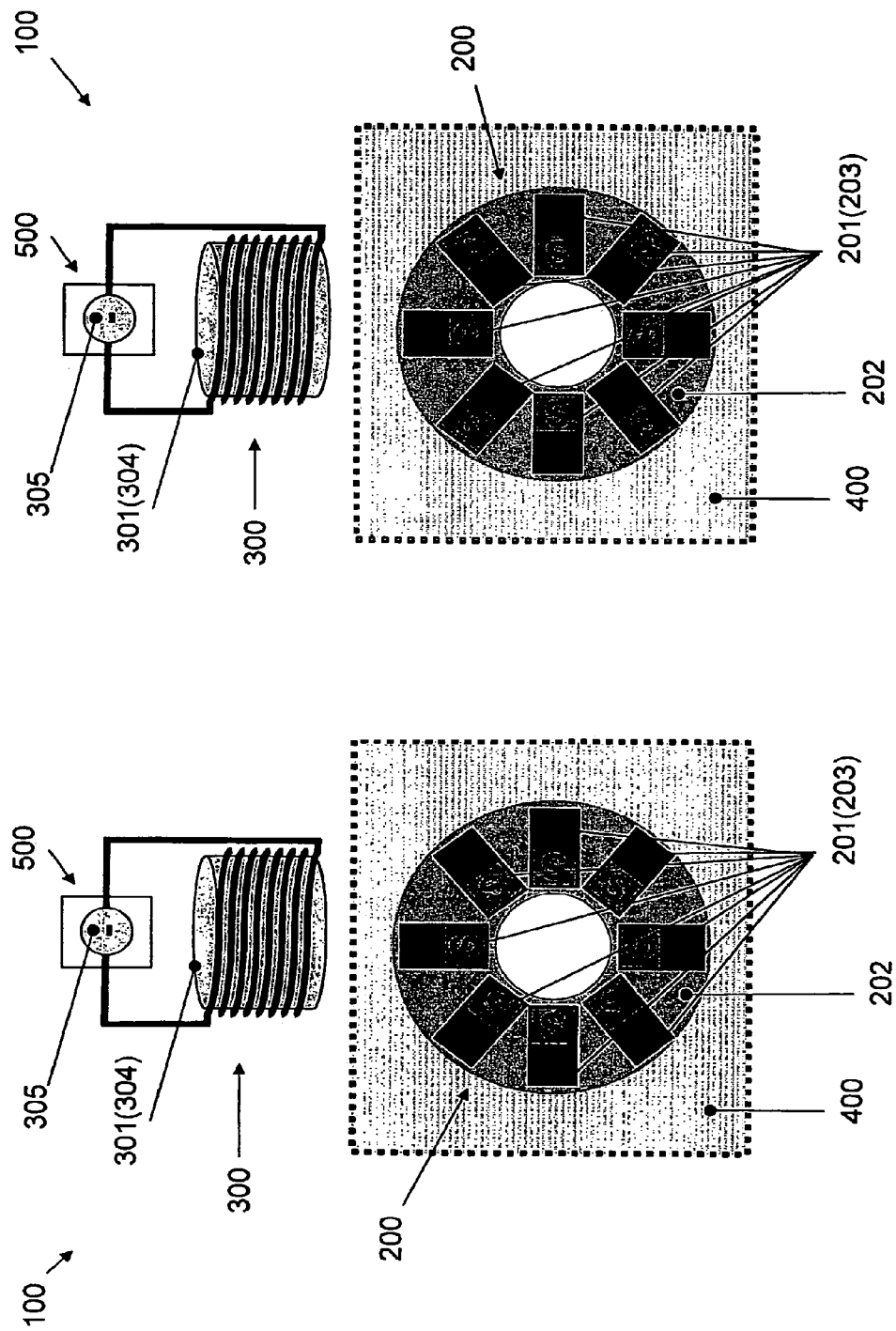
FIG. 3 is a modular magneto-mechanical device wherein the rotor comprises a plurality of permanent magnets according to one embodiment of the invention.
Figure 4:
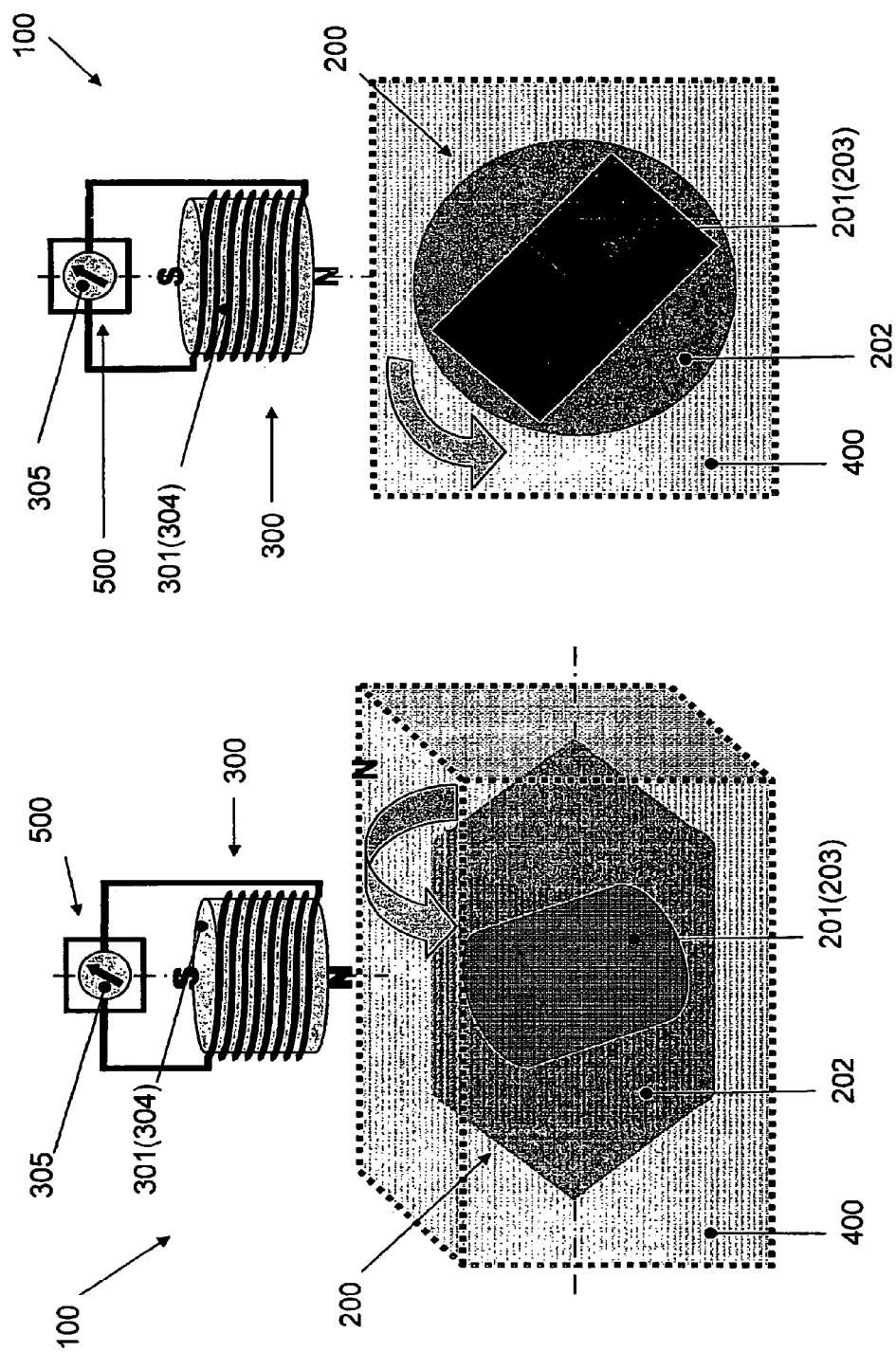
FIG. 4 is a modular magneto-mechanical device wherein the rotation of the rotor relative to the stator is varied according to one embodiment of the invention.
Figure 5:
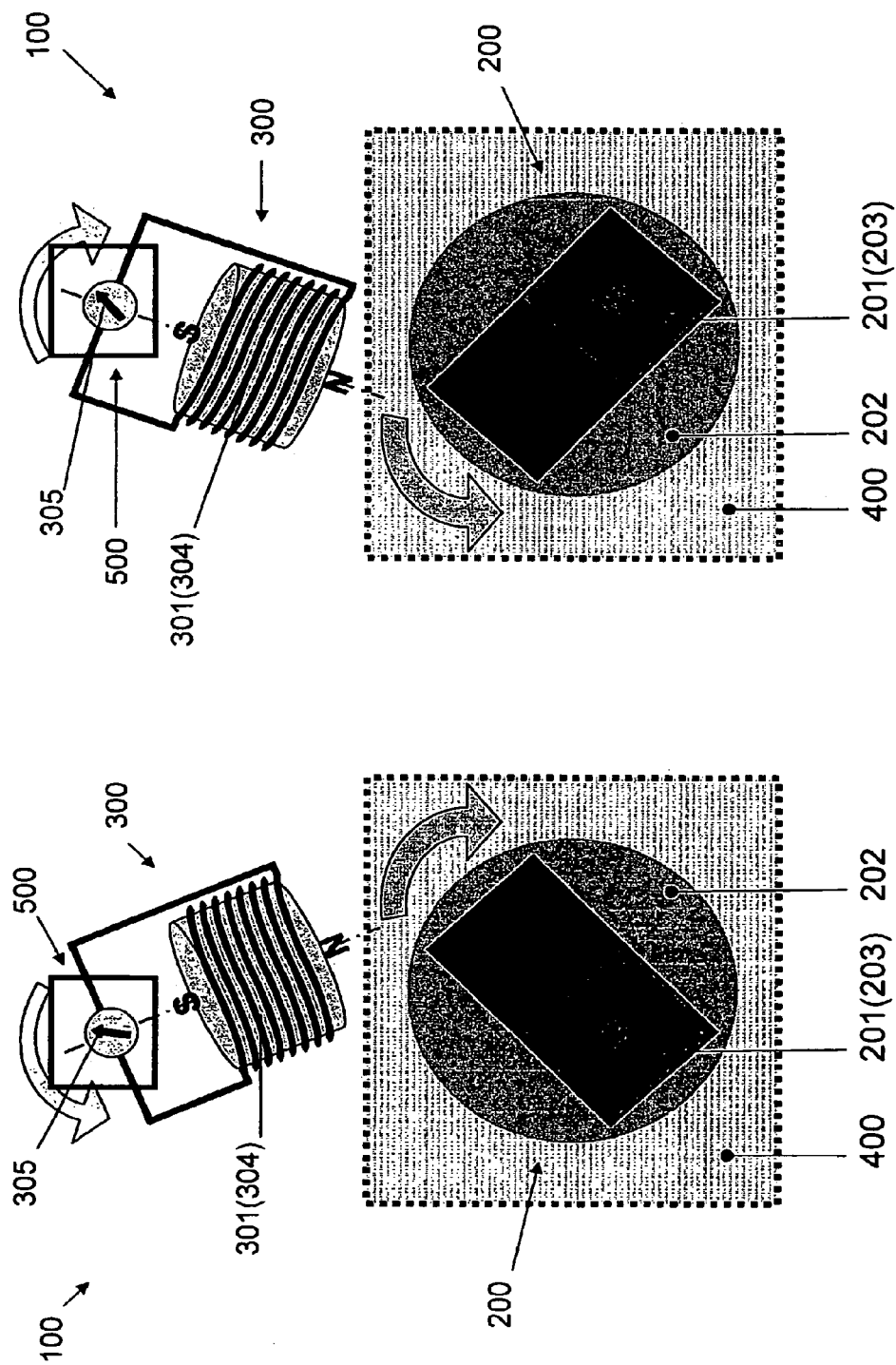
FIG. 5 is a modular magneto-mechanical device wherein the orientation and location of the rotor relative to the stator is varied to control the motion of the rotor according to one embodiment of the invention.
Figure 6:
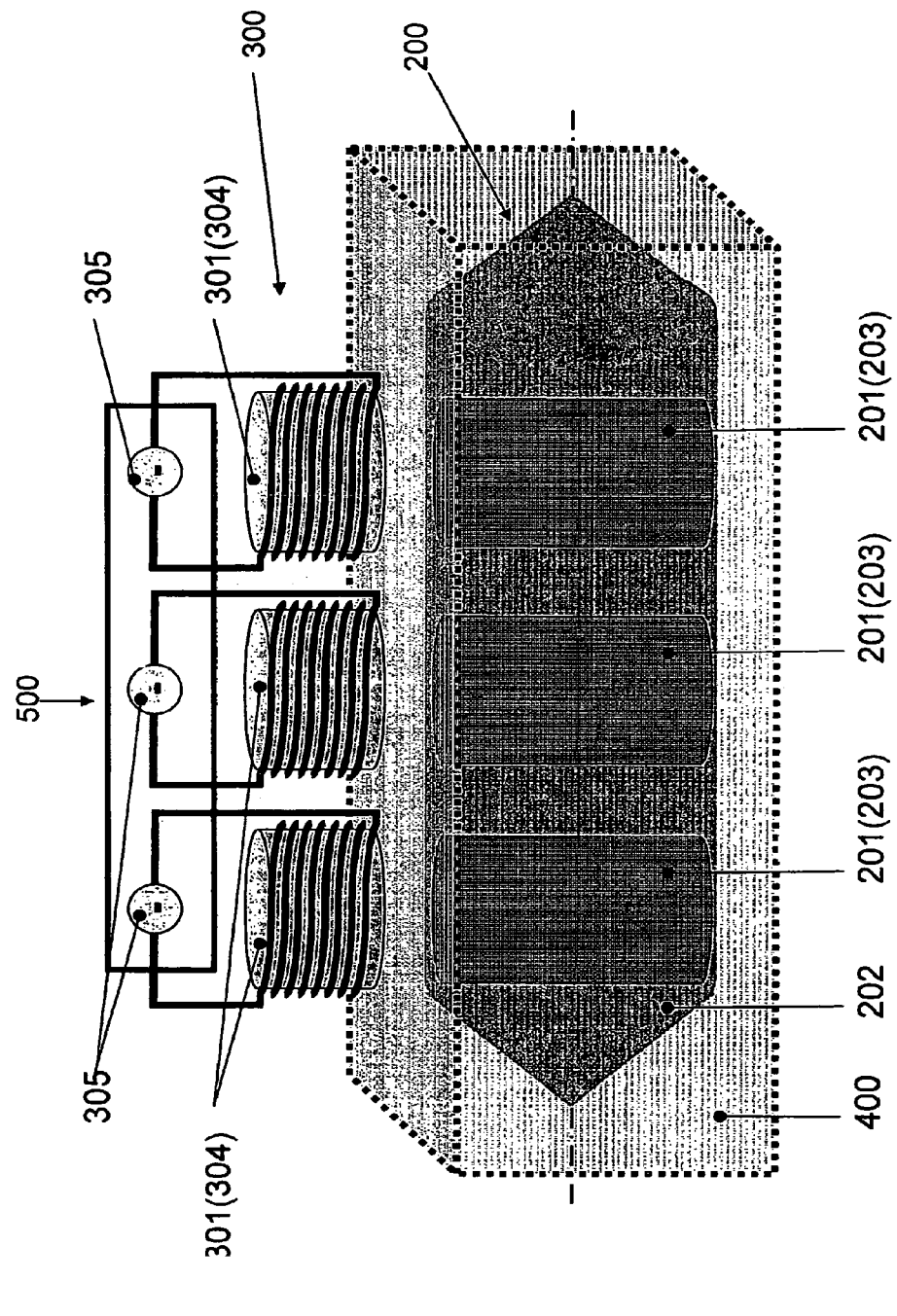
FIG. 6 is a modular magneto-mechanical device wherein the rotor comprises a plurality of permanent magnets and the stator comprises a plurality of electromagnets according to one embodiment of the invention.

With reference now to FIGS. 1-10, in a simple embodiment, the rotor 200 of a 3MD device 100 may be comprised of one or more permanent magnet elements 203 contained within a rotating spindle 202 that may be solid or hollow and may be housed within the module 400 as depicted in FIGS. 1, 2, and 3. In an alternative configuration the spindle 202 may be substantially comprised of one or more permanent magnetic materials the field orientation of which may be controllably magnetized. In one embodiment, the spindle 202 may function as, and therefore comprise, the first magnet element 201 of the rotor 200. In one embodiment of the invention, the rotor 200 may be comprised of multiple permanent magnet elements 203, the relative polarity of each successive permanent magnet element 203 may be contained within the spindle 202 and may be identical, opposite, or any conceivable combination associated therewith. The axis defining the poles of the permanent magnet element 203 may be positioned orthogonal to the spindle's axis of rotation such that a magnetic field generated by an independent electromagnet 304 and a controllable electrical current source 305 external to the 3MD device 100 may be used to either attract or repel the respective magnetic poles of the spindle 202, thus driving spindle rotation as depicted in FIG. 4. By controlling the sequence of repulsive or attractive electromagnetic fields generated, the spindle's motion and rotation can thus be controlled. FIG. 5 depicts a variation of said embodiment in which a variable and controllable orientation angle of the externally applied magnetic field can be incorporated with relation to the primary axis of the spindle. FIGS. 6, 7, 8, 9 and 10 depict other variations of said embodiment in which multiple permanent magnet elements 203 are incorporated in the spindle 202, and multiple independent electromagnets 304 are used for the external magnetic field generation controlling the rotation of the 3MD spindle 202. Those skilled in the art will recognize that other conceivable variations of said embodiment may exist.

With reference now to FIGS. 5-10, the FIGURES depict variations of said embodiment in which a variable and controllable orientation angle of the externally applied magnetic field can be incorporated with relation to the primary axis of the spindle 202. Other variations of said embodiment in which multiple permanent magnet elements 203 are incorporated in the spindle 202, and multiple independent electromagnets 304 are used for the external magnetic field generation controlling the rotation of the 3MD spindle 202. Those skilled in the art will recognize that other conceivable variations of said embodiment may exist, and any position or number of first and second magnet elements chosen with sound engineering judgment may be used. Rotation of the spindle 202 described in the aforementioned embodiment may be held on a fixed axis defined by single or multiple bearing means as is well known in the art. Such forms of bearing means may include but are not limited to radial ball bearings, needle bearings, roller bearings, bushings, cone and v-block bearings, jewel bearings, fluid journal bearings, air bearings, magnetic bearings, and/or any other conceivable bearing means apparent to those skilled in the art.

Figure 21:
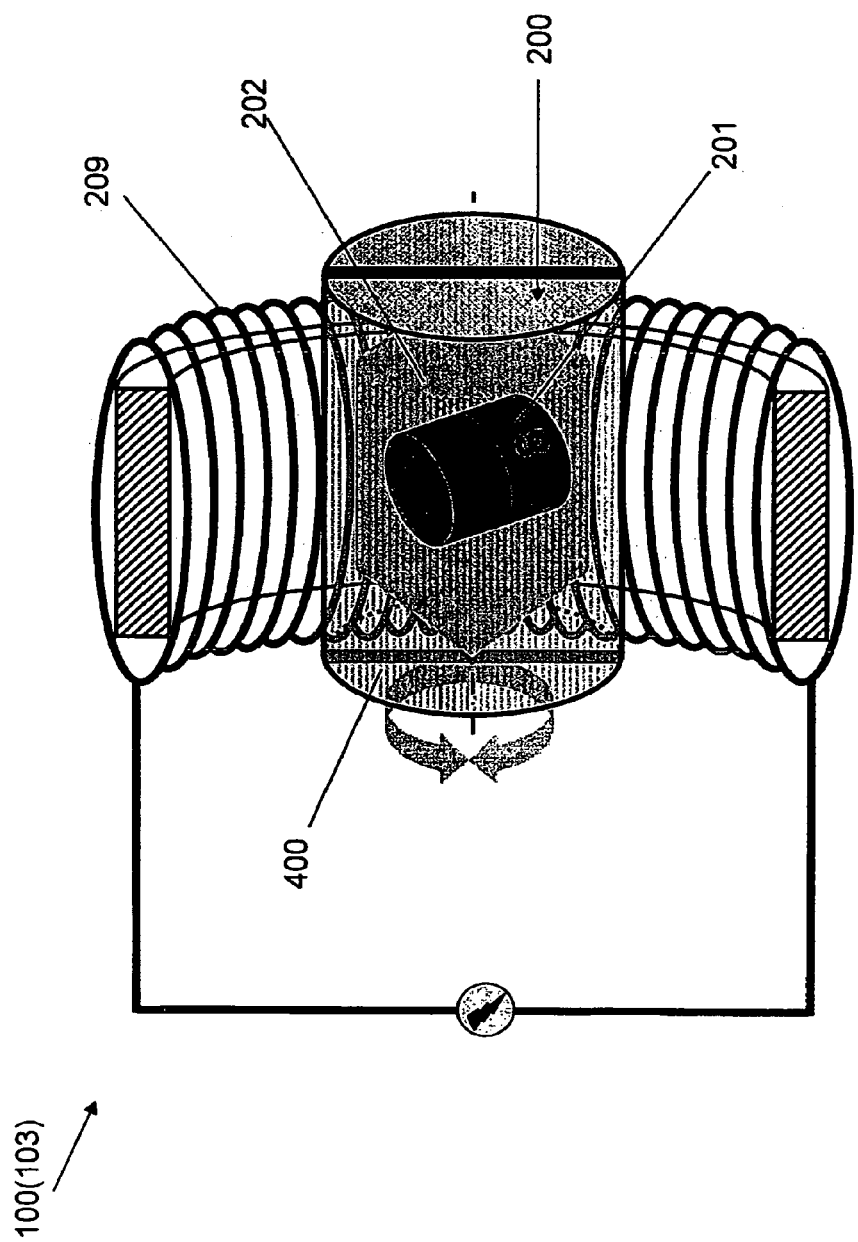
FIG. 21 is a module of a modular magneto-mechanical device that induces an electric current in a conductive coil according to one embodiment of the invention.
Figure 22:
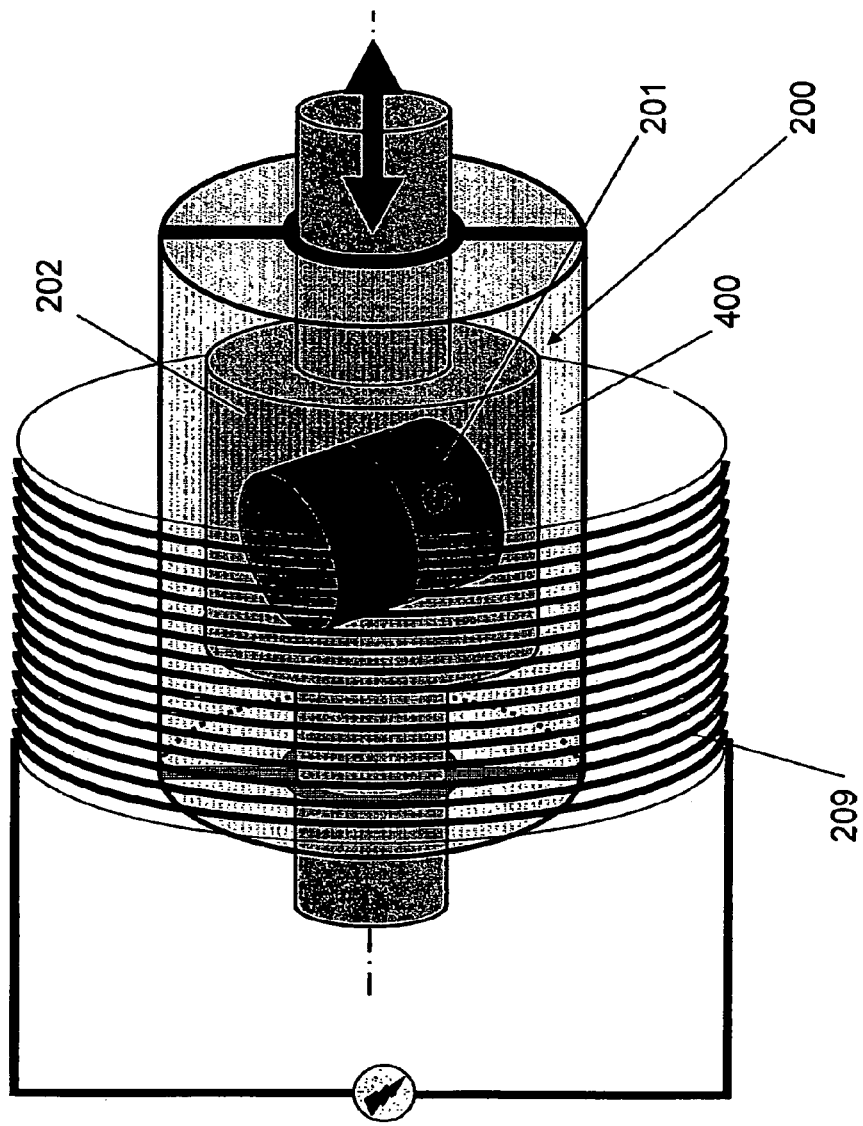
FIG. 22 is a module of a modular magneto-mechanical device that induces an electric current in a conductive coil according to one embodiment of the invention.
Figure 23:
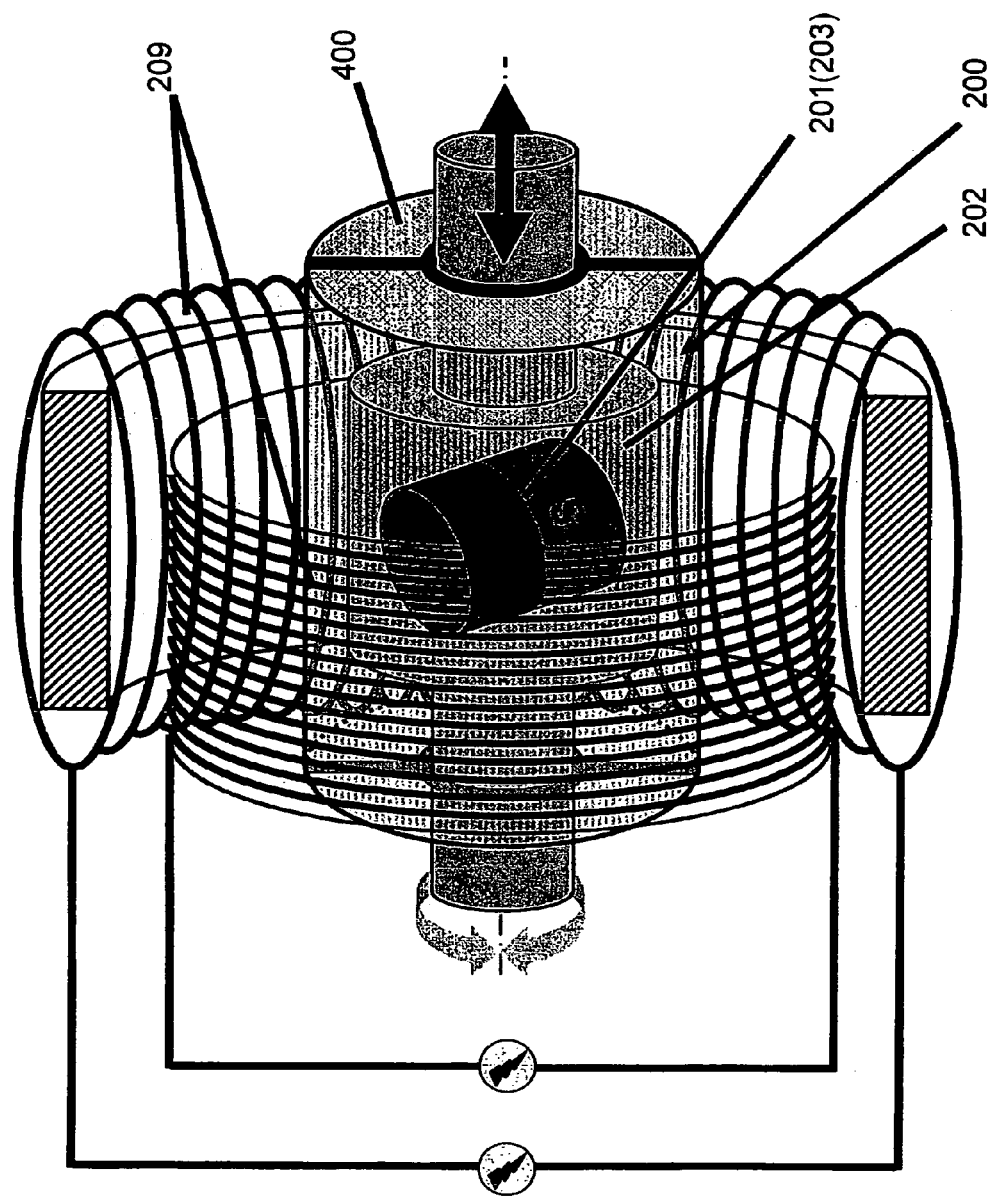
FIG. 23 is a module of a modular magneto-mechanical device that induces an electric current in a conductive coil according to one embodiment of the invention.

With reference now to FIGS. 21-23, another variation of said 3MD device 100 includes the 3MD device 100 functioning as a 3MD electromotive device 103 wherein the spindle 202 incorporates the use of the rotor 200 comprising one or more electromagnetic elements 204 within the rotating spindle 202. As depicted in the embodiment of FIG. 21, a single electromagnetic coil 205 may be used to define the magnetic poles of the electromagnetic element 204. According to one embodiment, a current supplied through the aforementioned bearing means may control the field strength and polarity of the contained electromagnetic coil 205 as generated by an external, controllable electrical current source 305. FIG. 23 depicts a variation of said spindle 202 in which the spindle 202 further comprises multiple electromagnetic elements 204. Although these depicted illustrations represent variations of an electromagnetic spindle 202 for use on the 3MD device 100, those skilled in the art will recognize that other conceivable variations of said electromagnetic spindle embodiment may exist.

Figure 13:
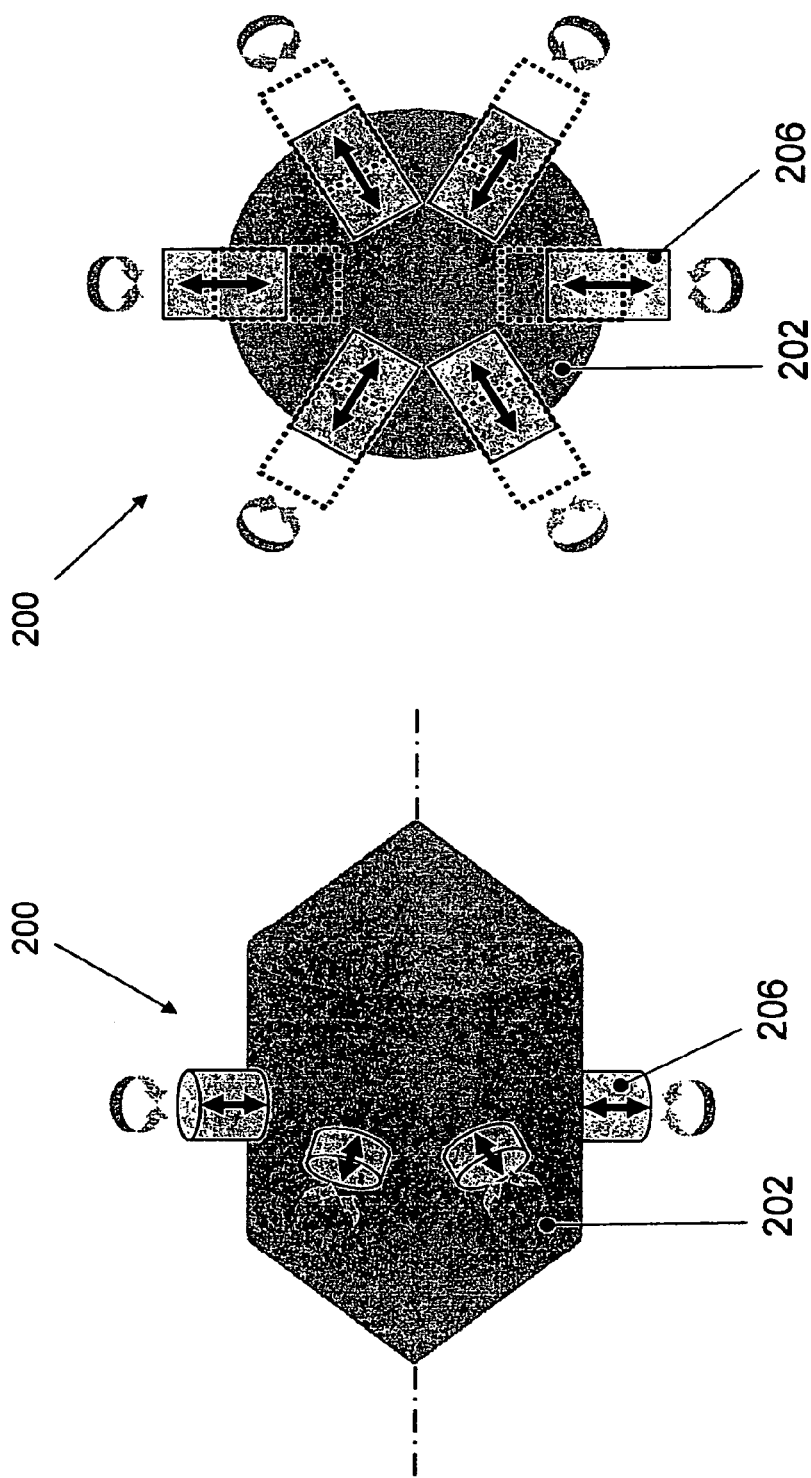
FIG. 13 is an independently movable element of a modular magneto-mechanical device according to one embodiment of the invention.

With reference now to FIG. 13, a further variation of said 3MD spindle 202 embodiments incorporates the use of one or more topographical features or independently movable elements 206 formed on the outer surface or within the 3MD spindle 202 and/or the module 400. The topographical features or independently movable elements 206 may be magnetically charged or magnetically responsive elements. According to another embodiment of the invention, the independently movable elements 206 are not magnetically charged or magnetically responsive elements. The position, orientation and/or location of said topographic features or independently movable elements 206 may be controlled by the motion of the spindle 202 and/or by an externally generated electromagnetic field. In one embodiment of the invention, the externally generated electromagnetic field may be generated by the stator 300. Such forms of the topographical features or independently movable elements 206 may include but are not limited to variable incident angle or depth rotor vanes, variable height rotor pins or housing protrusions, variable helical depth or width screw channel geometries, variable aperture or porosity meshes and membranes, and/or any other conceivable form of controllably movable elements apparent to those skilled in the art chosen with sound engineering judgment.

Figure 7:
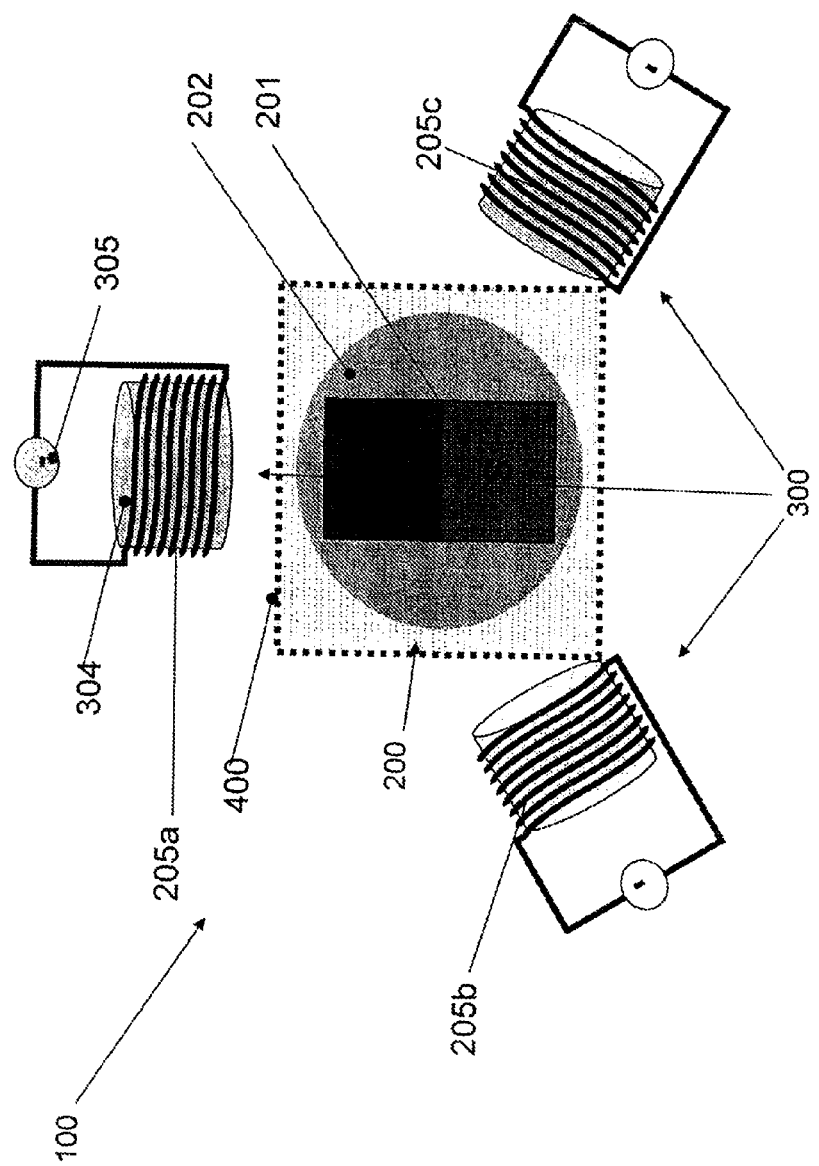
FIG. 7 is a modular magneto-mechanical device wherein the stator comprises a plurality of electromagnets according to one embodiment of the invention.
Figure 8:
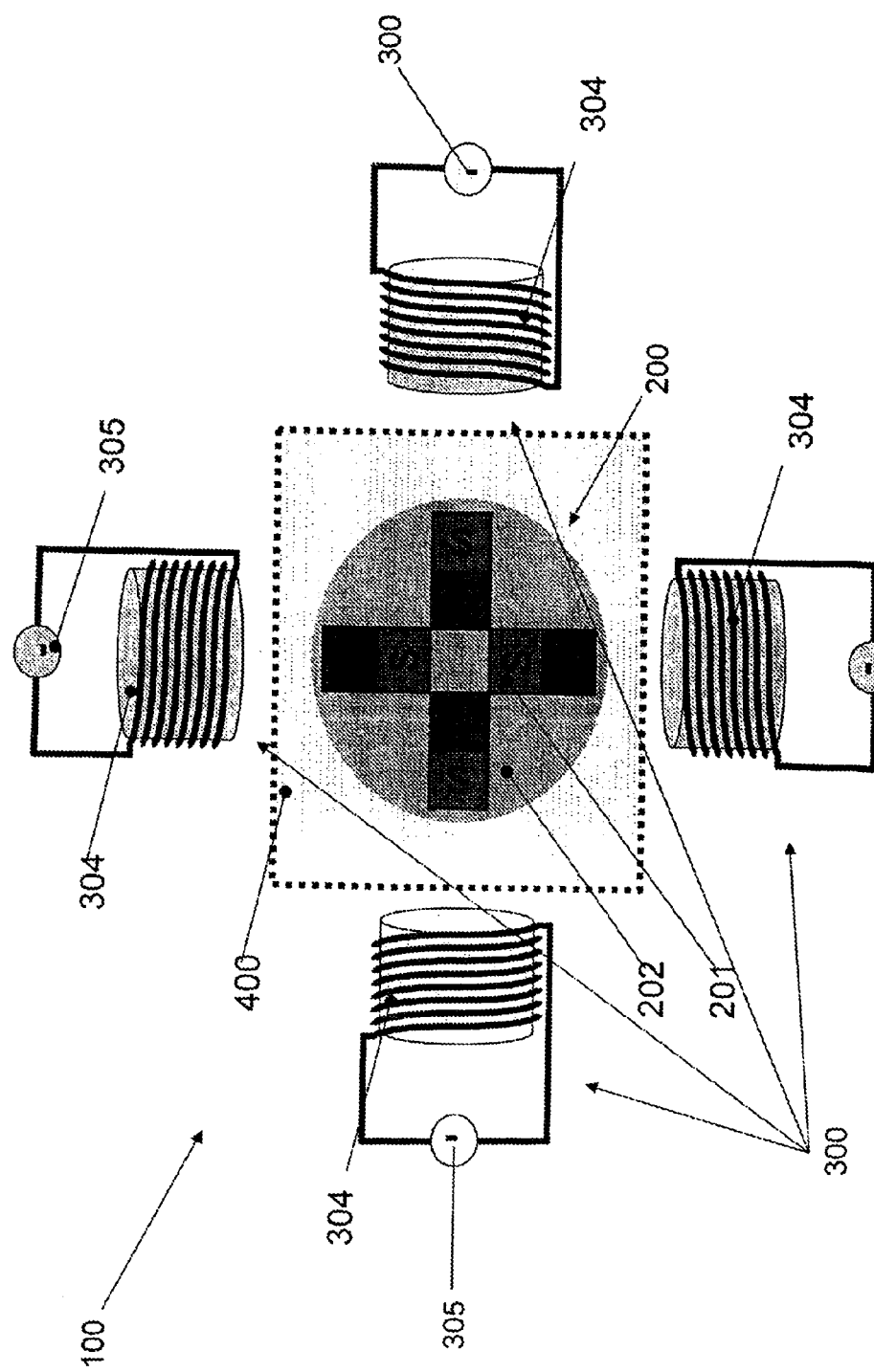
FIG. 8 is a modular magneto-mechanical device wherein the rotor and the stator each comprise a plurality of magnetic devices according to one embodiment of the invention.
Figure 9:
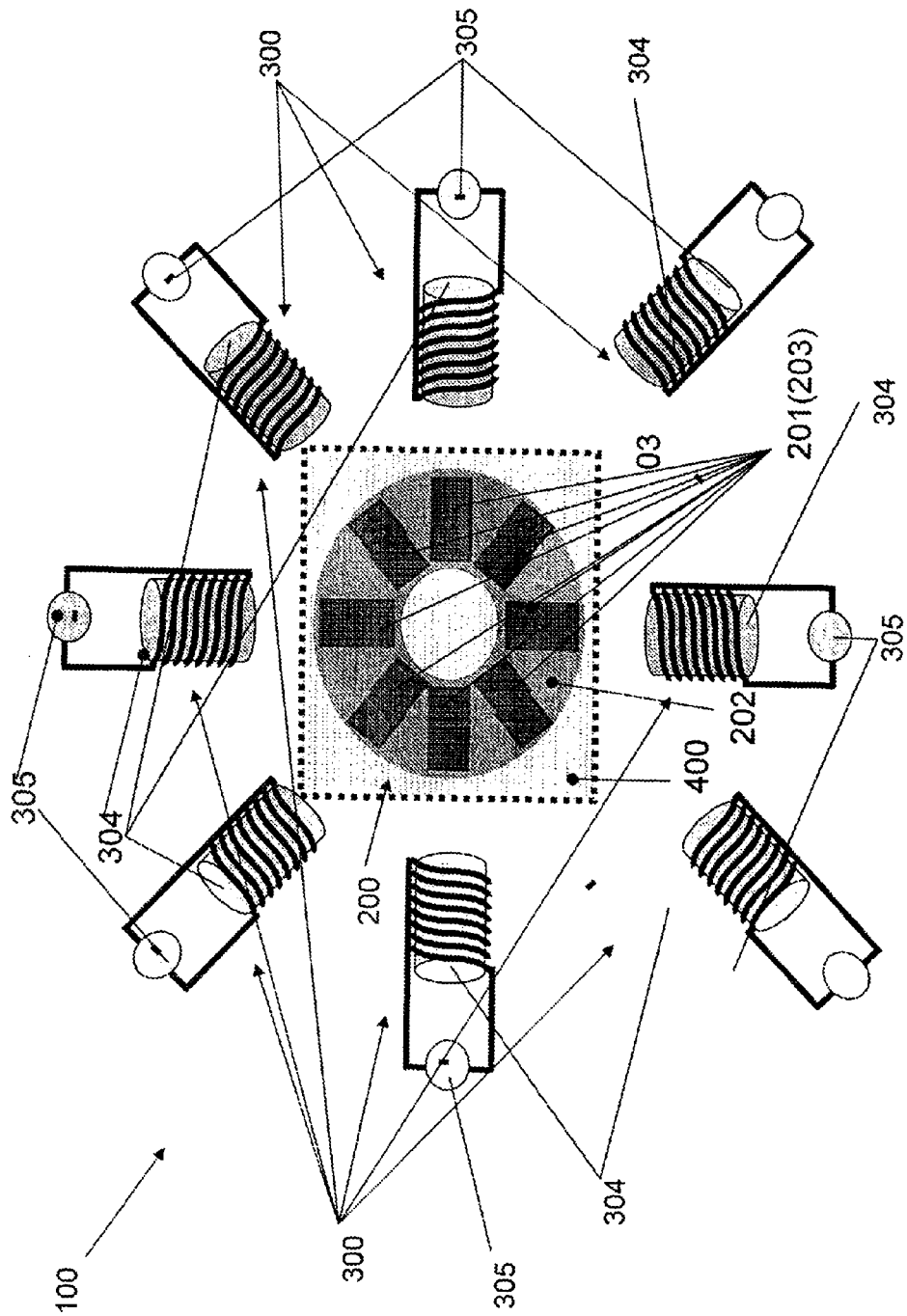
FIG. 9 is a modular magneto-mechanical device wherein the rotor and the stator each comprise a plurality of magnetic devices according to another embodiment of the invention.
Figure 10:
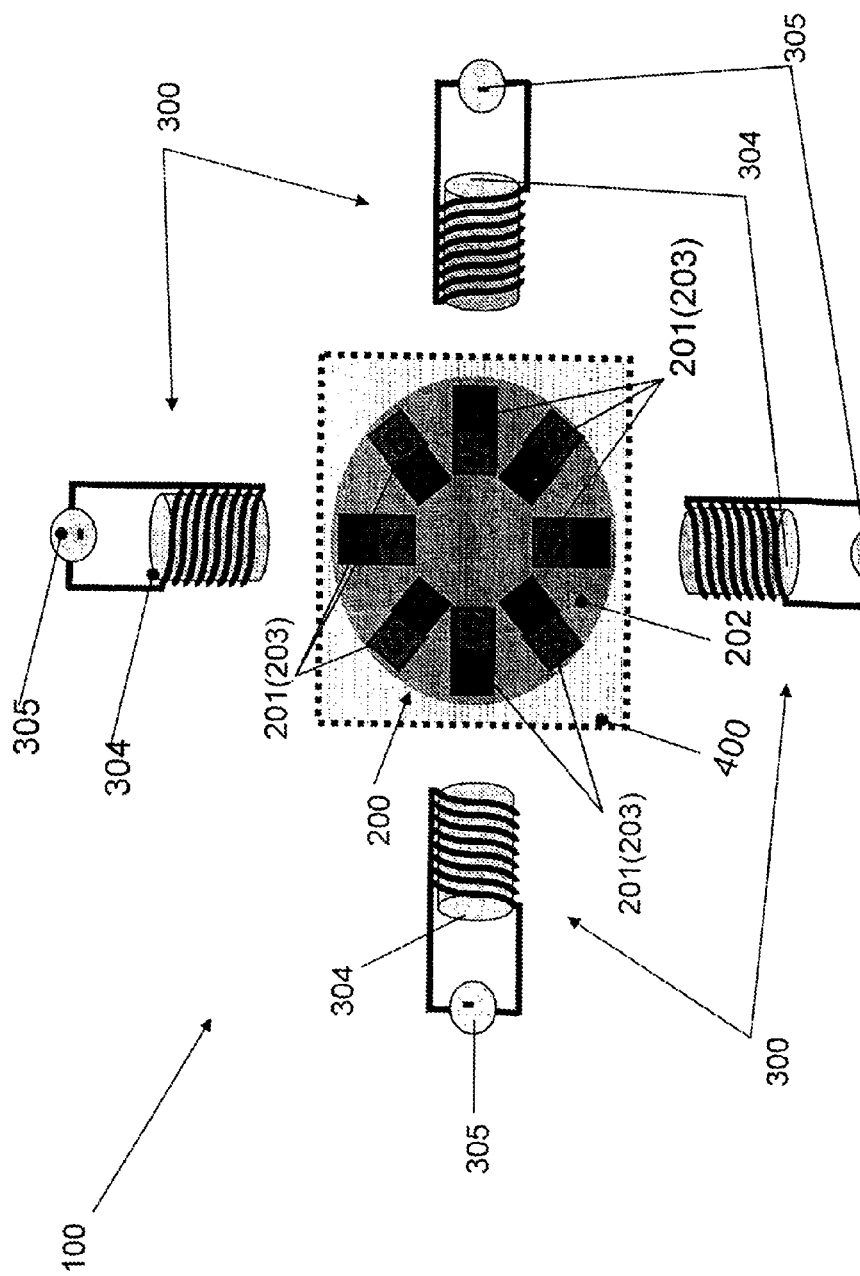
FIG. 10 is a modular magneto-mechanical device wherein the rotor and the stator each comprise a plurality of magnetic devices according to another embodiment of the invention.
Figure 11:
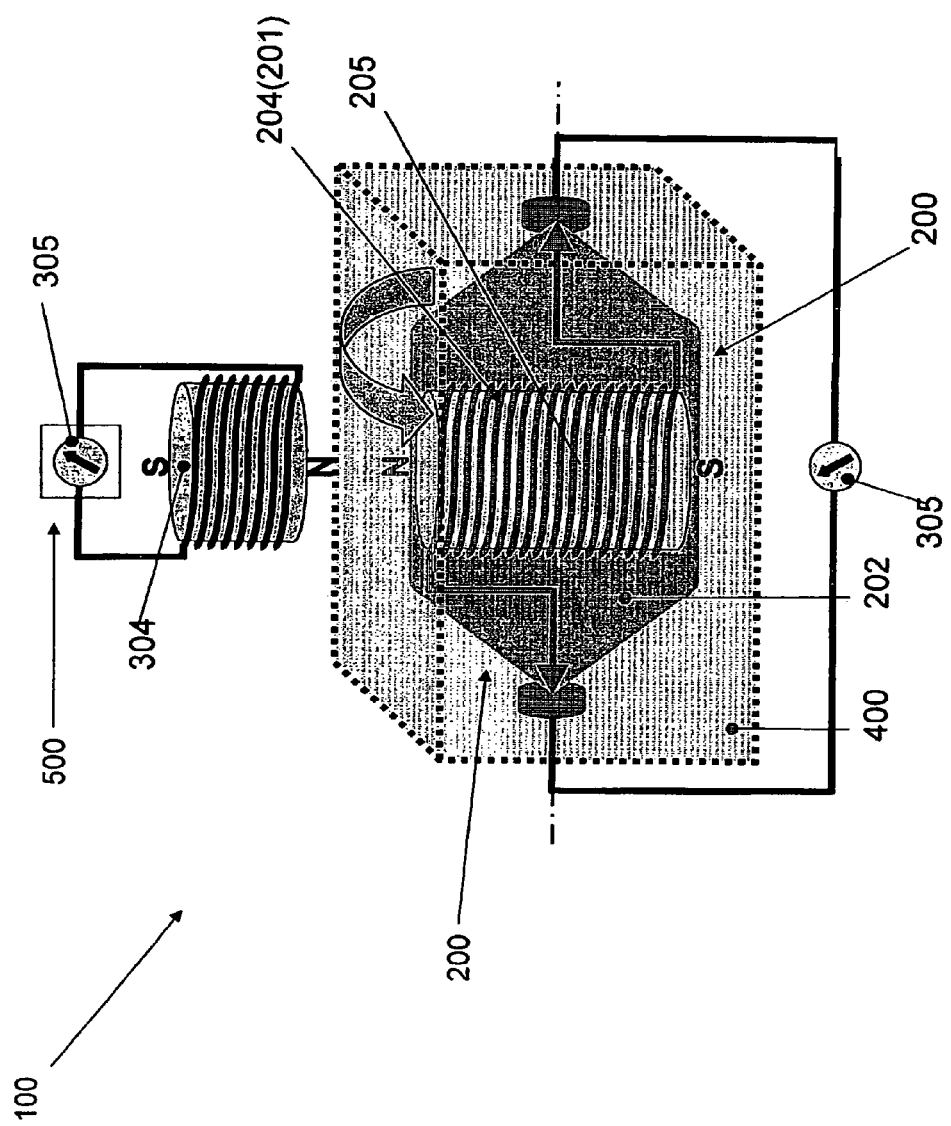
FIG. 11 is a modular magneto-mechanical device wherein the rotor and the stator each comprise an electromagnet according to one embodiment of the invention.
Figure 12:
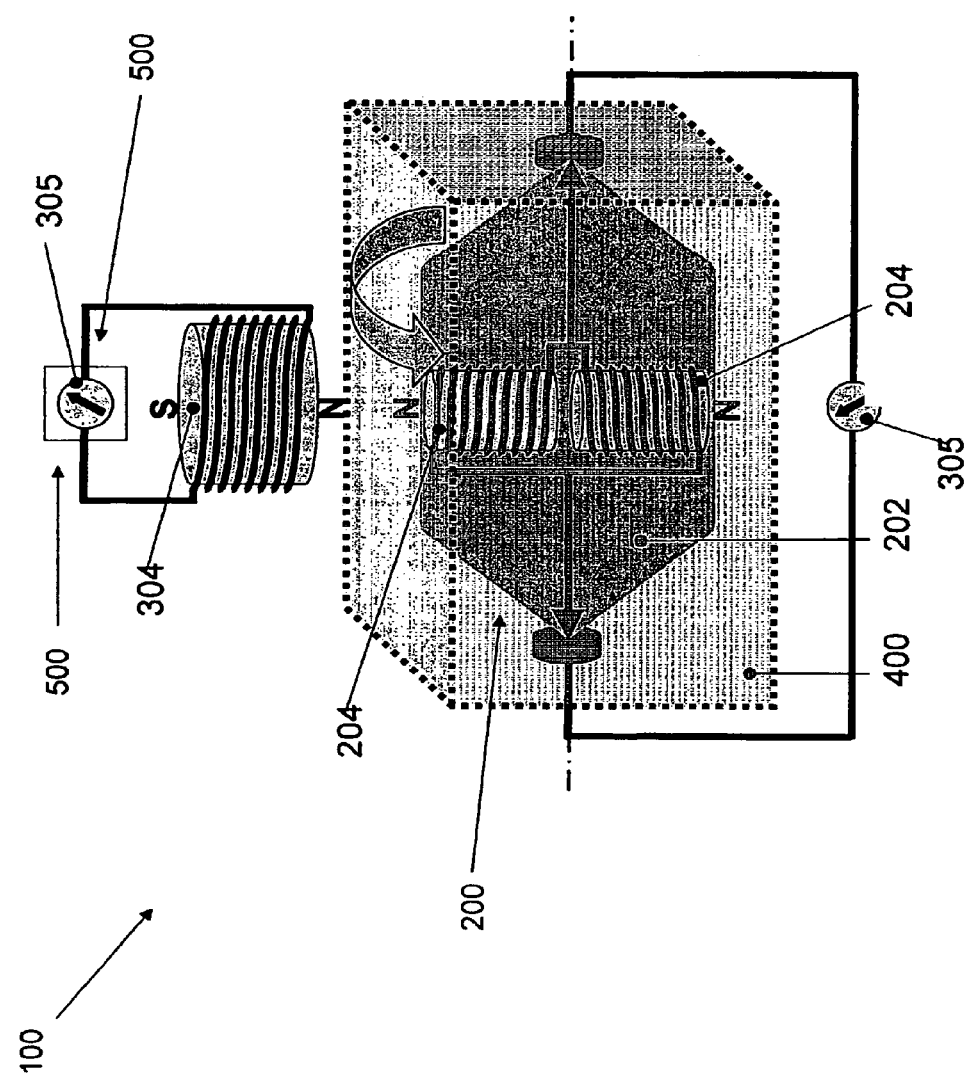
FIG. 12 is a modular magneto-mechanical device wherein the rotor comprises a plurality of electromagnets according to one embodiment of the invention.

With reference now to FIG. 7, in a further development of the aforementioned embodiments, a sensing means (not shown) external to the mechanical portion of the 3MD module 400 such as a Hall's effect sensor, electromagnetic induction coil, optical encoder, or other conceivable displacement and/or orientation sensing device can be incorporated into a 3MD control assembly 500 to allow for independent measurement of spindle rotation and/or orientation thereby establishing a feedback means for closed loop feedback control of the external magnetic field controlling the motion of the 3MD spindle 202. A variation of this embodiment may incorporate an array of Hall's effect sensors, electromagnetic induction coils, and/or other displacement/orientation sensing means in order to allow for a precise measurement of spindle rotation and/or orientation for precision closed-loop feedback control. According to one embodiment of the invention, any two of the electromagnetic coils $205a$, $205b$ surrounding the spindle 202 may be energized such that the resultant externally generated electromagnetic field may be used to controllably re-align the field polarity of the spindle 202 thereby causing the spindle 202 to rotate. The third electromagnetic coil $205c$ may be operated in a passive mode such that the magnetic field from the rotating spindle 202 induces a current in said passive coil $205c$ thereby serving to detect the relative orientation of said 3MD spindle 202. Hence, by monitoring the orientation of the spindle 202 via the passive conductor coil, the control assembly 500 can be triggered to sequentially and controllably energize any pair of electromagnetic coils 205 thereby controlling the rotation of said 3MD spindle 202 in a manner consistent with the operation of a sensorless brushless motor. Those skilled in the art will recognize that other sensing means and feedback loop variations may be incorporated in the control assembly 500 for closed-loop feedback control of the 3MD device 100.

Figure 14:
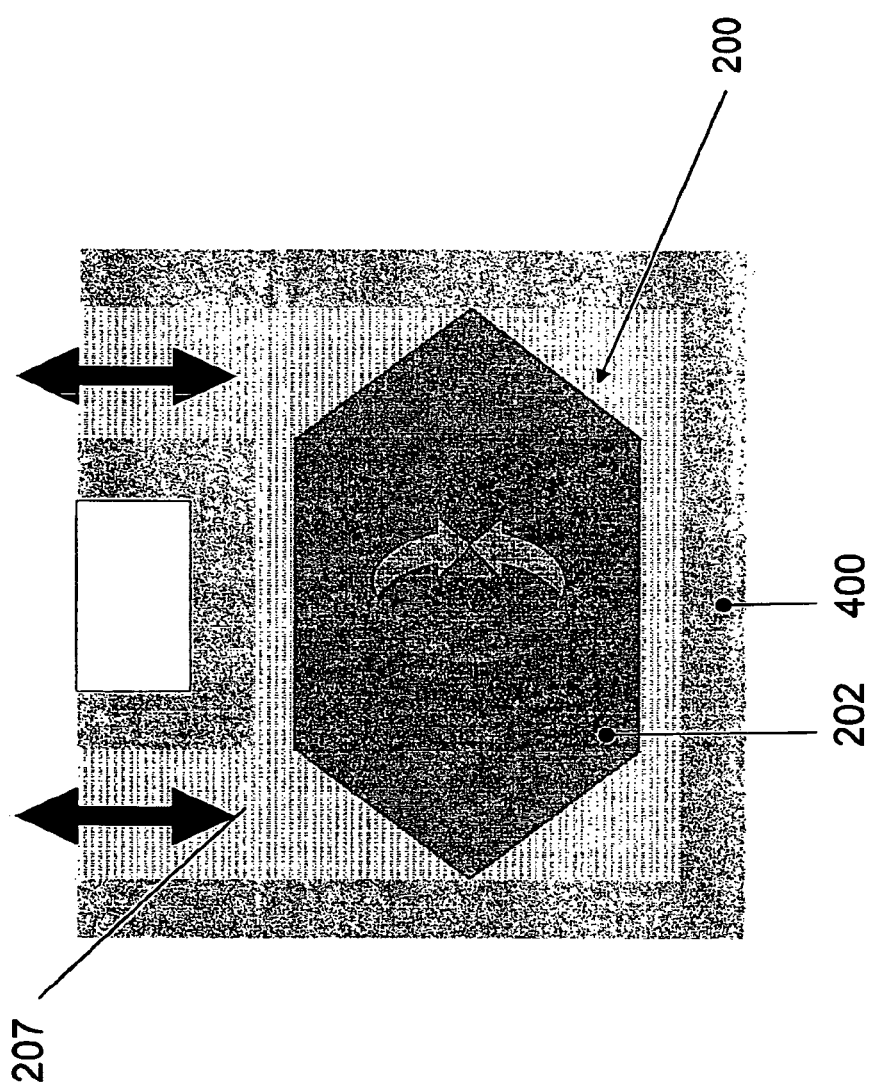
FIG. 14 is a modular magneto-mechanical device comprising a conduit according to one embodiment of the invention.
Figure 15:
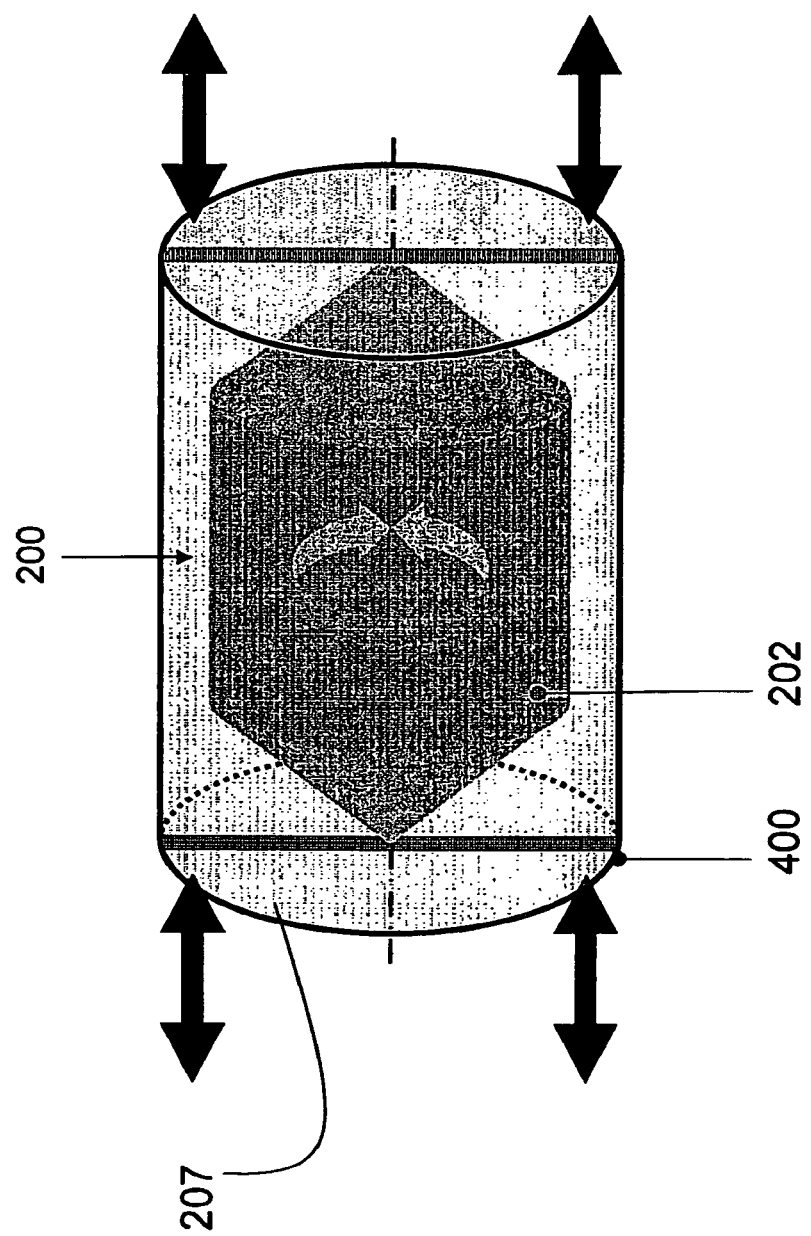
FIG. 15 is a modular magneto-mechanical device comprising a conduit according to another embodiment of the invention.
Figure 16:
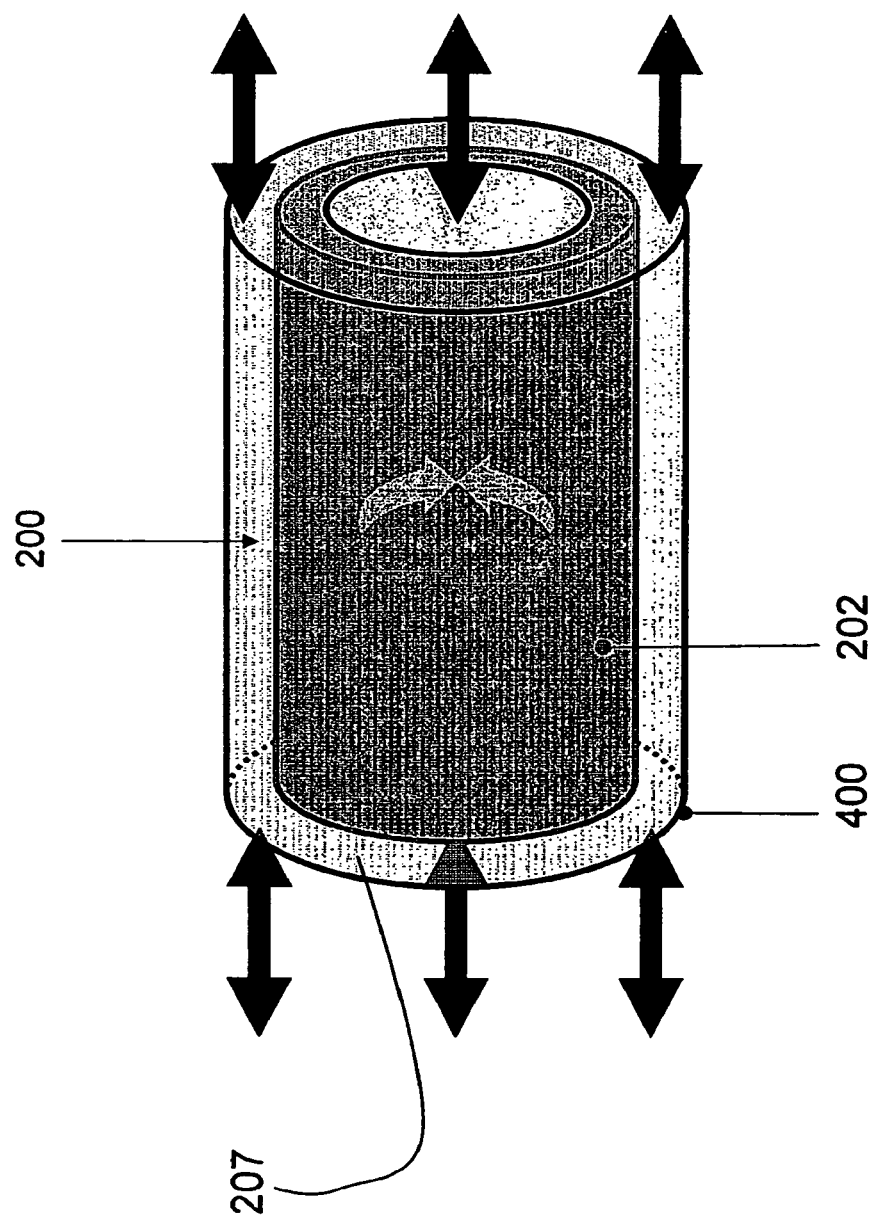
FIG. 16 is a modular magneto-mechanical device comprising a conduit according to another embodiment of the invention.
Figure 17:
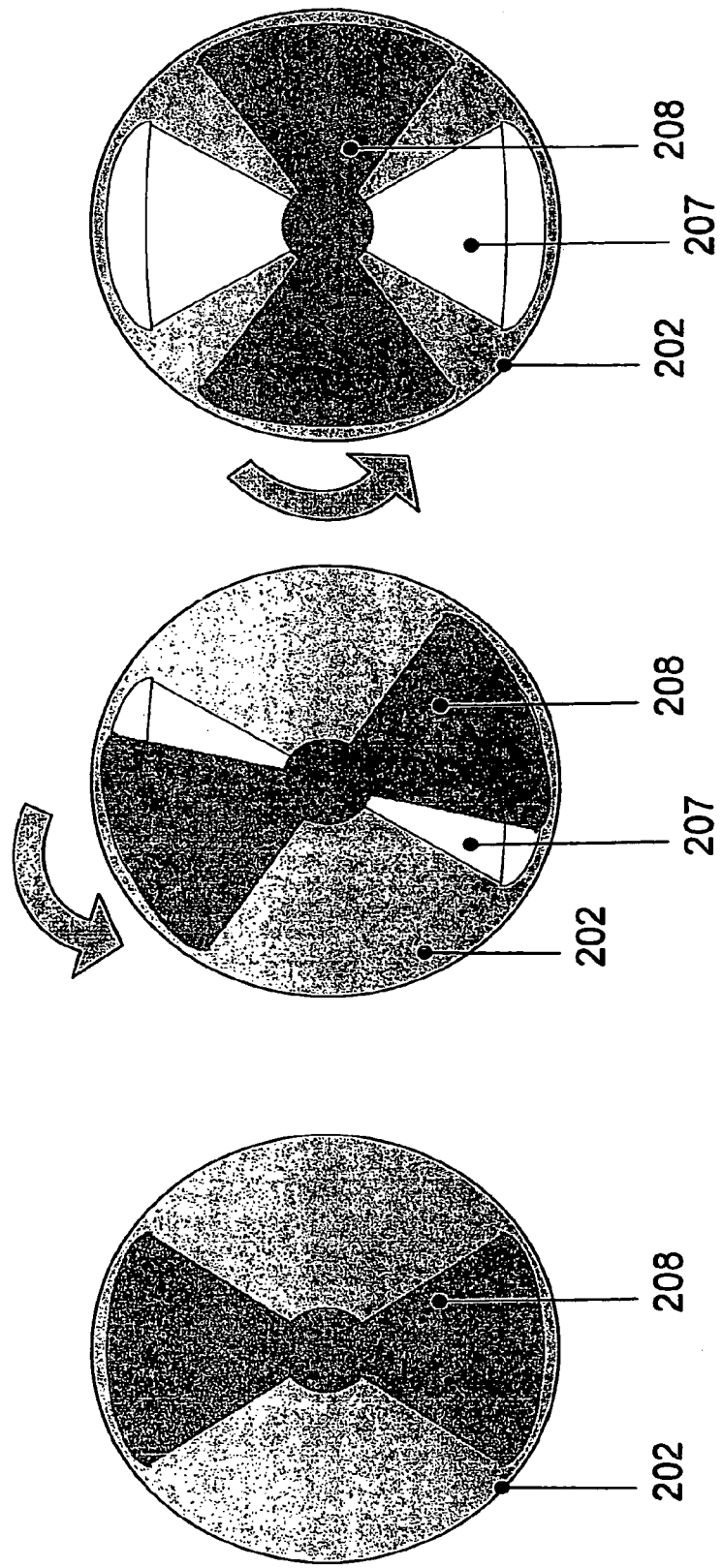
FIG. 17 is a variable valve assembly of a modular magneto-mechanical device according to one embodiment of the invention.

With reference now to FIGS. 14-17, the rotating spindle 202 of the 3MD device 100 may be at least partially housed or positioned within a hollow container or conduit 207 as depicted in FIG. 14, such that transportable media may be allowed to exit the container or conduit 207 or pass from one end of the container or conduit 207 to the other. FIG. 15 depicts a further development of this embodiment, in which a cylindrical 3MD spindle 202 is housed within a hollow cylindrical conduit 207 thereby defining an annular region through which transportable media may be allowed to pass. FIG. 16 depicts a variation of this embodiment in which a hollow cylindrical 3MD spindle 202 is at least partially housed or positioned within a hollow cylindrical conduit 207 thereby defining coaxial portals through which transportable media may be allowed to pass in similar or opposing directions. In another variation, multiple hollow cylindrical 3MD spindles 202 are at least partially housed or positioned within a hollow cylindrical conduit 207 thereby defining coaxial multi-annular portal regions through which transportable media may be allowed to pass in a multitude of directional combinations. In yet another variation, as shown in FIG. 17, the conduit 207 at least partially housing the spindle 202 may contain one or more distinct apertures that may be variably opened or closed as a result of controlled spindle position and/or orientation thereby defining an adjustable valve mechanism 208. Any of these said embodiments may be configured to allow for a multitude of entrance and/or exit ports to or along the 3MD module 400. Said entrance and/or exit ports can also be configured with directional flow valves or apertures to allow for directional media transport to and from said 3MD module 400. Those skilled in the art will recognize that other spindle 202, module 400, and/or conduit 207 geometry variations, chosen with sound engineering judgment, may be incorporated in the 3MD device 100 design to allow for the passage of transportable media.

Figure 50:
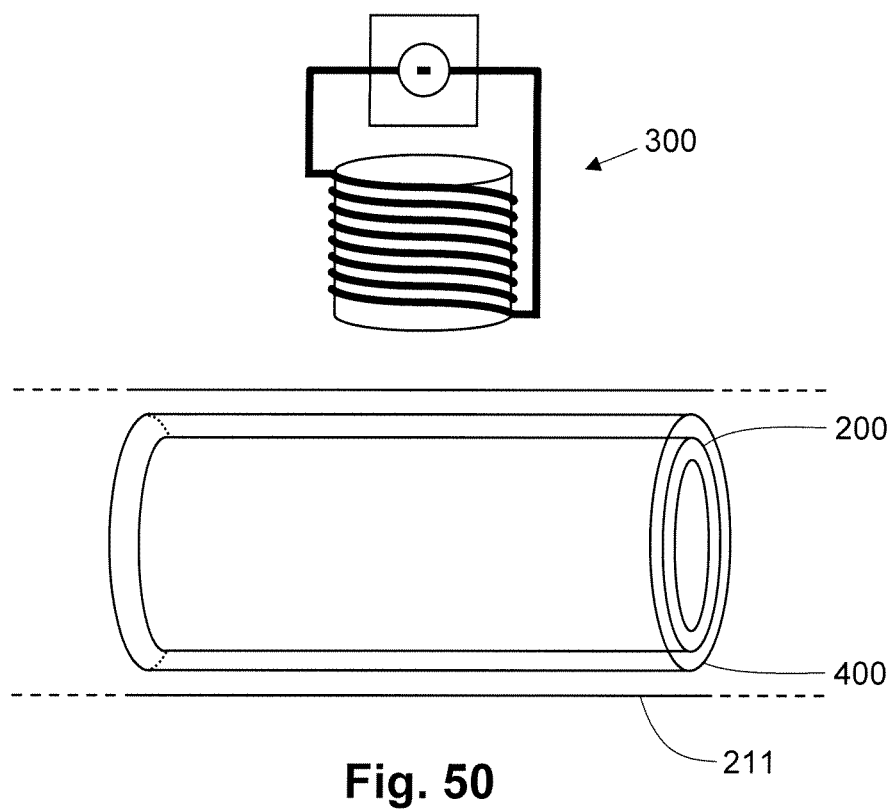
FIG. 50 shows a modular electromechanical device according to one embodiment of the invention.

In one embodiment, as shown in FIG. 50, an electromechanical device comprises a rotor 200, a stator 300, and a module 401 that at least partially houses the rotor 200. The module 401 is contained within a conduit or vessel 211. The stator 300 is positioned external to and separate from the conduit or vessel 211.

Figure 18:
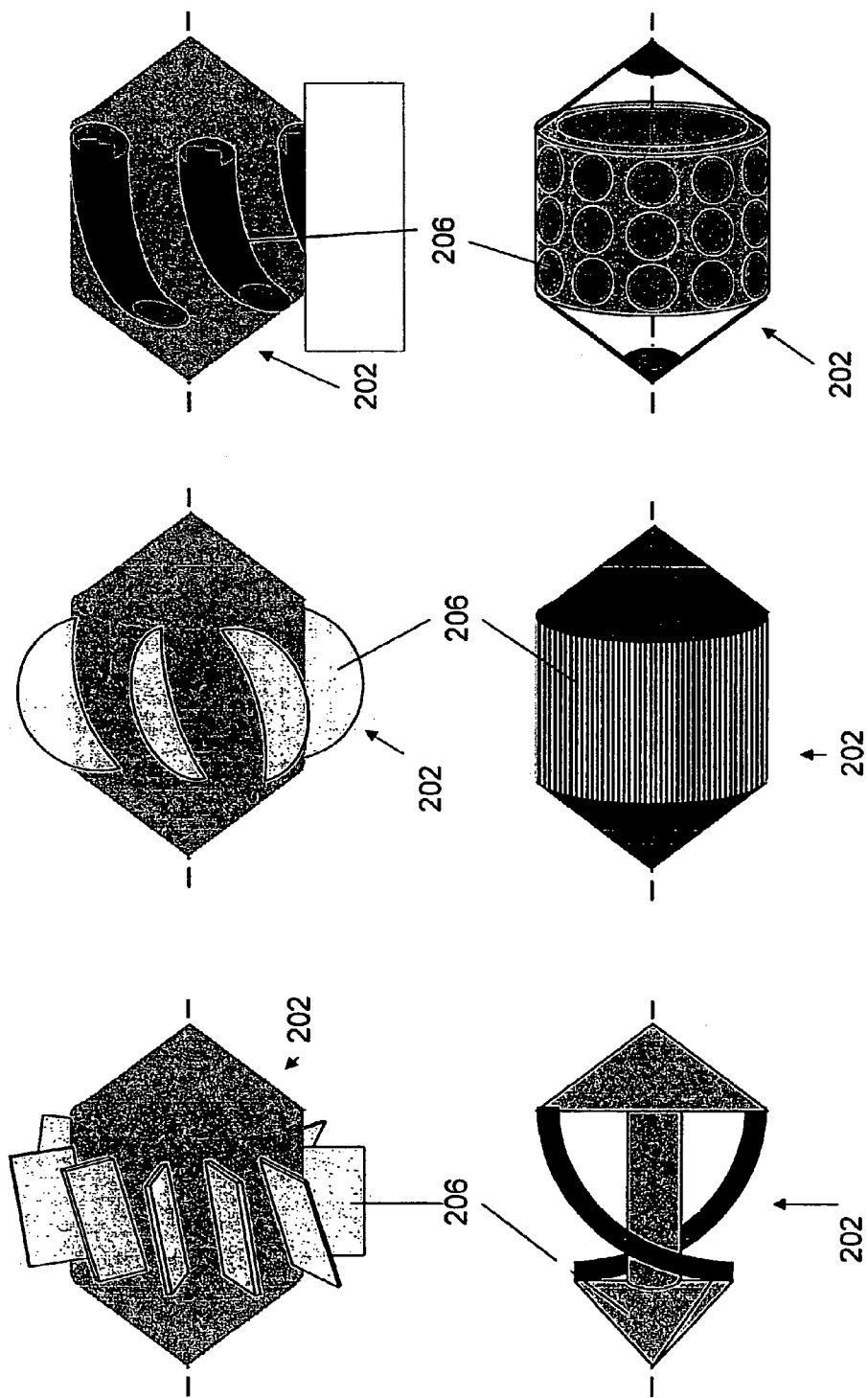
FIG. 18 is a perspective view of a variety of 3MD spindle topographical feature configurations.

With reference now to FIG. 18, any of the previously described 3MD spindle 202 embodiments may be topographically configured to incorporate a means for the conveyance, pumping, agitation, and/or mixing of transportable media. Such topographical features 206, a few of which are depicted in FIG. 18, may include but are not limited to rotor blades, rotor wings, compressor vanes, propeller/impeller blades, paddle blades, sigma blades, ribbon blades, flighted screw channels, helical grooves, lobed convolutions, grooved convolutions, epitrochoidal rotors, eccentric shaft sections/protuberances, kneader blocks, flutes, perforated rotors, perforated cylinders, and gear teeth. Those skilled in the art will recognize that other conceivable spindle 202 features, chosen with sound engineering judgment, may be incorporated in the 3MD device 100 to allow for the conveyance, pumping, agitation, and/or mixing of transportable media. Any of the previously described 3MD device 100 embodiments may also be configured to incorporate a means for the separation and/or segregation of media. Such features may include but are not limited to centrifugal separation, centripetal segregation, filtration, electrophoresis, ionic separation, dipole segregation, membrane separation, permeation, percolation, leaching, diffusion and pervasion. Those skilled in the art will recognize that other conceivable features or methods, chosen with sound engineering judgment, may be incorporated in the 3MD device 100 to allow for the separation and/or segregation of media.

Figure 19:
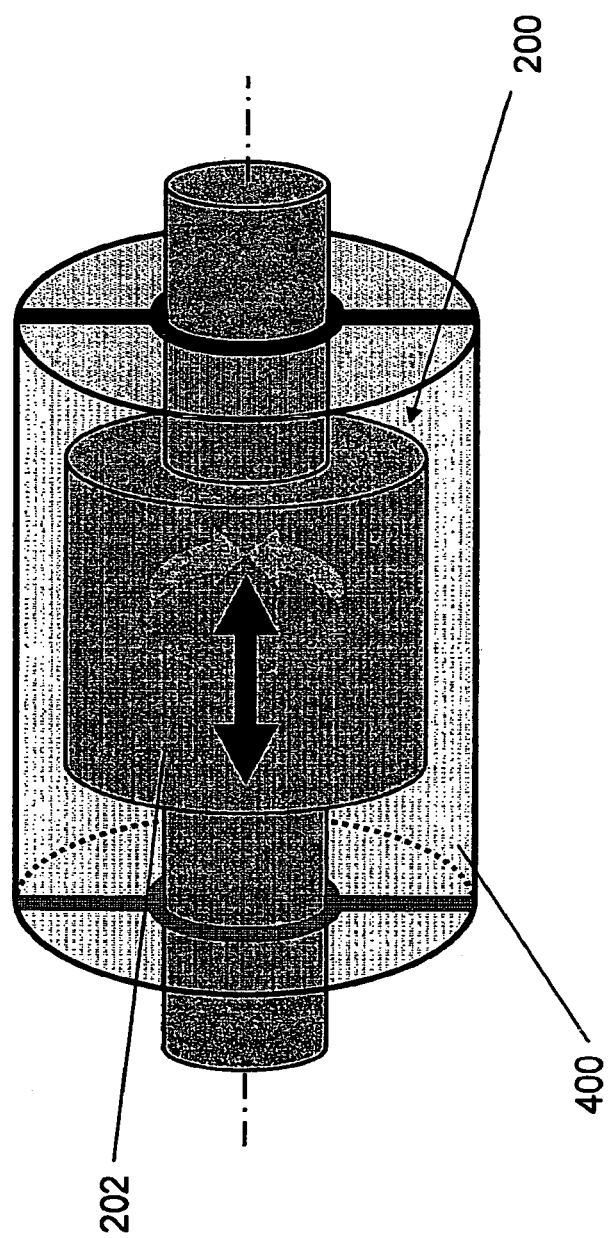
FIG. 19 is a module of a modular magneto-mechanical device according to one embodiment of the invention.
Figure 20:
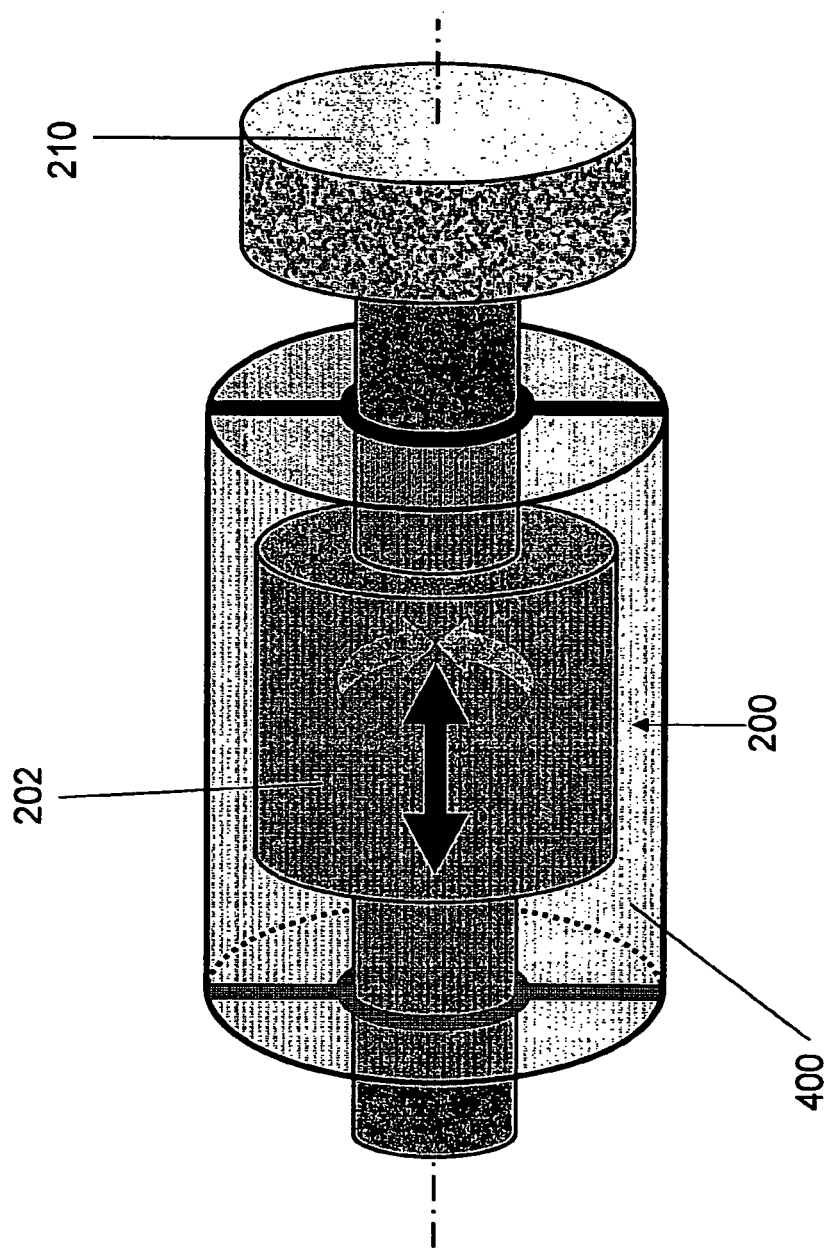
FIG. 20 is a module of a modular magneto-mechanical device according to one embodiment of the invention.

With reference now to FIGS. 19-20, in addition to the aforementioned 3MD device 100 embodiments involving a rotating spindle 202, a 3MD device 100 utilizing the same fundamental principles of operation can also accommodate linear motions of a magnetically charged or electromagnetically responsive movable element driven by an externally generated electromagnetic field, as depicted in FIG. 19. In this manner, a 3MD device 100 can allow for controlled axial displacements and/or rotation of the spindle 202 during its operation. In addition to the spindle 202 embodiments previously described, as illustrated in FIG. 20, one or both ends of the 3MD spindle 202 can be configured to accommodate a means for material removal or displacement 210, chosen with sound engineering judgment, which may include but is not limited to drill bits, grinding assemblies, pulverizers, reamers, honers, sanders, abraders, scrapers, brushes, scrubbers, buffers, cutters, and saws. Alternatively, one or both ends of the 3MD spindle 202 can be configured with a means for material transfer, chosen with sound engineering judgment, such as a hollow injector/extractor needle head or other such material transfer device. Those skilled in the art will recognize that the spindle 202 may comprise other conceivable features, chosen with sound engineering judgment, that may be incorporated in the 3MD device 100 to allow for axial displacements and/or the removal, displacement, or transfer of material.

With reference now to all the FIGURES, further to the previously described embodiments, a 3MD device 100 may be accommodated with one or more mechanical coupling means which may include but is not limited to direct drive couplings, drive shaft couplings, flexible couplings, universal joint couplings, intermeshing gears, gear boxes, worm drives, chain drives, belt drives, and magnetic coupling drives for the purposes of driving the motion of one or more mechanical or electromechanical devices. Those skilled in the art will recognize that other conceivable mechanical coupling means, chosen with sound engineering judgment, may be incorporated in the 3MD device 100 to allow for the driving of motion of one or more coupled devices.

With reference now to FIGS. 21-23, in another embodiment of the invention, the linear and/or rotational motion of the first magnet 201 of the rotor 200 that may be housed within the 3MD spindle 202 may be used to induce an electrical current in conductive coils 209 adjacent to the 3MD module 400 that may or may not be integrated with the module 400. Hence, motion of the 3MD spindle 202 may be used to generate electrical power within electromagnetic induction coils 209, thereby functioning as a 3MD electric power generator device 103. In one embodiment of the invention, the induction coils 209 may be external to or the 3MD module 400 and the 3MD device 100 may perform any of the previously described functional operations. In another embodiment of the invention, the induction coils 209 may be positioned on the module 400. Depending on the arrangement of the first magnet element 201 and the electromagnetic coils 209 comprising the 3MD generator device 103, said 3MD generator device 103 may be configured to generate either direct or alternating currents of electricity. In this manner, the electricity generated during operation of the 3MD generator device 103 can be used to provide energy to one or a multitude of electrical devices located external to said 3MD module 400 or housed within or in close proximity to the 3MD module 400. Said electrical devices may include but are not limited to batteries, capacitors, power storage devices, power conduits, transformers, power converters, rechargers, computer microchips, sensors, detectors, chemical analyzers, transmitters, receivers, wireless communication devices, LEDs, cameras, optical visualization devices, infrared imaging devices, lasers, thermoelectric devices, tachometers, electromechanical actuators, ultrasonic actuators, and other such electrical devices. In another embodiment of the invention, the 3MD module 400 may be configured with electrodes that may be used to provide electrical impulses to a specific electrical device or local environment in close proximity to the 3MD electrodes. Those skilled in the art will recognize that other conceivable inductance means, chosen with sound engineering judgment, may be incorporated in the 3MD device 100 to allow for the external and/or onboard generation of electricity to power any conceivable type and number of electrical devices or application coupled with the 3MD module 400.

All of the aforementioned 3MD device 100 embodiments may also be made to be portable devices capable of locomotion either through self propulsion or by an external motion means. Furthermore, with any of the embodiments previously described, all of the 3MD module 400 components and the control assembly 500 may be constructed of any combination of polymeric, metallic, ceramic, organic, and/or inorganic materials. Additionally, all of the aforementioned and hereafter described 3MD device 100 embodiments may be configured with any number of surface coatings or treatments in order to biologically, chemically or physically compatibilize, protect, or otherwise facilitate the operation of said 3MD device 100 within a given environment.

Figure 27:
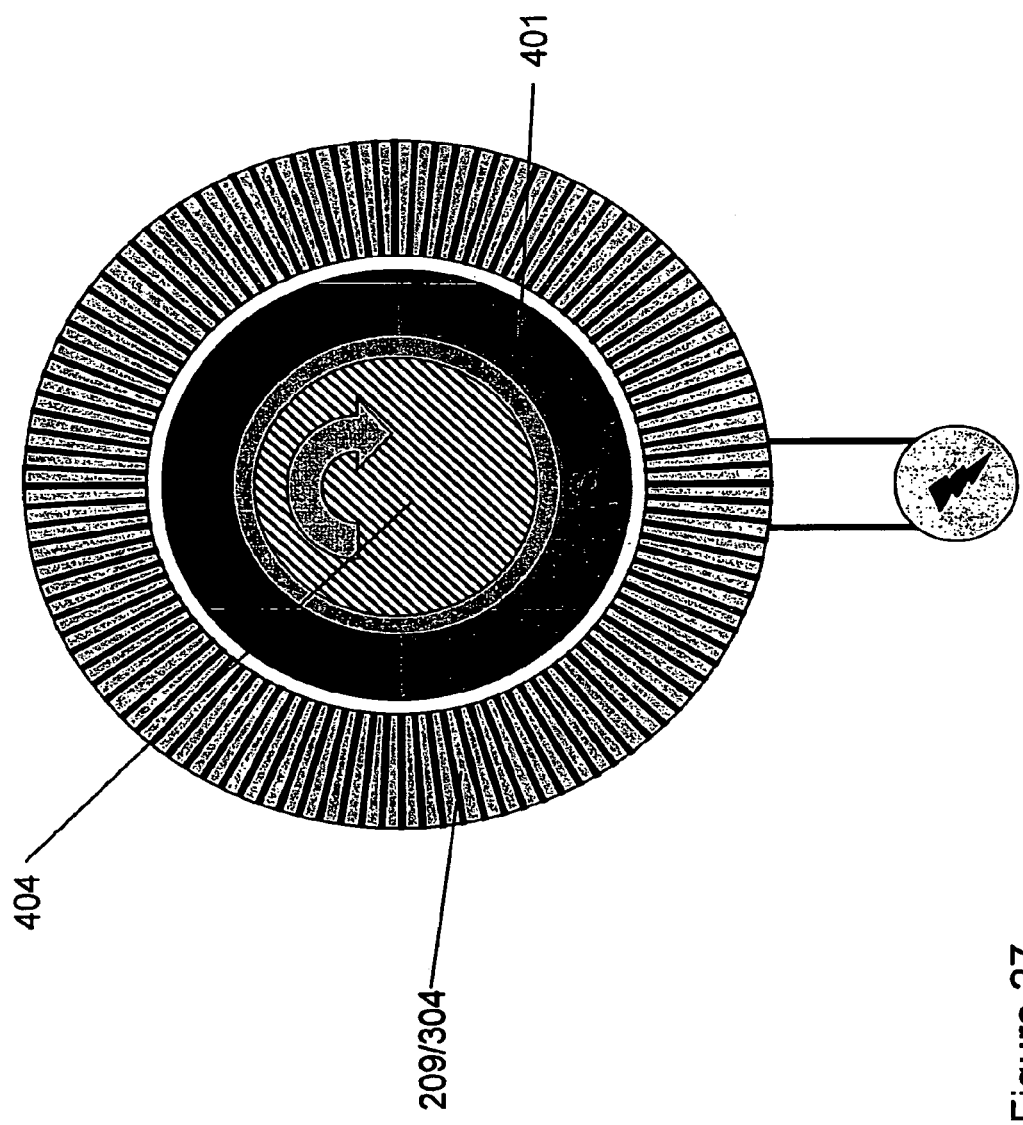
FIG. 27 is a 3MD module having a sleeve configuration according to one embodiment of the invention.

With reference now to FIG. 27, in yet another embodiment, a 3MD device 100 can be comprised of a magnetic sleeve 401 containing one or more permanent magnet elements 402 that can be attached to any beam member or shaft 404 capable of rotation and/or linear motion already having one or more bearing means associated therewith and that is enveloped by one or more electromagnetic coils 209. In a similar manner as previously described, the magnetic field generated, by the electromagnet coil(s) 209 and a controllable electrical current source 305 may be used to either attract or repel the respective magnetic poles of the magnetic sleeve 401, thus driving motion of the magnetic sleeve 401 and the beam member 404 attached therein. When operated in a passive mode, motion of the beam member 404 causes the motion of the attached magnetic sleeve 401 such that an electrical current is induced in the enveloping electromagnetic coil(s) 209. Hence, in said manner motion or electrical power can be generated by said 3MD device 100 with no further frictional contribution or losses associated therewith to the moving shaft assembly 404. Those skilled in the art will recognize that other conceivable variations of said embodiment may exist.

Figure 24:
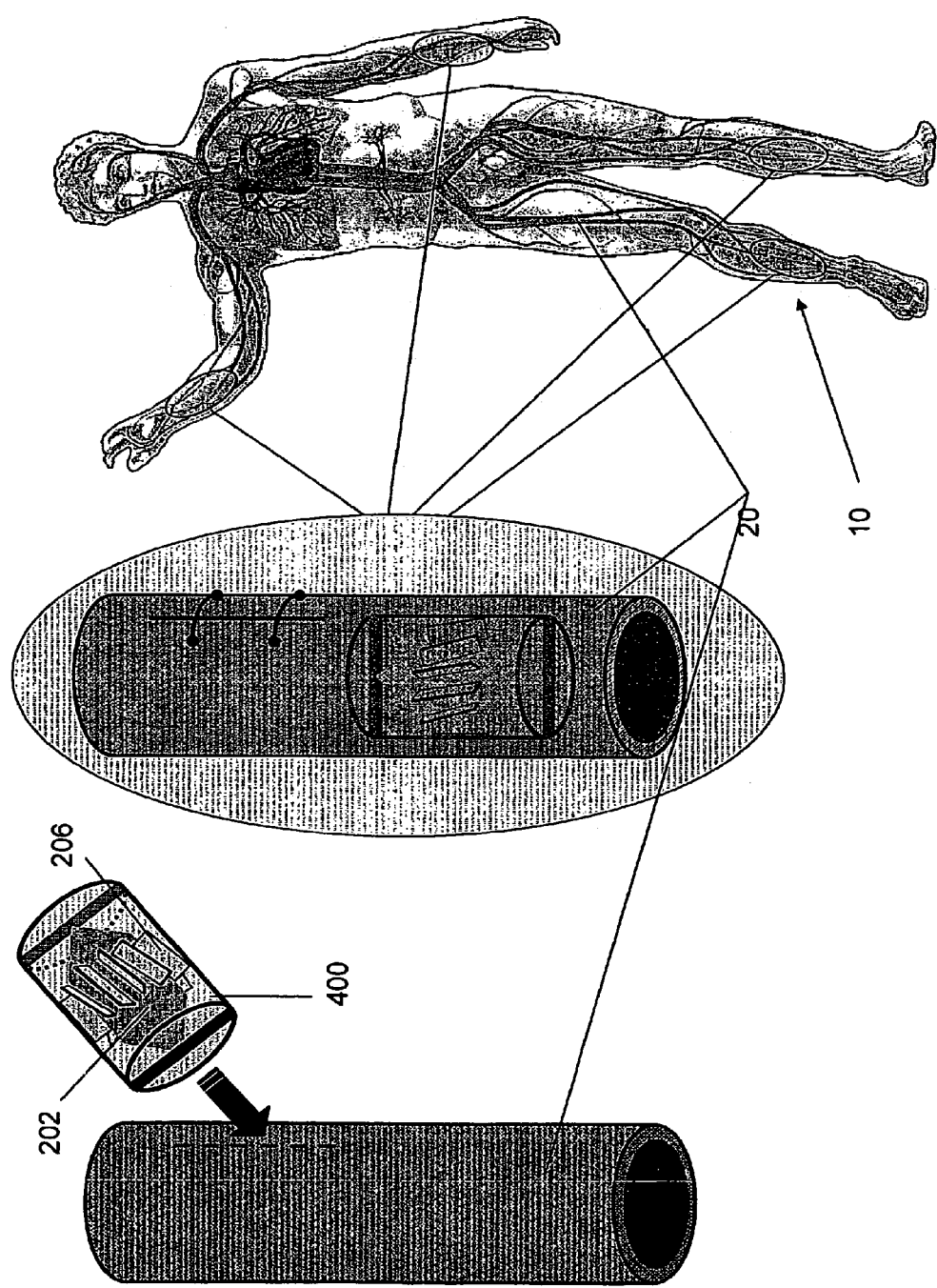
FIG. 24 is a module of a modular magneto-mechanical device implanted within the human body according to one embodiment of the invention.
Figure 25:
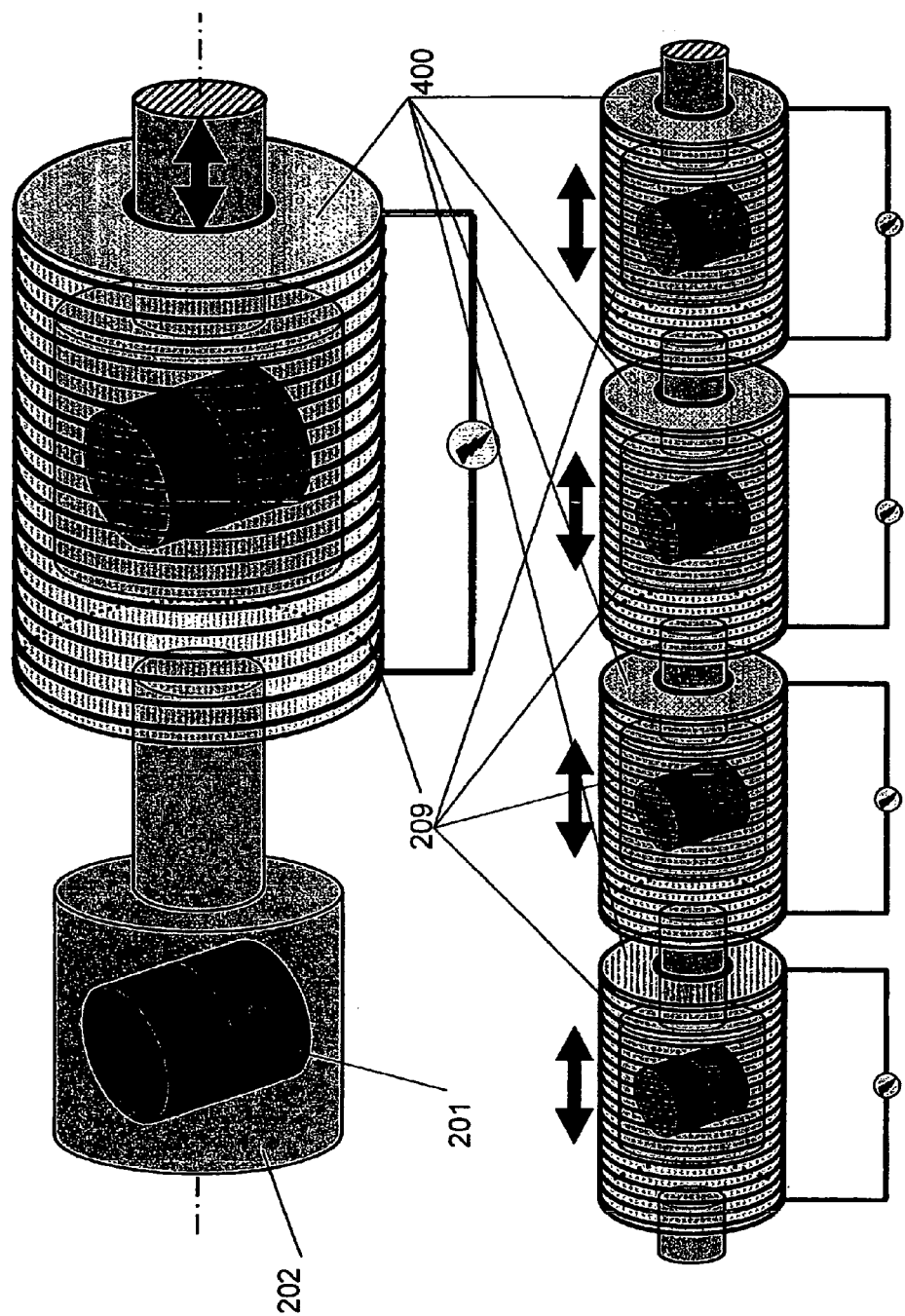
FIG. 25 is a modular magneto-mechanical device that has a plurality of modules according to one embodiment of the invention.
Figure 26:
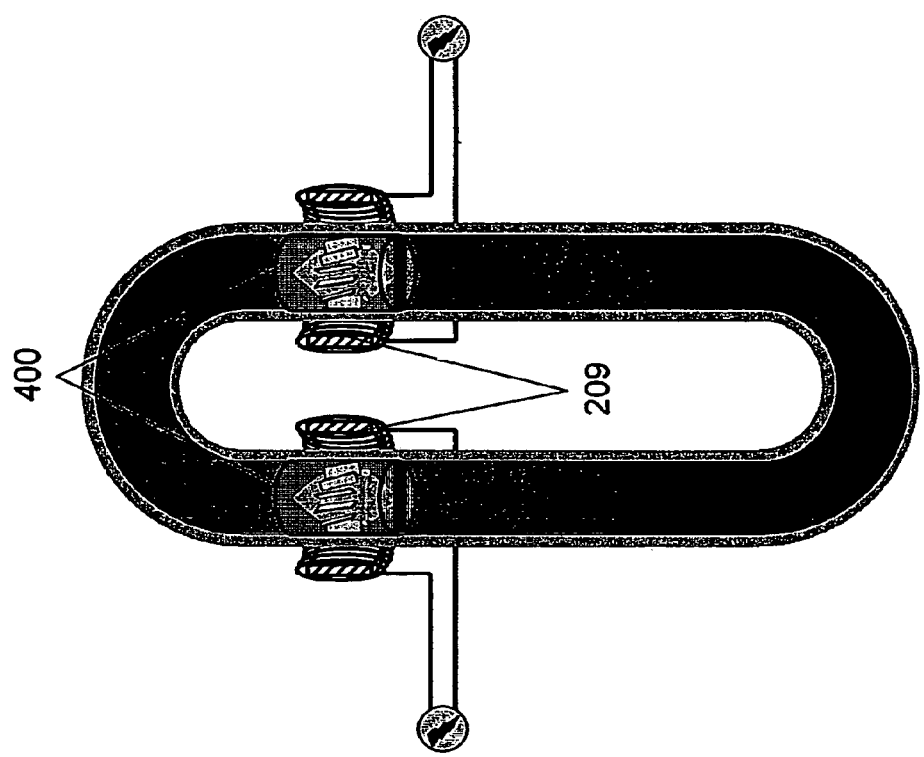
FIG. 26 is a modular magneto-mechanical device that has a plurality of modules according to another embodiment of the invention.

With reference now to FIGS. 24-26, individual 3MD devices 100 may be used singly, in series (as shown in FIG. 25), in parallel (as shown in FIG. 26) or in combinations therewith to define a system or array of 3MD devices 100. Each individual 3MD device 100 may be tasked to perform a single or multitude of functions that may be controlled independently, in tandem, or in multiple combinations to comprise an integrated workflow and/or networked control process.

Invention Utility, Applications, and Differentiation Over Related Art

In general, 3MD technology can be immersed and utilized in any type of environment for any application requiring or well-suited for wireless motor technology or in which the driving means and the functional operation means can be wholly integrated into a single device. Although various applications relating to the utilization of 3MD technology are described below, those skilled in the art will recognize that other conceivable applications of 3MD technology may exist that are not described herein.

Biomedical—Internal Electrical Power Generation

With reference now to FIGS. 21, 24, 26, and 28, in one embodiment of the invention, in addition to the onboard electrical power generation as previously described during 3MD operation, when utilized in a passive mode an implantable 3MD device 100 may serve the role of an electrical power generator or 3MD generator device 103. A 3MD module 400 configured with onboard electromagnetic coils 209 may be implanted in a blood vessel 20 such that the flow of blood passing through the 3MD module 400 may drive the motion of the magnetic 3MD spindle 202 thereby generating an electrical current in the adjacent housing coils 209. In this manner, said 3MD generator devices 103 can be used to generate power for other electrical devices implanted in the human body 10.

Figure 28:
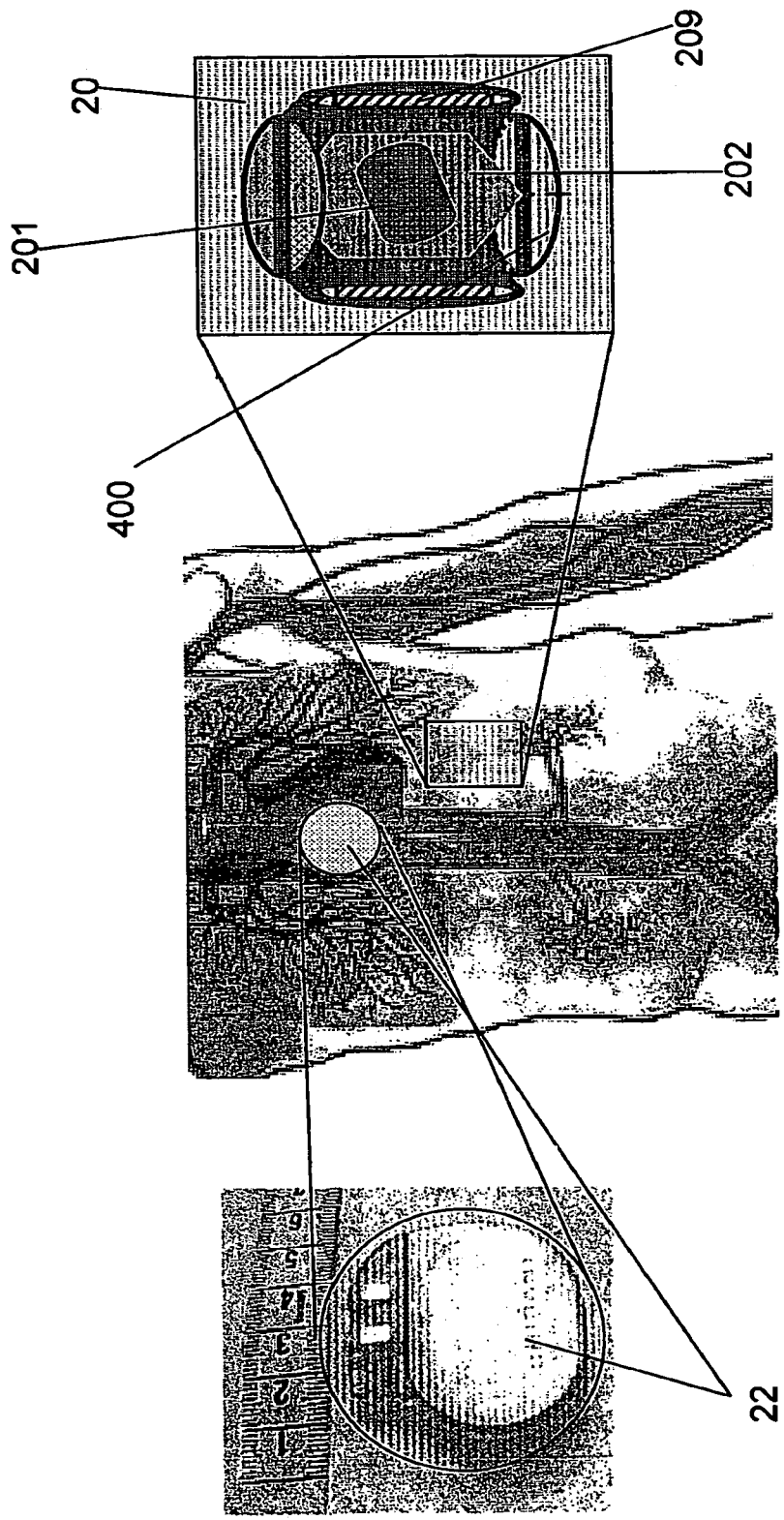
FIG. 28 is a 3MD module inserted into a cardiovascular system according to one embodiment of the invention.

With reference now to FIGS. 24, 28-30, in one embodiment of the invention, a 3MD generator device 103 may comprise the 3MD device 100 coupled to an implantable 3MD electrical power generator device 103 wherein the 3MD device 100 may be used as the driving means for the coupled implantable 3MD electrical power generator device 103. In this manner, the module 400 may comprise a hermetically sealed container and may be implanted in a human body 10. The motion of the 3MD module 400 may then be wirelessly driven by the control assembly 500 that is external to the human body as previously described. The module 400 may subsequently provide the driving motion for an electromechanical power generator device coupled to the 3MD module 400 that may then serve as an electrical power source for other implantable electrical devices 22 within the human body (as shown in FIG. 28). Said 3MD generator device 103 may be located anywhere within the body cavity such that it or a multitude of 3MD generator devices 103 could provide electrical power to any number of implanted electrical devices such as artificial organs, artificial muscle tissue, electromechanical devices, thermoelectric devices, imaging devices, chemical detection and analysis devices, sensors and other classes of detection devices.

Figure 30:
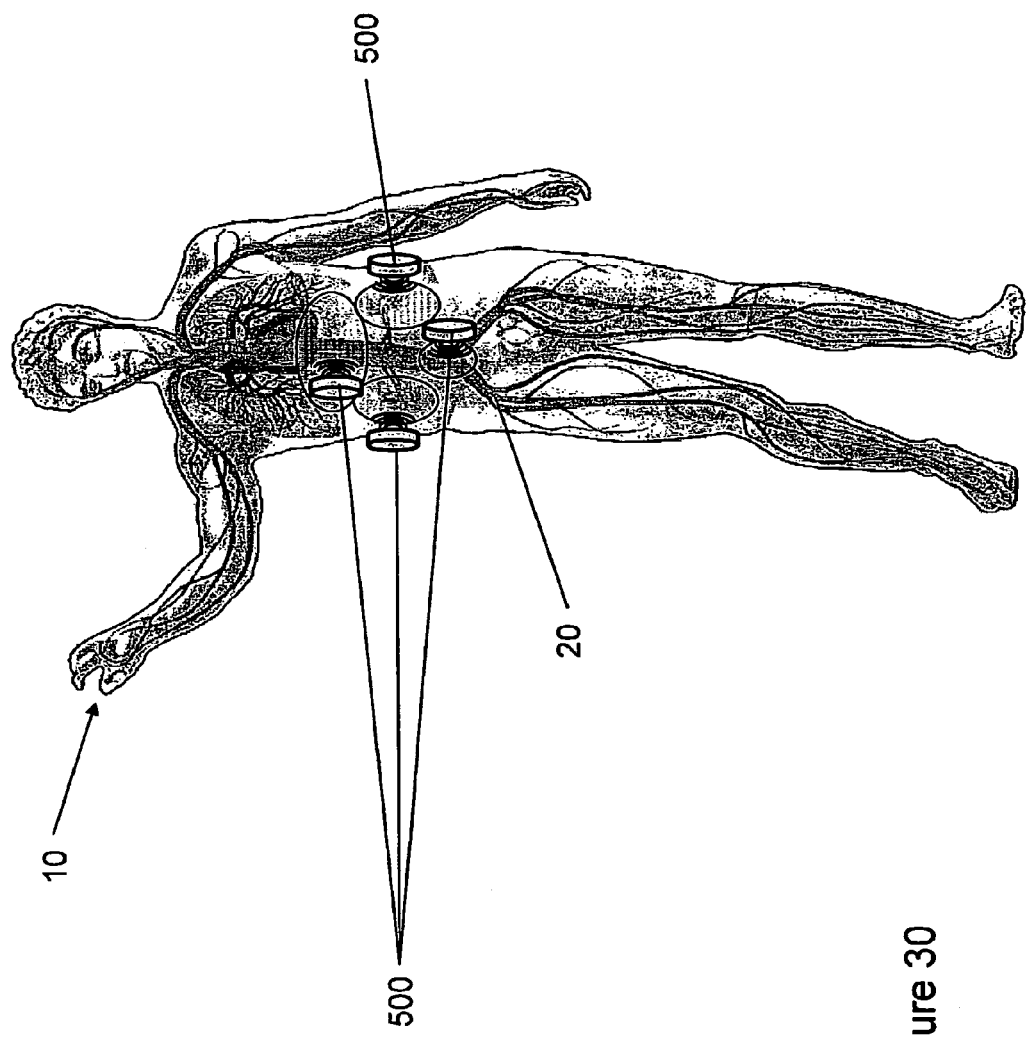
FIG. 30 is a modular magneto-mechanical device according to one embodiment of the invention.

With reference now to FIGS. 24, 28, and 30, in another embodiment of the invention, the 3MD generator device 103 may be used to provide electrical power to implantable 3MD device control assemblies 500 that can be utilized locally within the body for 3MD applications where proximal external access to an implanted 3MD module 400 may not be possible or the lack thereof may present difficulties with regard to control and performance of the 3MD device 100. In this manner, the control assembly 500 may be hermetically sealed and may be implanted within the body. The control assembly 500 may be directly situated outside the tissue, organ, or vessel wall where the 3MD module 400 may be implanted. Furthermore, in another embodiment of the invention, said implantable 3MD device control assemblies 500 may be used as a slave or intermediate controller by incorporating a wireless communication device such that it can communicate and be subsequently controlled by a master controller device external to the human body. These 3MD electrical power generation applications can also be applied for use with other mammals and animals. Those skilled in the art will recognize that other conceivable 3MD applications not described herein may also be implemented with regard to internal electrical power generation operations.

Biomedical—Circulatory System Applications

Figure 29:
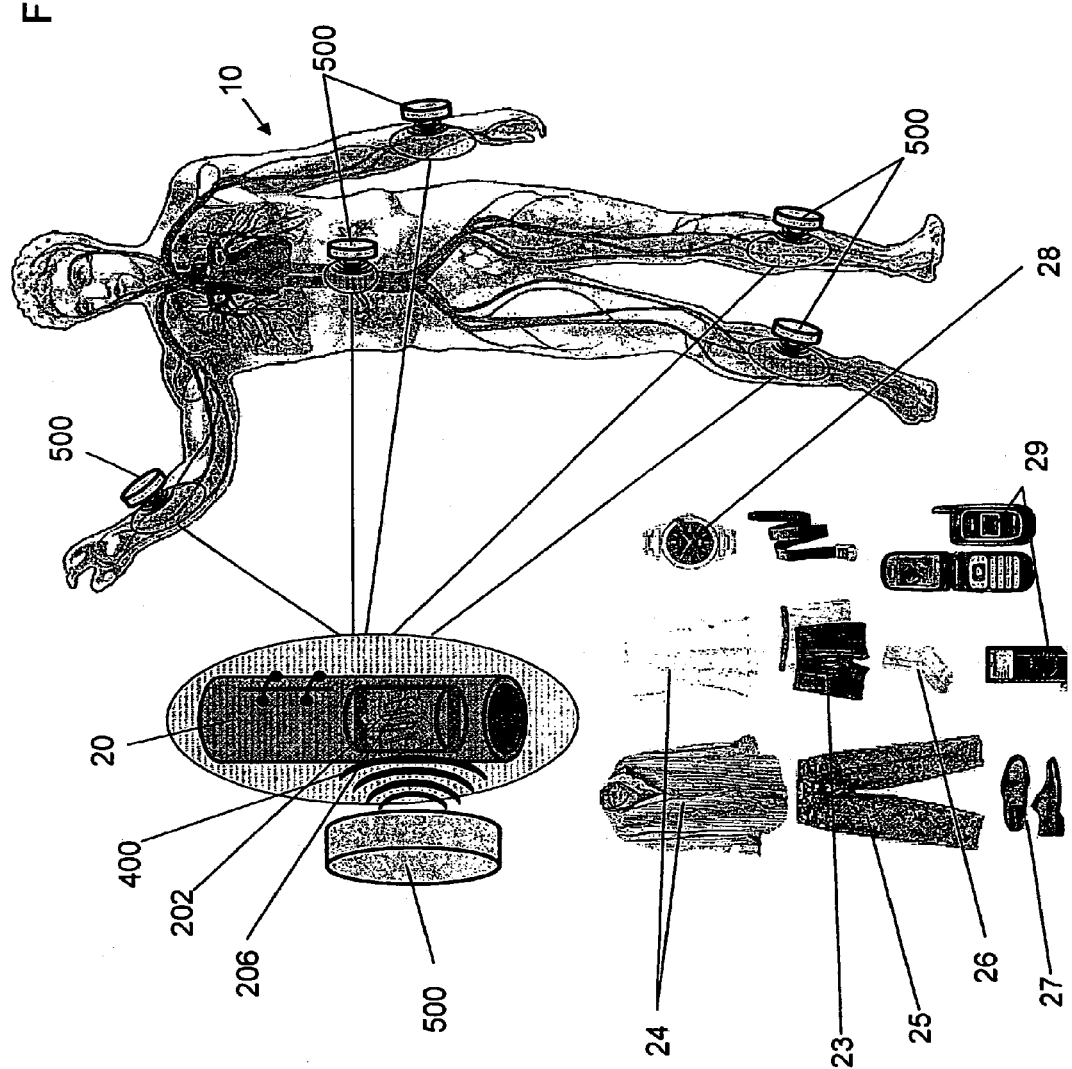
FIG. 29 is a modular magneto-mechanical device having a portable control assembly according to one embodiment of the invention.

With reference now to FIGS. 24, 28-29, the object of the present invention, according to one embodiment of the invention, relates to a technology that can be used in the human circulatory system for the purposes of defining a flow network that may employ the practice of staged pumping throughout the human body. One or more of the said 3MD devices 100 may be implanted within the vast numbers of blood vessels and passageways defining the human circulatory system. In this manner, instead of completely replacing the natural human heart, 3MD devices 100 may be used to precisely regulate blood flow and pressure throughout the body and supplement weakened or overexerted cardiac activity thereby reducing the stress and demands that would otherwise be borne solely by the heart with symptomatic manifestations of high or low blood pressure and/or poor blood circulation. In the event of cardiac arrest, a 3MD device 100 network could also assume the role of artificial heart function thereby maintaining operation of the circulatory system in the absence of natural heart activity. And while other artificial heart devices described in the prior art require the contrastive joining of a synthetic portal to biological tissue to seal the flow system, with a simple incision a 3MD module 400 can be inserted and wholly contained within a blood vessel thus obviating the need for sealing joints or unions and all of the potential leakage, infection, tissue rejection, and other such biological incompatibility issues associated therewith, as depicted in FIG. 24. Furthermore, unlike other artificial heart technologies that require either an implantable battery or a hardwire connection to a power source external to the body, the 3MD device 100 operates via wireless motor technology obviating the need for dermic seals or subsequent surgery for internal battery replacement.

With reference now to FIGS. 7, 24, 28-29, according to one embodiment of the invention, when operated in a passive mode, a 3MD device 100 can also serve the role of a blood flow meter. By actively monitoring 3MD spindle 202 motion and/or orientation as the spindle 202 react to the flow of blood passing through the 3MD module 400, volumetric blood flow rate can be precisely determined by the external 3MD control assembly 500. As well when operated in this passive mode, the motion of the magnetic 3MD spindle 202 may be used to induce an electrical current in the adjacent conductive coils 306 of the external 3MD control assembly 500 either to generate electrical power as previously described or to produce a coil current relative to spindle rotation as a measure of volumetric flow rate. In this manner, said 3MD devices 100 can be used to actively monitor blood flow rates locally within the body and responsively regulate the flow of blood accordingly throughout the 3MD flow network.

With continued reference to FIGS. 7, 24, 28-29, according to one embodiment of the invention, the 3MD device 100 may also be used in specific isolated regions of the human body where poor blood circulation exists and/or regulated blood circulation is especially required. Afflictions causing poor blood circulation such as diabetes can often affect blood flow to the body's appendages and extremities such as the arms, hands, legs and feet, which represent the longest pathways to and from the heart. In such cases, the 3MD device 100 can be specifically located in the extremities where they are most needed to regulate the flow of blood. Said 3MD device 100 may also be utilized to precisely regulate blood flow and pressure in sections of blood vessels and circulatory passageways that may be weakened due to wall thinning or scarring and may otherwise be susceptible to aneurisms and/or rupture. Strategically positioned 3MD devices 100 within a 3MD flow network can also be used to divert blood flow from a specific bodily region or organ as in the case of internal hemorrhaging or to increase or controllably regulate blood flow to a distinct location, tissue or organ within the body. In this manner, 3MD technology can be used to increase or regulate blood flow to specifically stimulate certain organ or tissue operation such as with neural and/or muscular activities or to facilitate and/or stimulate biological recovery of organs and tissues from injury or bodily damage. In addition, said 3MD device 100 may also be configured to serve the function of a stent device used to prevent or counteract a disease-induced localized flow constriction within a blood vessel or other biological duct.

With continued reference to FIGS. 7, 24, 28-29, 3MD devices 100 can also be used in specific isolated regions of the human body where blood vessels may be susceptible to blood clots and/or wall plaque residue and accumulation. Because of the unique multi-function capabilities of 3MD technology, not only can said devices be used to regulate flow in restricted passageways and vessels where a high-probability of clogging exists, they can also be used to remove, dissipate, break apart, or pulverize potentially harmful wall plaque and/or other clogging media present in blood passageways. In this manner, clots and vessel clogging media can be dramatically reduced in size with the use of 3MD modules 400 strategically located throughout the flow network thus minimizing and/or negating their potentially harmful impact on the rest of the circulatory system and vital organs of the body. For example, 3MD devices 100 may be strategically placed in blood vessels leading to the brain thereby reducing the probability for neural blood clots and the potentially devastating risk of strokes associated therewith. Such 3MD applications offer a significant alternative to the more conventional use of chemical blood thinners often prescribed to patients suffering from these afflictions and all of the adverse side effects often associated with said chemicals and drugs.

With continued reference to FIGS. 7, 24, 28-29, furthermore, according to one embodiment of the invention, the 3MD module 400 may be configured to generate onboard electricity as previously described that can be used to power any number of integrated electrical sensors and devices for the purposes of interactive flow regulation of the blood. Applications for said 3MD coupled electrical devices may include but are not limited to the local monitoring of blood pressure and flow conditions, the visualization of internal blood vessels for the purposes of diagnosing and aiding in the treatment of flow restrictions within specific regions of the body, wireless communication with the external 3MD device control assembly 500, and supplementary techniques for the treatment of said blood vessel flow restrictions such as laser removal and ultrasonic disintegration of the clogging media. The resultant signals from the 3MD coupled electrical sensing devices can be wirelessly transmitted from inside the body to the external 3MD control assembly 500 for interactive feedback loop control of the 3MD flow regulation process and/or the responsorial actions to targeted flow restrictions. In this manner, these interactive 3MD (hereinafter "i-3MD") flow regulation devices 104 may be used to actively monitor the flow conditions and/or restrictions present within a certain location of the body, interactively respond to said flow conditions and restrictions, and controllably regulate blood flow throughout the 3MD flow network.

The i-3MD technology just described that incorporates onboard electrical power generation integrated and/or coupled with onboard electrical devices may also be used in any and all of the 3MD applications previously and hereafter disclosed for interactive control during operation of a 3MD workflow. Hereafter, the term 3MD will encompass all references to the object of the present invention including any specific references to the subclass of i-3MD devices.

With reference now to FIGS. 24, 28-29, according to one embodiment of the invention, the 3MD devices 100 may also be configured to operate as online blood viscosity and rheology sensors. The electromagnetic force required to cause the motion of the 3MD spindle 202 can either be precisely controlled for stress controlled rheological measurements or precisely measured for rate controlled rheological measurements. In this manner, blood viscosity and rheology can be continually or periodically monitored as a function of applied deformation rate and/or applied stress in-situ to the human body in order to assess physical blood condition and/or the well being of the human circulatory system. With the 3MD modules 400 also configured to generate onboard electricity, 3MD rheology sensor devices can also be integrated with any number of wireless communication devices, electrical sensors, chemical analyzers and other such analytical sensing devices for the purposes of providing a more comprehensive blood analysis for in-situ assessment of chemical and physical blood condition and/or patient well being. In addition to all of the aforementioned internal circulatory system applications, a network of mobile 3MD modules 400 can be made to interactively respond to situations affecting the circulatory system by traveling to specific locations within the body and performing a multitude of controllable functions depending on the circumstances of each situation. In this manner, mobile 3MD modules 400 can be used to "patrol" all or certain "corridors" of the human body traveling within the vast complex of blood vessels while controllably responding to circulatory system stimuli and their respective regulatory requirements.

With reference now to FIGS. 7, 18, 24, 28-29, any of the 3MD circulatory system applications previously described can be used as permanent, replaceable, or disposable devices for implantation within the human body. Any of these devices can also be configured with adjustable spindle and/or rotor elements and topographical features 206 that can be controllably manipulated during operation in order to precisely regulate flow, compression ratio, and/or material removal as flow network and system demands change. As well, the 3MD modules 400 comprising the flow networks previously described can be tasked individually such that each module can perform a multitude of functions and operations either collaboratively or independently from the other modules during network operation. With regard to throughput in the flow network, the 3MD modules 400 can be made to operate in synchronization with the pulsations of heart-generated flow, in a mode of continuous steady flow, or in any variable combination of flows associated therewith.

With reference now to FIG. 29, according to one embodiment of the invention, operation of the aforementioned implantable 3MD devices 100 may be controlled by portable control assemblies 500 located in close proximity outside the human body. In this manner, specific 3MD control assembly 500 can be placed directly on or close to the skin or integrated with articles of clothing such as undergarments 23, hats (not shown), shirts 24, pants 25, vests (not shown), gloves (not shown), socks 26, and shoes 27 or fashion accessories 28 such as masks, bracelets, anklets, necklaces, pendants, buttons, jewelry, belts, bands, watches, key chains, mobile telecommunication and personal electronic devices 29 such that the control assembly 500 is situated in close proximity to the 3MD module 400 that is being wirelessly operated.

Figure 34:
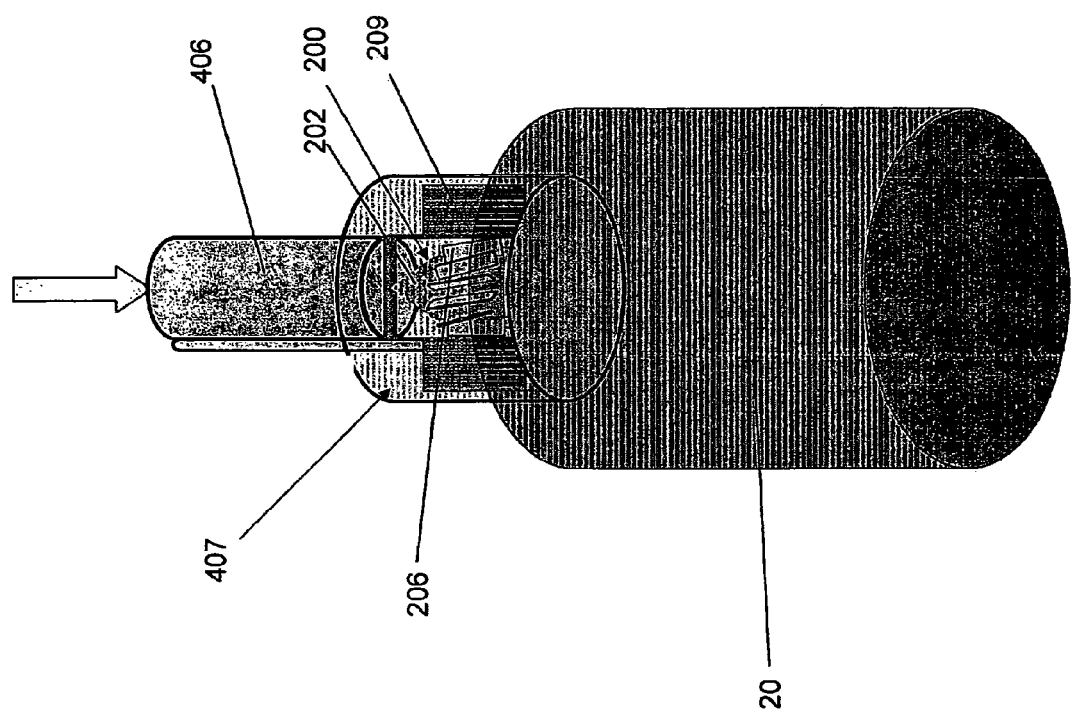
FIG. 34 is a modular magneto-mechanical device module according to one embodiment of the invention.
Figure 35:
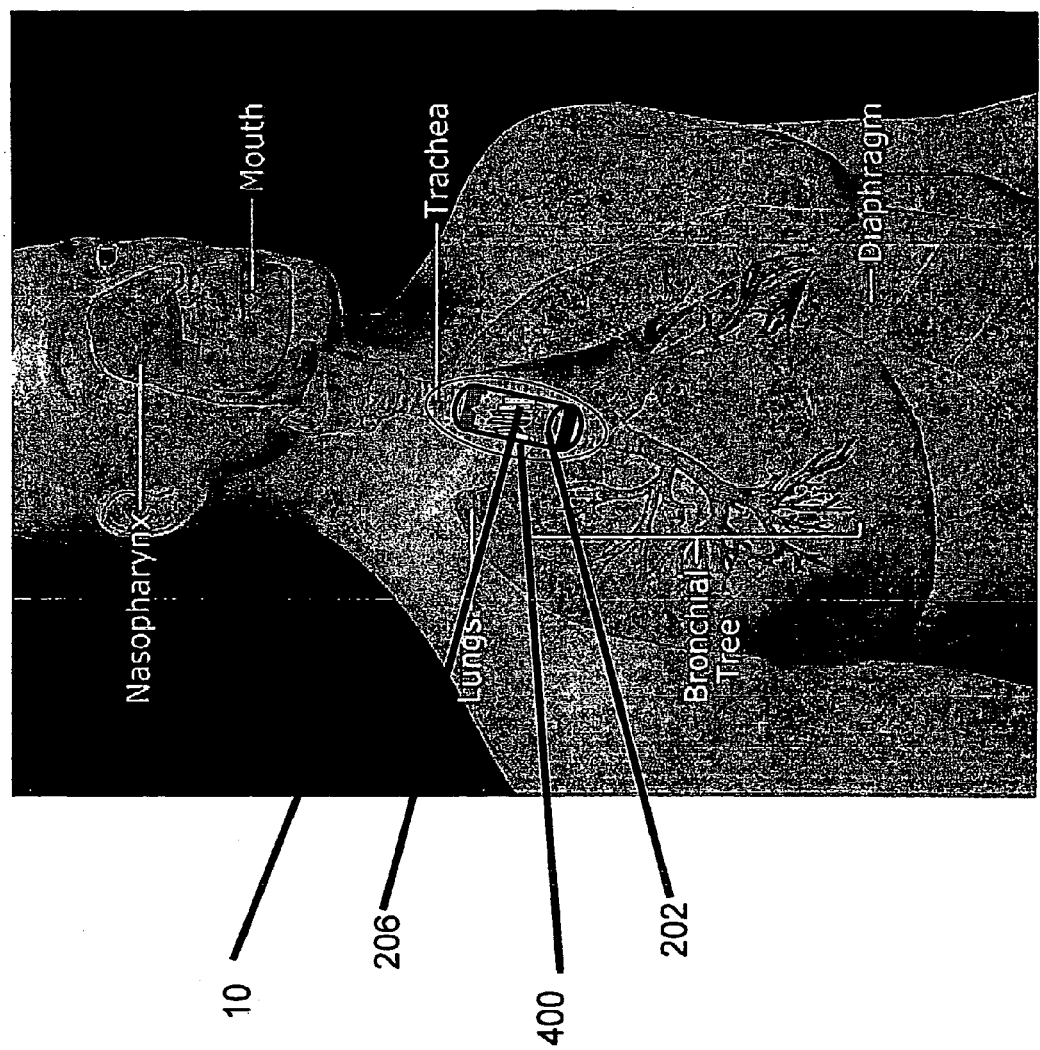
FIG. 35 is a modular magneto-mechanical device module according to one embodiment of the invention.

Although all of the above circulatory system applications describe the use of implantable devices, 3MD technology can also be used in external circulatory system operations and applications such as in blood extraction and transfusion devices, blood circulators and pumps, and other such blood conveying devices. In this manner, 3MD pumping devices 105 offer a significant advantage over existing external blood pumping devices in that pump seals that act to contain the blood and sequester it from the electrical driving means and which constantly run the risk of bio-hazardous contamination are not required. As well, 3MD rheology sensing devices 113 can also be used in conjunction with blood circulators and medical syringes for the online assessment of blood condition during the blood circulation or extraction process. Furthermore, while the 3MD control assembly 500 may be implemented as a permanent hermetically sealed device or apparatus, the 3MD modules 400 can be utilized in the form of easily replaceable cartridge attachments (as shown in FIG. 34) that can be sterilized for subsequent reuse or disposed of with other bio-hazardous waste materials. Further, any of the above 3MD applications can also be applied to the circulatory system operations of other mammals, animals, or other biological organisms containing a circulatory system. Those skilled in the art will recognize that other conceivable 3MD applications not described herein may also be implemented with regard to any circulatory system operations.

Biomedical—Blood Filtration Applications

Liver and kidney disease are serious biological disorders that can severely deteriorate the body's ability to metabolize proteins, carbohydrates, and fats, detoxify poisonous substances, and filter the blood. As a consequence of such disease, the liver and/or kidneys operate in a progressively weakened state increasingly unable to, in the case of the liver, neutralize toxins and metabolize complex fats and carbohydrates present in the blood or in the case of the kidneys, filter the blood before the organs ultimately fail. Although these disorders are conventionally treated with specialty prescription medications and diet modification, depending on the state of disease such treatments are often ineffective and/or the prescribed medication has adverse side effects on the rest of the human body.

Figure 31:
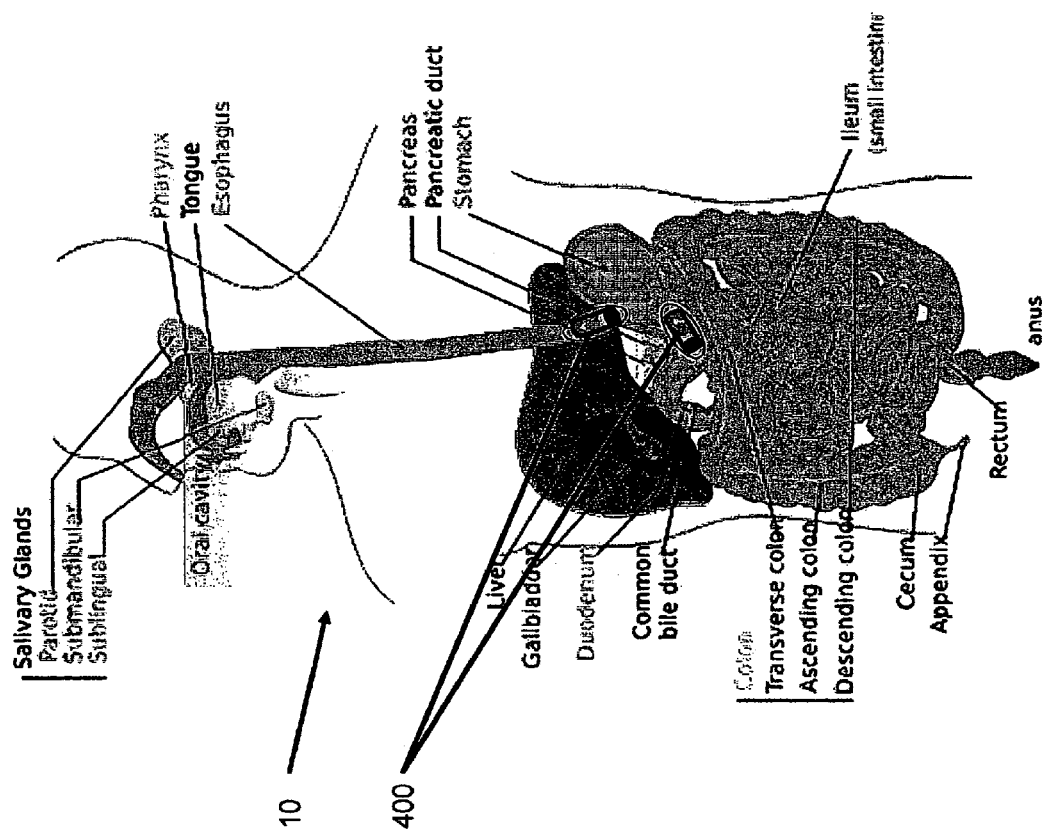
FIG. 31 is a modular magneto-mechanical device according to one embodiment of the invention.
Figure 32:
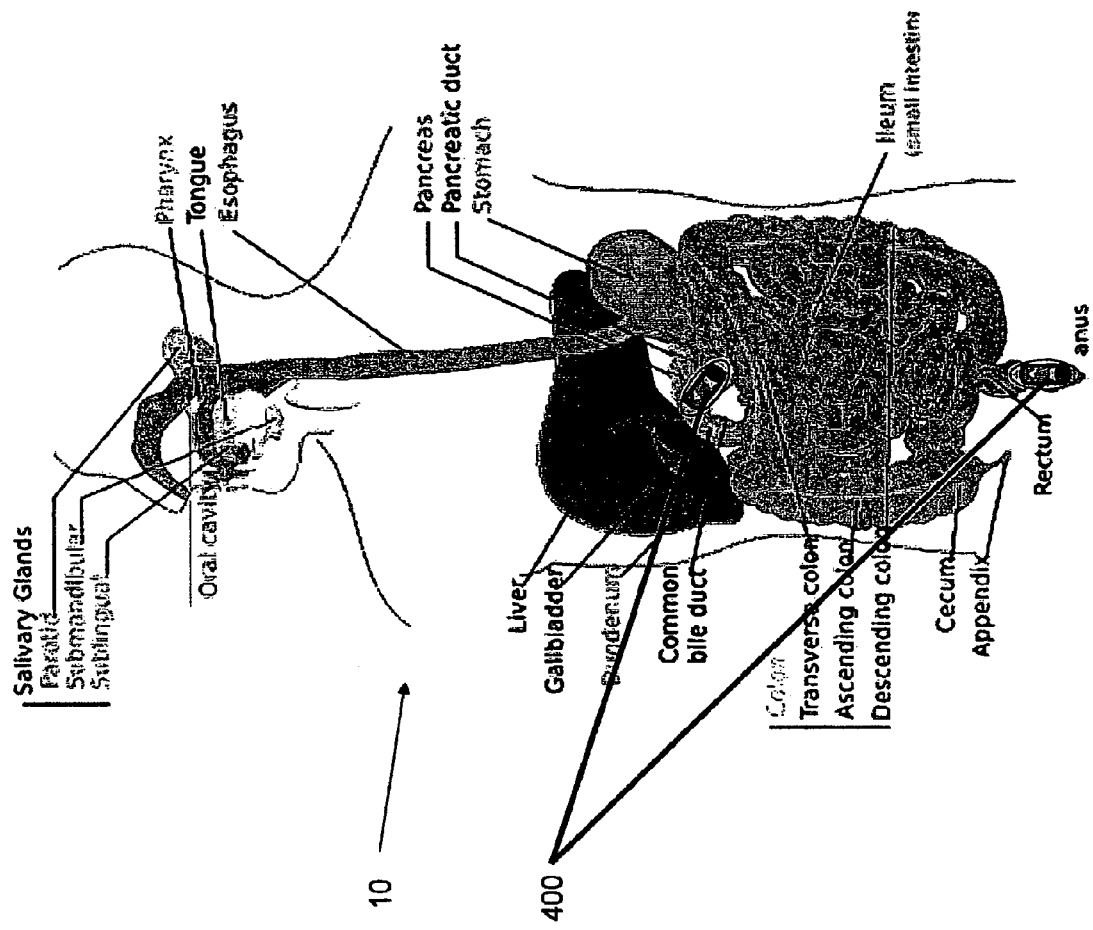
FIG. 32 is a modular magneto-mechanical device according to one embodiment of the invention.

With reference to FIGS. 30-32, according to one embodiment of the invention, as an alternative to conventional drug treatment, the implantable 3MD device 100 may be incorporated in the body to act as a 3MD filtration device 106 capable of separating fats, toxins, and waste material from the blood prior to entering the liver and/or the kidneys. The 3MD module 400 may be configured to controllably extract undesirable substances from the blood in order to reduce the burden otherwise borne by these organs. According to another embodiment of the invention, a 3MD pumping device 105 can be configured to serve as a fluid pressurizing means for a pressurized filtration device coupled with the 3MD module 400. The extracted substances can then be diverted and conveyed to either the bladder and/or lower intestinal tract to be naturally discharged with the rest of the body's waste materials. When coupled with an internal power source such as a 3MD onboard power generator 103, said 3MD filtration devices 106 would be able to employ mechanical separation techniques as well as electrophoresis and other electro-separation techniques in order to controllably extract undesirable substances from the blood. As well, multiple 3MD filtration devices 106 can be connected in series for the purpose of staged filtration in order to optimize the separation and/or extraction process. In addition, if after the filtration process the blood remains in a segregated or non-homogenized state, a 3MD mixing device 107 can subsequently be used in a finishing stage to re-homogenize the blood thus completing the filtration process. In certain cases, said 3MD filtration devices 106 could be configured to operate as an implantable artificial kidney in place of the natural organ.

Furthermore, said 3MD filtration devices 106 can be coupled with any number of implantable chemical analysis and detection devices for the purposes of interactive filtration and/or chemical separation of the blood. In this manner, said implantable chemical detection devices can be powered by an internal electrical power source such as a 3MD onboard power generator 103 and used to chemically screen the blood prior to and/or after the filtration or separation process. The response or resultant signals from said implanted chemical analysis and detection devices can then be wirelessly transmitted by an onboard wireless communication device to the external 3MD filtration device control assembly 500 for interactive feedback loop control of the 3MD filtration process. Said i-3MD filtration devices 106 could then be used to actively screen for certain biological and/or chemical substances such as toxins, fats, cholesterol, and other undesirable media that may be present in the blood and may be subsequently extracted, removed, sequestered, or destroyed by the 3MD filtration devices 106.

Cancer is a potentially devastating disease to all of humanity the treatments for which are often too late, painful and debilitating. As with almost any disease, early detection is critical and often times life saving. However, the origins of such manifestations are often difficult to track and not always readily accessible for exploration and/or monitoring by conventional means. Perhaps the biggest impact i-3MD filtration devices 106 can have with regard to biomedical applications is in the detection, monitoring, and sequestering of harmful cancer cells present within the human body. Similar to the mobile 3MD modules 400 previously described, mobile i-3MD filtration devices 106 can be used to interactively seek, extract, sequester, and/or destroy harmful cancer cells before they have a chance to spread and infest other vital organs or tissues throughout the body. Furthermore, a network of i-3MD filtration devices 106 can also serve as an artificial immune system used to detect and combat bacterial infections, viral infections and other devastating diseases such as AIDS and other pandemic afflictions that continually threaten humanity worldwide. Through continual online blood monitoring and screening throughout the human body, i-3MD technology can be pivotal in artificial immune system applications with regard to detecting and combating the onset of illnesses and diseases. Any of the 3MD filtration applications previously described can be used as permanent, replaceable, or disposable devices for implantation within the human body. Any of these devices can also be configured with adjustable spindle, meshes, and/or membrane elements and features that can be controllably manipulated during operation in order to precisely regulate filtration, separation, and extraction as filtration network and system demands change.

Although all of the above filtration applications describe the use of implantable devices, 3MD technology can also be used in external filtration, operations such as in kidney dialysis machines and other such biological filtration devices. In this manner, 3MD modules 400 offer an advantage over existing external pumping and pressurized filtration devices in that pump seals that act to contain the blood and sequester it from the electrical driving means and which constantly run the risk of bio-hazardous contamination are not required. Furthermore, while the 3MD control assembly 500 may be implemented as a permanent hermetically sealed device or apparatus, the 3MD modules 400 can be utilized in the form of easily replaceable pump and filtration cartridges that can be sterilized for subsequent reuse or disposed of with other bio-hazardous waste materials. Any of the above 3MD filtration applications can also be applied to the blood filtration operations of other mammals and animals. Those skilled in the art will recognize that other conceivable 3MD applications not described herein may also be implemented with regard to any blood filtration operations.

Biomedical—Respiratory System Applications

With reference now to FIGS. 14-16, 18, and 35, lung disease, lung injuries, and other pulmonary and/or respiratory disorders can severely affect a body's ability to respire and thus oxygenate the blood, and as a consequence medical patients requiring breathing assistance and/or pulmonary respirators are often times immobilized as a result of this incapacity for self-respiration. 3MD technology offers a distinct alternative to conventional externally mounted respiratory devices. 3MD modules 400 can be implanted in either the trachea or the bronchial tubes leading to the lungs to serve as artificial respirator devices. In this manner, 3MD respiratory devices 108 can be controlled by external control assemblies 500 and made to function as pumping devices capable of pumping air into and out of the lungs. This 3MD generated air flow can be made to operate in a reversible pumping manner as with conventional self-respiration or in a continuous coaxial multidirectional flow operation. As described previously, this latter 3MD pumping operation can be configured such that a hollow cylindrical 3MD spindle 202 containing rotors on its internal and external surfaces is housed within a hollow cylindrical conduit 207 thereby defining coaxial portals through which transportable media may be allowed to pass in opposing directions. Said internal and external spindle rotors or other independently movable elements 206 can be configured in an opposing flow manner such that rotation of the 3MD spindle 202 can generate coaxial flows driven in opposing directions. Hence, in this opposing coaxial flow configuration, fresh air can be pumped into the lungs and spent air expelled from the lungs with a steady continuous 3MD operation and state of lung inflation, thus obviating the need for repetitive lung inflation and deflation. Said continuous flow operation would be especially relevant to patients recovering from serious lung injuries where repeated inflation and deflation can often deter the healing and recovery process of the pulmonary tissue. Furthermore, unlike conventional respiratory assistance devices, an implantable 3MD respiratory device 108 would not render a patient immobile, allowing said patient to advance in the recovery and/or the subsequent rehabilitation process.

With continued reference to FIGS. 14-16, 18, and 35, the 3MD respiratory system applications just described can be used as permanent, replaceable, or disposable devices for implantation within the human body. Said 3MD respiratory devices 108 can also be used external to the body in place of or in addition to conventional externally mounted respiratory devices. As well, any of the aforementioned 3MD respiratory devices 108 can be configured with adjustable spindle and/or rotor elements and features 206 that can be controllably manipulated during operation in order to precisely regulate flow and compression ratio as flow network and system demands change. Furthermore, any of the above 3MD respiratory applications can also be applied to the respiratory system operations of other mammals and animals. Those skilled in the art will recognize that other conceivable 3MD applications not described herein may also be implemented with regard to any respiratory system operations.

Biomedical—Regulation, Stimulation and Dispensing Applications

Figure 36:
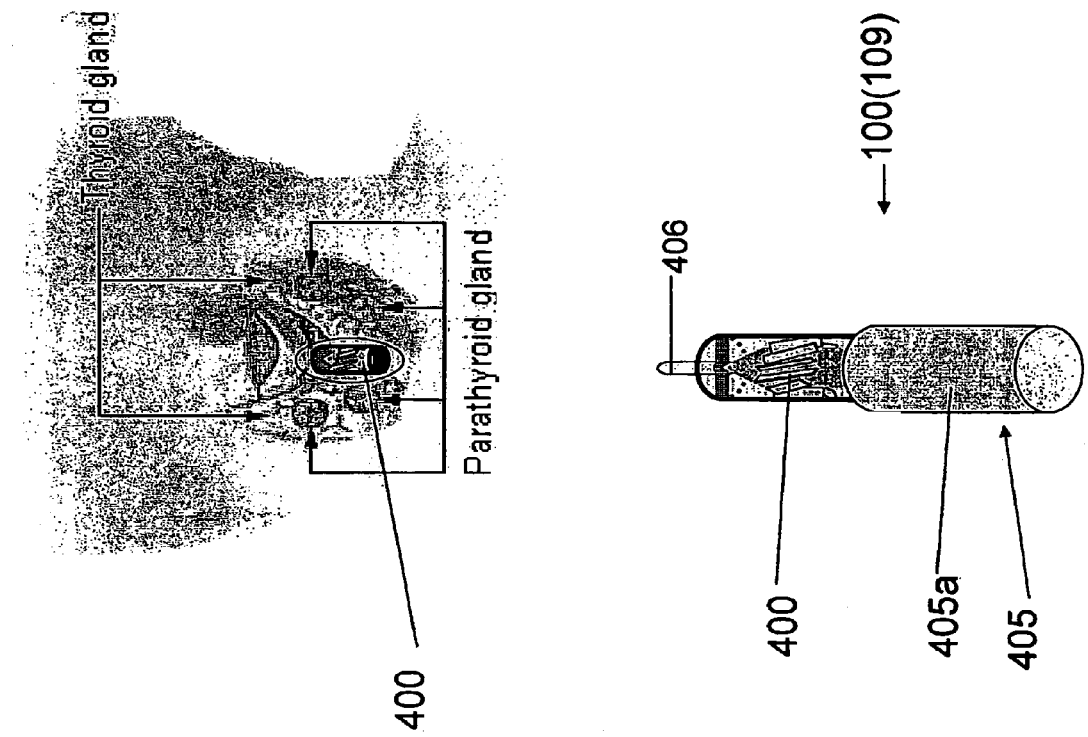
FIG. 36 is a modular magneto-mechanical device module having a reservoir and a port according to one embodiment of the invention.

With reference now to FIG. 36, glandular and other secretory organ disorders can affect the body's ability to properly regulate basic operational functions such as metabolism, digestion, autonomic reflexes and other hormonal or glandular regulated activities. In many cases said disorders are predicated as a result of overactive or under-active glandular secretions that are commonly treated with doctor prescribed medications. The use of 3MD technology offers an alternative to conventional drug treatments that often times have adverse side effects on the rest of the human body. 3MD modules 400 can be implanted in the secretory ducts or in the blood vessels directly adjacent to the duct portals of the affected glands to serve as secretory regulating devices. In addition, i-3MD regulating devices 104 configured with onboard chemical detectors can be used to precisely and interactively control the secretory regulation process. 3MD technology can also be used to treat and regulate sinus migraines and other similar sinus pressure-related ailments. A 3MD module 400 implanted in the sinus cavities can be used to regulate cranial, ocular, or facial sinus pressure by conveying mucus to the nasal passages for subsequent bodily expulsion. In such cases, the 3MD control assembly 500 can be integrated with external facial masks or the like for specific application during sinus pressure attacks.

With continued reference to FIG. 36, according to one embodiment of the invention, an implantable 3MD module 400 may be configured to contain one or more fluid reservoirs or conduits 405 such that the 3MD module 400 can be used for dispensing transportable media from the reservoir 405. Said fluid reservoirs 405 can be situated external to the body or implanted within the body and refilled through a self sealing membrane integrated with the reservoir vessel or container port 406. In this manner, the reservoirs 405 of the 3MD dispensing devices 109 can be easily and periodically refilled with the use of a simple hypodermic needle injection and without affecting the operation of the 3MD dispensing devices 109. In addition, 3MD dispensing devices 109 configured with 3MD onboard electrical power generation devices 103, wireless communication devices, and electrical fill status sensors can be used to signal the 3MD control assembly 500 when a dispenser reservoir 405 needs to be refilled. In the case of external reservoirs 405, the reservoir container or sac 405a can be made to be replaceable with the use of a quick disconnect conduit union. Alternatively, a 3MD module 400 can be used external to the body with an external reservoir 405 to perform the same internal dispensing functions just described but through external conduits passing into the body.

With continued reference to FIG. 36, 3MD dispensing devices 109 can also be used to precisely dispense medications to specific locations and/or organs within the body. In this manner, powerful medications such as the conventional chemotherapy treatments typically prescribed for cancer patients can be specifically targeted and dispensed in the effected locations thereby minimizing the strong adverse effects such drugs can have on the rest of the body. These medicinal dispensing techniques could also be used to treat neurological disorders, such as Alzheimers, in which medications to inhibit the formation of neuron clotting plaques known to be strongly associated with the disease can be precisely meted out to the brain by 3MD dispensing devices 109. Such 3MD dispensing devices 109 can also be used to medically treat and/or isolate other bodily infections and diseases.

Figure 37:
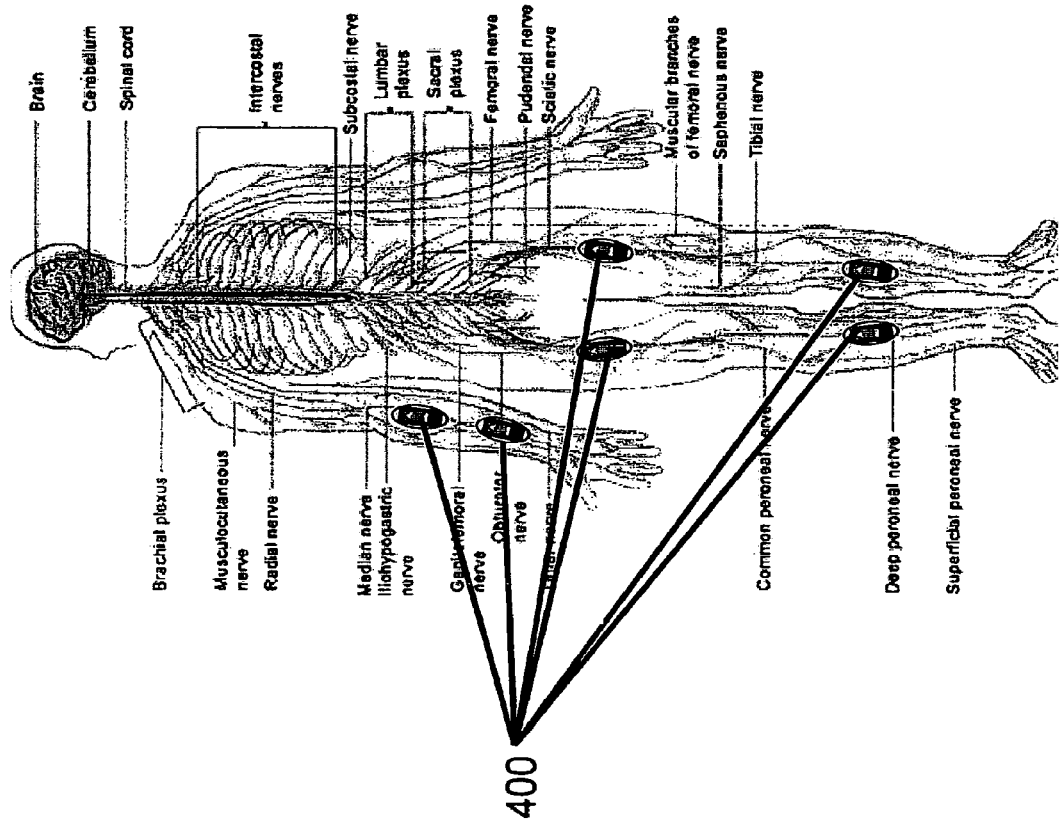
FIG. 37 is a plurality of modular magneto-mechanical device modules inserted into a human body according to one embodiment of the invention.
Figure 38:
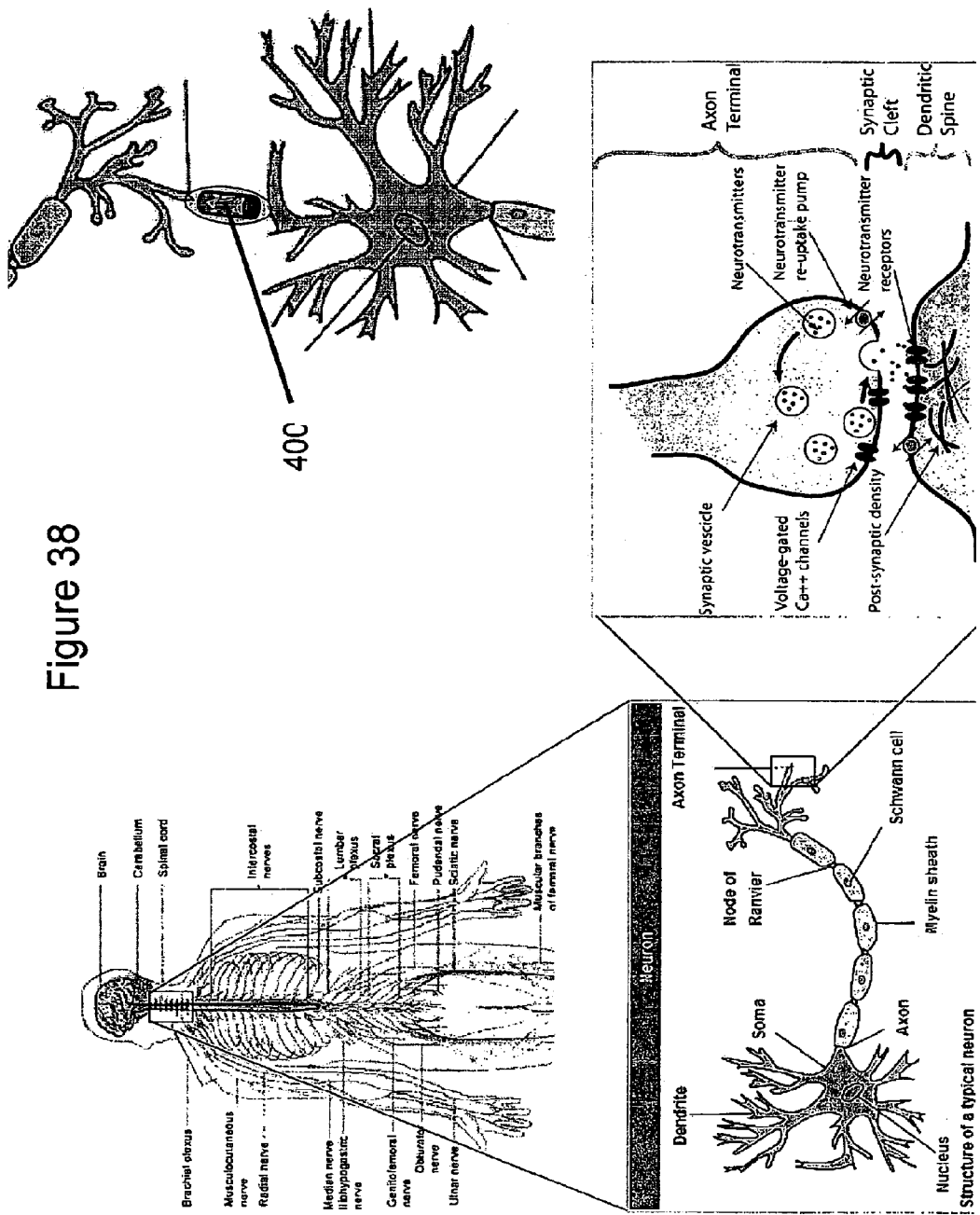
FIG. 38 is a modular magneto-mechanical device module according to one embodiment of the invention.

With reference now to FIGS. 37-38, an implanted 3MD module 400 configured with 3MD onboard electrical power generation device 103 can be used to provide electrical impulses through electrodes located near nerve cell endings in order to artificially simulate the electrical transmissions of neurons. In this manner, said 3MD stimulation devices 110 can be used to electrically stimulate neural activity thereby controllably inducing the activity of organs, tissues, and other internal biological operations within the human body 10. Said 3MD electrical stimulation functions can be integrated with any of the 3MD operations, functions, and applications previously and hereafter described.

With reference now to FIG. 36-38, with regard to bodily cosmetic appearance applications, 3MD technology can also be used to suppress the appearance of wrinkles in the skin. In such applications, 3MD dispensing devices 109 can be implanted near specific high visibility regions of the body such as the skin of the face or neck to dispense specific biochemicals to stimulate the elasticity and/or suppress degradation of elastin in the skin thereby reducing the appearance of wrinkles. In addition, 3MD technology can be used in specific regions of the human body where high concentrations of fat deposits may exist. In this manner, implanted 3MD dispensing devices 109 can be used to dispense artificially synthesized hormones such as insulin, glucagon and epinephrine directly into the adipose tissue or to artificially stimulate the production of said hormones in the targeted fatty region in order to metabolize the stored fat and thereby gradually reduce the appearance of visible fatty deposits in the human body. Alternatively, implanted 3MD stimulation devices 110 could be used to provide electrical impulses to simulate neuron activity to artificially induce the production of said hormones to metabolize the stored fatty deposits. As opposed to liposuction treatments that can be hazardous or conventional drug and dietary treatments that are often ineffective and can have adverse side effects on the rest of the body, 3MD dispensing/stimulation devices 109/110 can be specifically located in the bodily regions targeted for fatty deposit removal and can be used to stimulate and focus the body's own natural process to metabolize and break down unwanted adipose tissue.

With reference now to FIGS. 33, 36-38, with regard to glandular dysfunction and other related hormonal disorders, a network of 3MD dispensing/stimulation devices 109/110 could be used to controllably dispense or foster the production of any number of hormones, enzymes or hormone precursors throughout the body. For example, in the case of Parkinson's disease that is caused by the lack of the human hormone dopamine, 3MD technology can be used to dispense artificially synthesized dopamine into specific regions of the brain to combat the disease. Similarly, a network of 3MD dispensing devices 109 could be used to controllably dispense dopamine precursors or the other enzymes and coenzymes responsible for the production of dopamine in the body. Alternatively, an array of 3MD dispensing devices 109 could be used to artificially administer biochemical stimulants to specifically foster the natural production of the enzymes and coenzymes required for the natural biosynthesis of dopamine in the body. Likewise, implanted 3MD stimulation devices 110 could be used to provide electrical impulses to simulate neuron activity to artificially induce the production of said enzymes and coenzymes for the natural biosynthesis of dopamine. In this manner, an array of 3MD dispensing/stimulation devices 109/110 can be controlled by external controlling means and made to function as a biochemical regulatory network for the human body capable of precisely meting or stimulating the production of glandular biochemical fluid secretions into the blood stream, thereby regulating the basic operational bodily functions otherwise affected by glandular disorders and other hormonally related diseases.

With continued reference to FIGS. 33, 36-38, similarly, a network of implanted 3MD dispensing/stimulation devices 109/110 can be used to administer specific biochemical stimulants or electrical neural stimulation to the thymus, bone marrow, lymphoid tissues and other defense system organs to controllably foster the production of leukocytes, lymphocytes, antibodies and other immune system blood molecules used to defend and protect the body from infection. Together with the artificial immune system defined by the 3MD filtration device 106 applications previously described, said 3MD dispensing/stimulation devices 109/110 could be used to define a comprehensive and interactive 3MD artificial immune defense network capable of detecting, seeking, filtering, and/or destroying unwanted molecules, chemicals, and media in the blood while reinforcing the body's natural defenses by stimulating the production of the body's own defense system blood cells and biochemicals. Any of the above 3MD regulating, dispensing, and stimulation applications can also be implemented with other mammals and animals. Those skilled in the art will recognize that other conceivable 3MD applications not described herein may also be implemented with regard to any fluid regulation, dispensing, and stimulation operations.

Biomedical—Digestive System Applications

With reference now to FIGS. 31-32, gastroesophageal reflux disease (GERD) and dyspepsia are common digestive system disorders that plague millions of people worldwide and can lead to more serious afflictions such as esophageal cancer and stomach cancer. Implantable 3MD regulatory devices 123 can be used near the entrance of the stomach to prevent GERD and the abnormal reflux of gastric contents into the esophagus. In the case of dyspepsia and other related stomach disorders, 3MD devices configured for grinding and pulverizing operations can be used in the further physical breakdown of solid foods in order to facilitate the digestive process. In this manner, 3MD technology can be used to increase the surface area to volume ratio of the ingested solid food which facilitates and accelerates the digestive process and limits acid production during chemical breakdown thereby alleviating dyspepsia and minimizing the acid exposure otherwise witnessed by ulcers present in the stomach.

Figure 33:
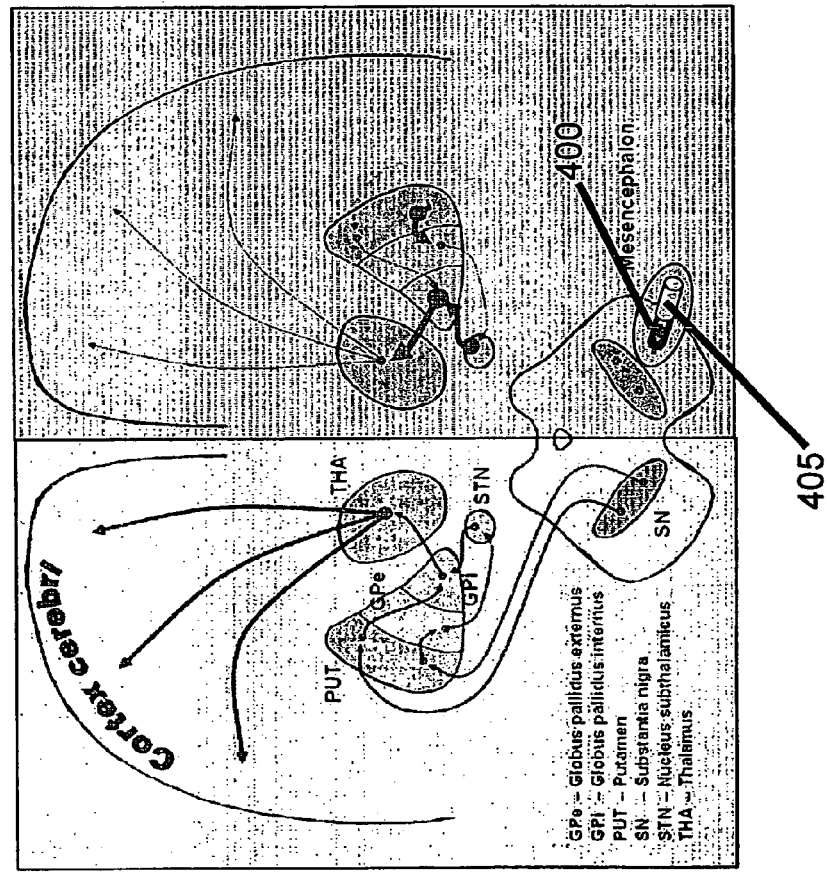
FIG. 33 is a modular magneto-mechanical device module according to one embodiment of the invention.

With continued reference to FIGS. 32-33, diverticulosis, inflammatory bowel disease, irritable bowel syndrome, constipation, and colorectal cancer are intestinal and colon disorders that can deter the reticular motions of the human intestinal tract thereby affecting the expulsion process of waste media from the human body. These disorders can often cause a significant amount of abdominal pain and are often chronic in nature, with some having no cure. In severe cases of colorectal cancer, the colon is removed and the patient must use a colostomy bag to collect the human feces that would have otherwise passed through the anus. In light of these disorders, 3MD conveying devices 111 can be used to controllably assist in the conveyance of semi-solid waste material through the human intestinal tract. In the case of a removed colon, a 3MD conveying device 111 can be made to serve as an artificial colon and/or anus that can be externally controlled to expel solid-like waste material from the human intestinal tract. Similarly, in the case of incontinence, a 3MD conveying device 111 can be made to serve as an artificial valve that can be externally controlled in order to release liquid waste from the bladder or solid waste from the human intestinal tract. Furthermore, 3MD dispensing devices 109 can be used to dispense biochemical lubricants into the intestinal tract or to stimulate the production of mucus secretions within the bowels in order to assist in the conveyance of transportable media through the intestinal tract. Alternatively, implanted 3MD devices 100 configured with 3MD onboard electrical power generation devices 103 could be used to provide electrical impulses to simulate neuron activity to artificially induce reticulation of the various intestinal and sphincter muscles of the gastrointestinal tract. In this manner, a network of 3MD dispensing/stimulation devices 109/110 could be used to controllably assist in the conveyance of media throughout the entire digestive tract.

Any of the above 3MD digestive system applications can also be implemented with other mammals and animals. Those skilled in the art will recognize that other conceivable 3MD applications not described herein may also be implemented with regard to any digestive system operations.

Biomedical—Reproductive System Applications

Figure 39:
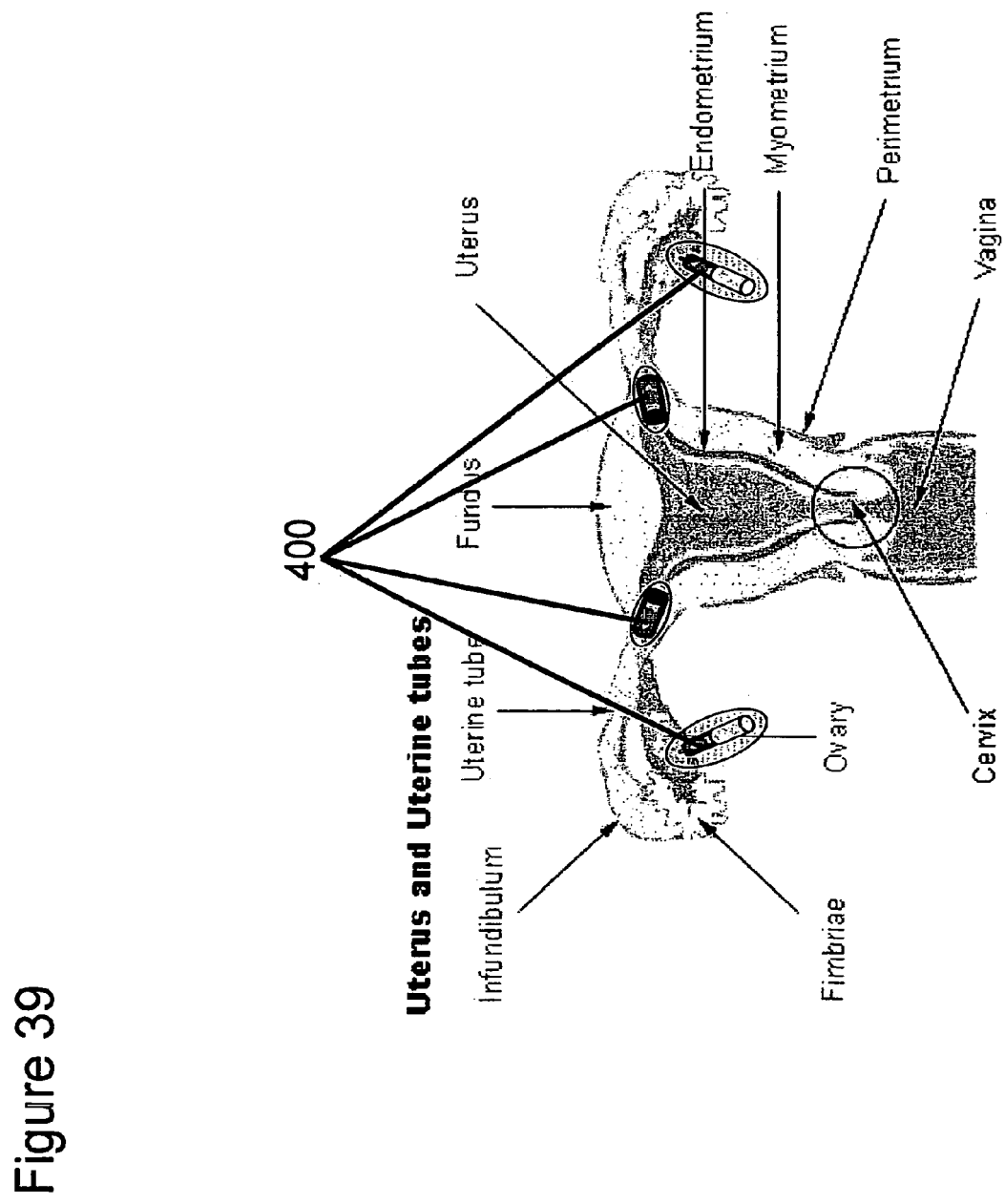
FIG. 39 is a modular magneto-mechanical device module according to one embodiment of the invention.
Figure 40:
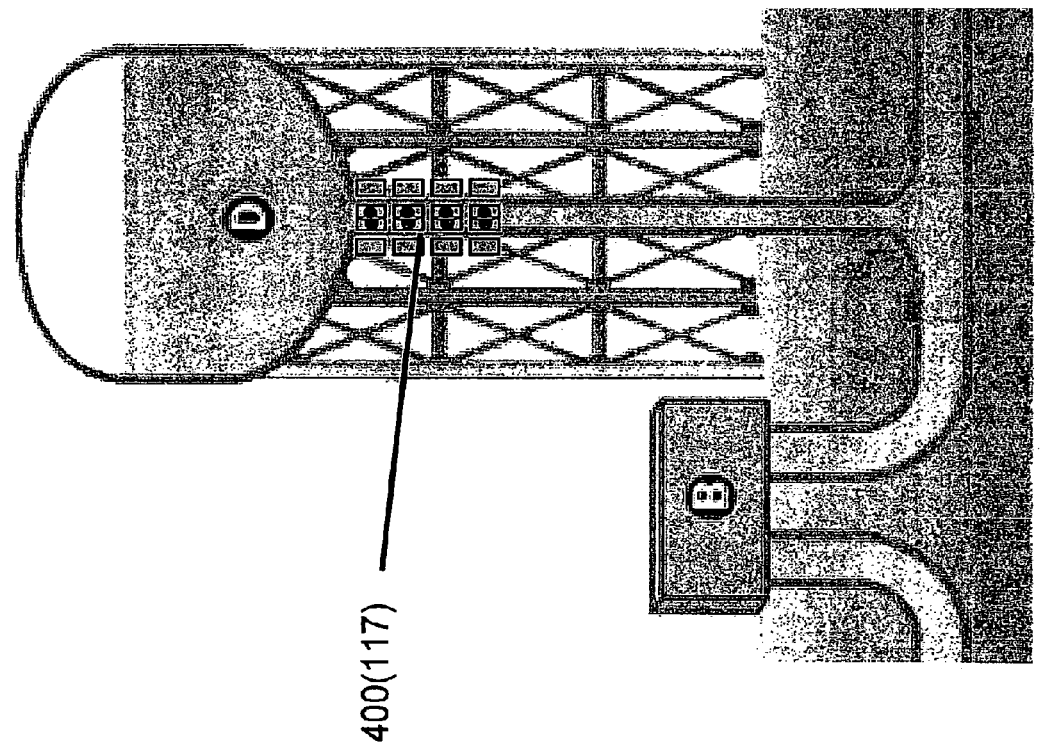
FIG. 40 is a modular magneto-mechanical device according to one embodiment of the invention.
Figure 41:
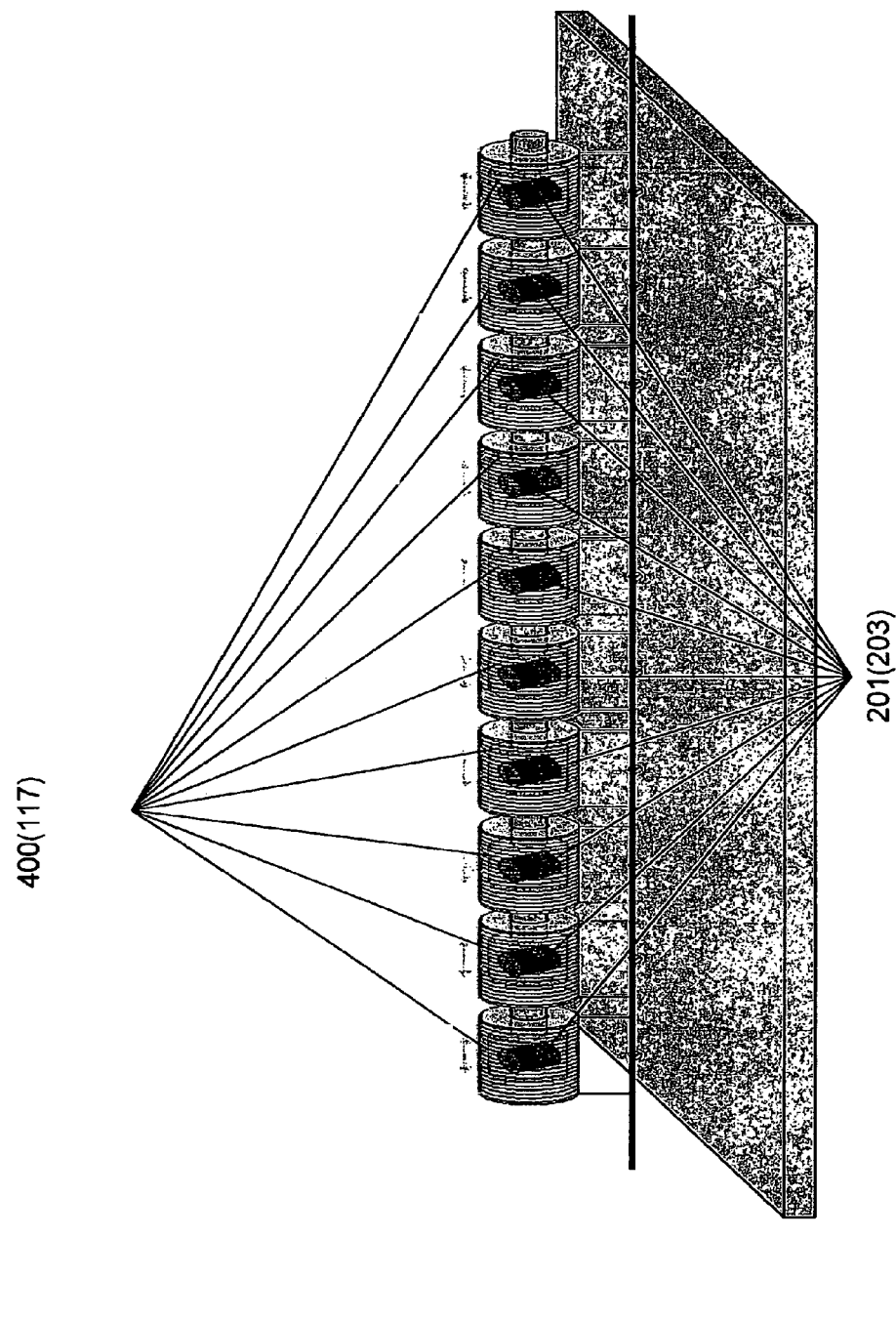
FIG. 41 is a plurality of modular magneto-mechanical devices functionally linked in series according to one embodiment of the invention.
Figure 42:
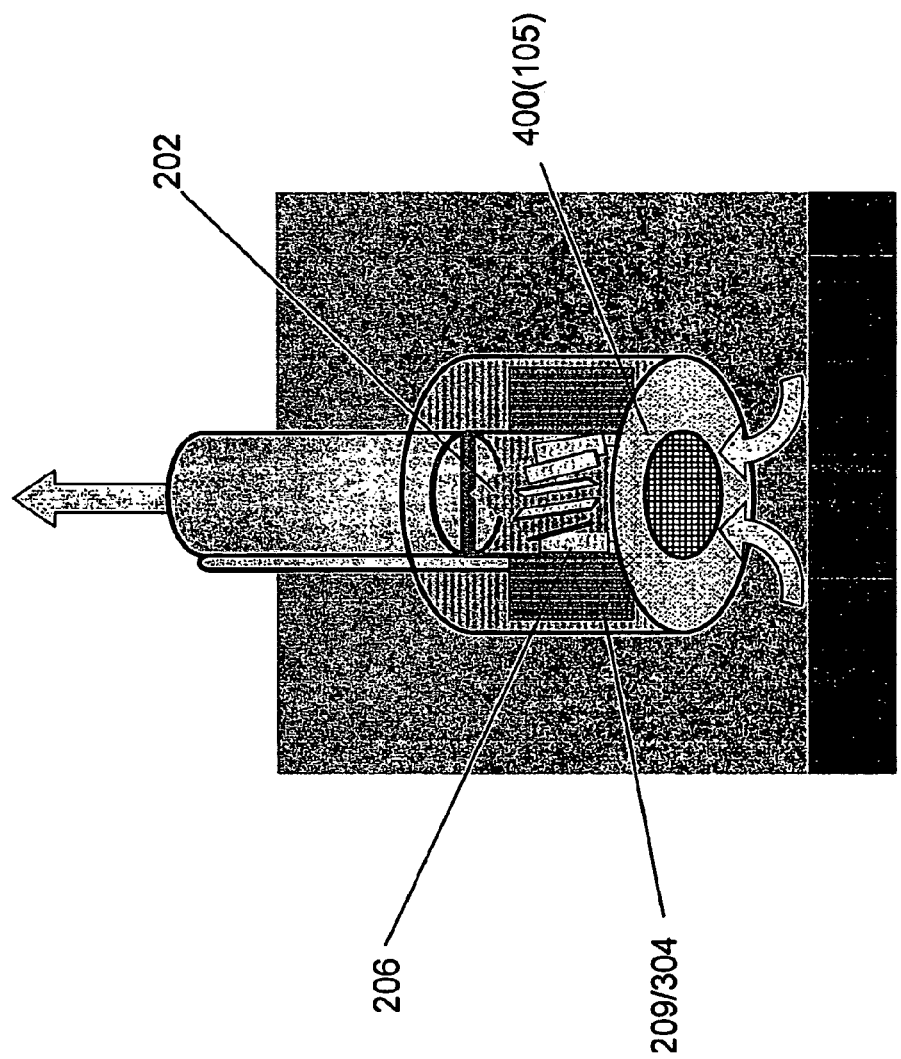
FIG. 42 is a modular magneto-mechanical device module according to one embodiment of the invention.
Figure 43:
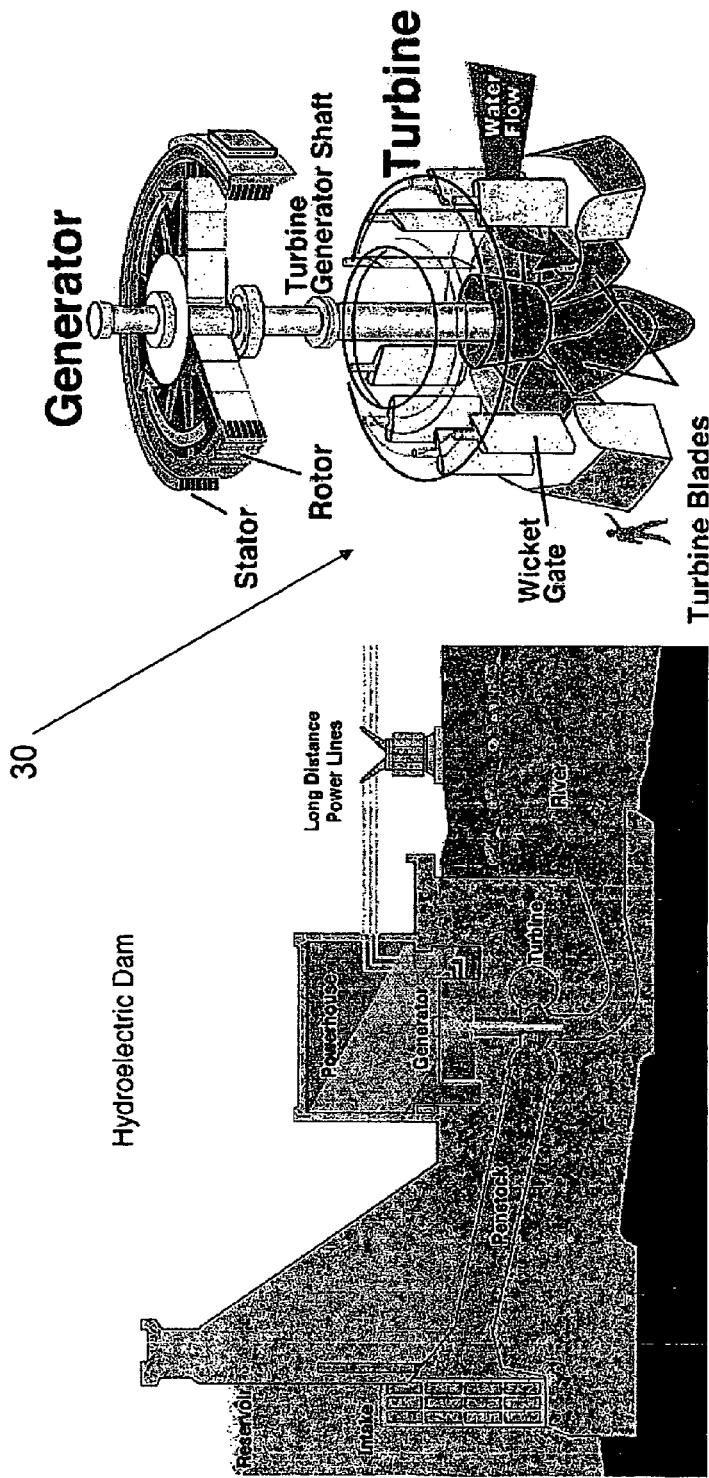
FIG. 43 is a prior art hydroelectric power generator turbine.

With reference now to FIG. 39, infertility, erectile dysfunction and other reproductive system disorders are medical conditions that affect millions of men and women worldwide. While medical treatments do exist for certain numbers of these disorders, said treatments are not always effective and can be very expensive with lengthy durations of treatment. In the case of female fertility drug treatments, for instances in which pregnancy actually does result, multiple embryos are often conceived as a result of overactive egg production due to drug stimulation. 3MD technology can be used to either assist or regulate female egg production. One or more 3MD conveying devices 111 can be implanted within a female patient's Fallopian tubes to either assist in or regulate egg delivery to the uterus. 3MD devices 100 can also be used to mete out specific biochemical fluids to affect the mucus layer surrounding the egg in order facilitate or regulate sperm penetration into the egg. As well, one or more 3MD dispensing/stimulation devices 109/110 can be implanted near the ovaries to mete out specific biochemicals or to provide electrical impulses to simulate neuron activity to either controllably stimulate or regulate egg expulsion to the Fallopian tubes. Additionally, 3MD conveying devices 111 can be used to position a fertilized egg within the uterus in order to controllably discourage anchoring of the placenta on or near the cervix which could otherwise result in complications during pregnancy. Similarly, 3MD modules 400 can be used as implantable devices in the male human body to controllably affect sperm conveyance, effusion, production, and potency. 3MD technology can also be used to specifically increase blood circulation to human genitalia to assist the effectiveness of the human reproductive process with regard to dysfunctional reproductive organ disorders associated therewith.

Any of the above 3MD conveying, regulating and dispensing applications can also be implemented in the reproductive systems of other mammals and animals. Those skilled in the art will recognize that other conceivable 3MD applications not described herein may also be implemented with regard to any reproductive system operations.

Biomedical—Microfluidic Process Applications

From an engineering perspective, the human body is comprised of a vast and profoundly complex system of biochemical reactions and processes that govern every thought, function, and operation performed by the human body. Although most of the chemical processes designed by engineers in the industrial world are conducted and operated on a macroscale, many of the biochemical processes governing human activity are conducted and operated on micro- and nanoscales. However, as with any chemical reaction or process operation, the mass transport of the reactive and/or reacted media is inherently required for initiation and progression of the operation regardless of scale. Since most of the biochemical reactions that take place in the human body typically occur in the fluid state, the mode of mass transport governing almost all human biochemical processes are inherently microfluidic in nature. Still, many of the microfluidic conveying devices described in the prior art have seen limited utilization in biomedical applications as a result of the fact that most of them employ a conventional electromechanical design and thus would require an implantable electrical power source and the direct integration of the electromagnetic field generation means with the movable conveying or pumping means.

3MD technology is well-suited for biomedical microfluidic applications since only the mechanical portion of the 3MD module 400 needs to be submersed within the microfluidic vessel, and hence only it needs to be miniaturized in order to accommodate microfluidic scaling applications. Although in principle all of the 3MD applications described heretofore have utility with regard to any number of biomedical processes and operations regardless of scale, they have involved systems and processes operating on the centimeter to micron scale whereas the following 3MD biomedical applications involve specific process operations orders of magnitude smaller in scale, at the sub-micron to nanometer level.

The human nervous system is a vast and complex network of nerve cells spanning the entire human body in which the spinal cord comprises the central pathway through which the brain communicates with the rest of nerve cell network. While at the present time the concept of artificial nerve cell replacement may be an impracticable one due to the billions of nerve cells and trillions of neuron connections present in the average human body, 3MD technology could be used to treat specific and isolated afflictions to the nervous system particularly with regard to spinal cord injuries. Depending on the location and severity of the spinal cord injury, certain nerve cell connections with the brain may be severed often resulting in the paralysis of certain portions of the human body. Although the nerve cells above and below the location of the spinal cord injury may remain intact, the severing of any nerve cells in the spinal cord cuts the critical neural connections controlling operations to the bodily regions affected with paralysis. Under these circumstances, microfluidic 3MD devices 112 could be used in the location of the spinal injury to artificially bridge the cut in the microfluidic neural conduit or to dispense certain genetically coded molecules, stem cells, proteins, neurotrophins, and/or other biochemical substances to artificially stimulate repair or re-growth of nerve cells and/or neural connections specifically targeted in the damaged nerve cell region. An array of such microfluidic 3MD devices 112 could be used to bridge several neural conduit breaches or to artificially stimulate the specific growth or repair of a bundle of individually severed nerve cells in order to create new neural connections or to re-establish neural connections with the intact mating portions of the severed nerve cells. Similar microfluidic 3MD conduit bridging and cell growth stimulation applications could be implemented in other damaged regions of the nervous system as in the case of brain injuries. Furthermore, 3MD cell growth stimulation technology could be used to stimulate the in-situ repair and recovery process of other damaged organs, tissues, or bones on a cellular level. Used in a converse manner, microfluidic 3MD technology could also be utilized to dispense, biochemical inhibitors to stifle cell growth or activity in specifically targeted regions of the human body, such as in the case of malignant tumors, cysts, or other cancerous anomalies and infections.

Microfluidic 3MD technology can also be used to control and/or affect specific cellular production within the human body. A microfluidic 3MD device 112 could be used to infuse, extract, or replace genetically coded molecules within the nucleus or cytoplasm of an individual cell in order to affect cell growth, reproduction, and/or utility. In this manner, microfluidic 3MD devices 112 can be used to replace the RNA and DNA of a given cell or group of cells in order to genetically engineer certain features of cell function and production. For example, with the use of an implantable microfluidic 3MD device 112 cells that carry one or more defective genetic traits can be reconfigured to carry DNA and RNA molecules with a genetically altered sequencing that does not carry the defective genetic characteristics. Similarly, microfluidic 3MD fluid devices 112 can also be used to replace the DNA and RNA of cells that have been genetically mutated.

Microfluidic 3MD devices 112 can also be used to controllably convey small volumes of biological fluids through micro- or nano-scale apertures and/or flow channels. Such microfluidic transport phenomena are applicable to flows on microchip sensors used for micro-scale biochemical reactors and biochemical detection and analysis for uses both internal and external the human body. For example, one or more microfluidic 3MD flow devices 112 can be used to convey dilute fluid solutions containing genetic biopolymers such as DNA and RNA through one or more flow contraction channels causing extensional stretch and orientation of the biopolymer molecules contained within, thereby facilitating individual nucleotide detection passing through each flow aperture for the purpose of genetic code sequencing.

Any of the above 3MD microfluidic process applications can also be applied for use with other mammals and animals. Those skilled in the art will recognize that other conceivable 3MD applications not described herein may also be implemented with regard to any biomedical microfluidic process operations.

Biomedical—Condition Monitoring and System Diagnostics

3MD devices 100 can also be configured to operate as external viscosity and rheology sensors for biological fluid condition monitoring. The electromagnetic force required to cause 3MD spindle 202 motion can either be precisely controlled for stress controlled rheological measurements or precisely measured for rate controlled rheological measurements. In this manner, fluid viscosity and rheology can be monitored as a function of applied deformation rate and/or applied stress in order to assess the physical condition of biological fluids such as saliva and mucus secretions. For example, a 3MD rheological sensor device 113 can be integrated with a thermometer device such that body temperature as well as the rheological behavior of a patient's saliva can be characterized in order to provide an assessment of human health or illness. Similarly, a 3MD rheological sensor device 113 can be integrated with a personal feminine product such that the rheological behavior of a patient's vaginal mucus can be characterized in order to provide an assessment of the patient's reproductive fertility cycle.

All of the 3MD biomedical applications involving detection, analysis, and sensing capabilities that were described previously can be integrated to define a comprehensive health monitoring network capable of performing online system diagnostics and responsive treatment within the human body. In this manner, the individual 3MD devices 100 comprising the entire 3MD workflow can be made to perform their respective sensing, detecting and analyzing functions as previously described and communicate their results to an integrated system controller capable of recognizing and reporting any system problems or stimuli detected in the network. Hence, an integrated 3MD workflow can be used to monitor the internal well being of a patient with the capability of detecting the earliest onset of infection, disorder, or anomaly throughout the human body. After analyzing and diagnosing the detected problem, specific 3MD devices within the workflow can then be controlled by the system controller and made to interactively treat or respond to the diagnosed problem as previously described. Thus, an integrated 3MD workflow can be a critical biomedical tool with regard to preventative health maintenance and fundamental human life support.

Any of the above 3MD condition monitoring and system diagnostics operations can also be applied for use with other mammals and animals. Those skilled in the art will recognize that other conceivable 3MD applications not described herein may also be implemented with regard to any biomedical condition monitoring or system diagnostics operations.

Biomedical—Surgical Applications

In addition to the number of biomedical applications involving internal medicine that have been described above, 3MD technology can also be used for a multitude of surgical applications from serving as tools to assist a surgeon in invasive surgical procedures or as implantable devices capable of performing in-situ surgical procedures within the human body. 3MD modules 400 can be configured to serve a multitude of surgical instrument operations that may include sawing, cutting, drilling, reaming, screwing, grinding, polishing, automated suturing, and vacuuming. As previously described, since 3MD modules 400 do not require the use of dynamic seals they do not run the risk of biohazardous contamination as do some conventional electromechanical and pneumatic surgical instrumentation. 3MD surgical modules 400 can also be configured as removable cartridges that may be collected and reused after proper sterilization or disposed of along with other biohazardous waste materials.

Any of the above 3MD surgical operations can also be applied for use with other mammals and animals. Those skilled in the art will recognize that other conceivable 3MD applications not described herein may also be implemented with regard to any surgical instrument applications.

Biomedical—Artificial Prosthesis and Muscle Applications

3MD technology can also be incorporated into the design of artificial external and implantable prostheses. In this manner, 3MD modules 400 can be integrated into artificial bones, joints, teeth, tissue, eyes, limbs, and other body parts and tasked to perform any number of functions and operations as previously described. For example, a 3MD module 400 can be incorporated into the design of artificial spinal vertebrae and tasked to assist in the neural transmission of electrical impulses to, from, or along the spinal cord. In another illustrative example, a 3MD module 400 can incorporated into the design of an artificial femur or humerus and tasked to generate electrical power for neural stimulation of adjacent muscle tissue and/or to assist in artificial bone marrow operations in powering an onboard bioreactor for the synthetic production of human blood cells or any other vital biological cells and fluids required in the body.

3MD technology can also be used to provide artificial motor or muscle functions to the human body. Implantable 3MD modules 400 can be configured for use as electromechanical actuation devices to assist or replace muscular function in human limbs, appendages, and other parts of the body. Said implantable 3MD actuation devices 114 can be connected to existing or artificial connective tissue of the human body to drive linear and/or convoluted motions used in the controlled flexion of joints for motility of the adjoining limb or appendage. Similarly, said 3MD actuation devices 114 can be integrated with existing or artificial joints such that controlled rotational actuations can be used to directly drive and control joint flexure. Alternatively, 3MD pumping devices 105 can be used for hydraulic actuations in fluid-driven artificial muscle tissue applications. Furthermore, 3MD actuation device control assemblies 500 can be configured to respond to adjacent motor neuron activity for closed loop feedback motion control of artificial muscle operation. Similarly, said 3MD actuation devices 114 can also be used external to the body as actuation devices to assist or simulate normal muscle operation.

Said 3MD prosthesis applications can also be applied for use with other mammals and animals. Those skilled in the art will recognize that other conceivable 3MD applications not described herein may also be implemented with regard to any artificial prosthesis applications.

Energy—Power Generation and Energy Recovery Applications

With reference now to FIGS. 40-46, in addition to the number of applications that have been previously described, 3MD technology can also be used in a multitude of electrical power generation applications. 3MD modules 400 can be configured as turbine generators for wind and hydroelectric power generation applications. Unlike conventional turbine generator modules 30, 3MD technology offers significant performance advantages with regard to seal-free operation and lower generator inertia and friction losses. Furthermore, the 3MD generator induction coils 403 can be configured as permanent hermetically sealed components while the movable 3MD turbine modules 400 can be configured as easily replaceable generator cartridges. For example, 3MD turbine modules 400 can be utilized as replaceable turbine generator cartridges that can operate without the need for high-pressure dynamic seals in hydroelectric power generation applications involving large scale hydroelectric dams. In addition to conventional hydroelectric power generation applications, a multitude of 3MD turbine modules 400 can also be used for lake, sea, and oceanic hydroelectric power generation applications. In this manner arrays of replaceable 3MD turbine modules 400 can be used to comprise hydroelectric "farms" for coastal and/or off-shore applications thereby harnessing the abundant source of mechanical energy present in large bodies of water in the form of tidal motions, surface waves, and other water currents and flows. Thus, 3MD hydroelectric turbine generator networks 115 can be strategically positioned along coastal waterways or water traffic zones and/or in high flow or rapid water current regions in order to maximize hydroelectric power output. Said 3MD turbine power generator technology also offers the luxury that it can be designed to operate below the water's surface so as not to detract from the appearance of the environment. Similarly smaller 3MD turbine modules 400 and arrays can also be used for portable onboard hydroelectric power generation applications for use on off-shore platforms as well as marine and naval vessels. Under such circumstances retractable "strands" of portable 3MD hydroelectric turbine generator modules 400 can be dragged or placed overboard on boats and ships for local onboard electric power generation. Similar modules or arrays of 3MD turbine generators can also be used on boats and ships for local onboard wind power generation.

With reference now to FIGS. 25, 41-46, although hydroelectric projects have provided an abundant source of electrical power generation for communities around the world, wind power generation has experienced far more limited success due in part to the lack of public acceptance because of the unsightly impact that conventional wind turbine generator technology can have on the environmental landscape. In addition to turbine generator applications, 3MD technology can also be used to convert flexure and reticulating motions driven by wind energy into linear actuations for electrical power generation. For example as illustrated in FIG. 25, a multitude of miniature 3MD linear motion power generators attached on a long, thin, flexural compliant beam member or substrate can be used to generate electrical power when beam flexure is driven by the force of air flowing over the beam's surface causing the movable magnetic elements of the 3MD linear generator modules 400 to move within the enveloping 3MD conductive coils 403 thereby inducing electrical currents with each beam flexure and reticulation driven by wind force of the gentlest of breezes. In this manner arrays of 3MD flexible beam power generator devices 116 can be used to comprise the leaves and/or branches of a wind power generator fashioned in the design of an artificial plant, bush, or tree. Thus, a network of 3MD flexible beam wind power generator devices 116 could be fashioned as a cluster, grove, or forest of artificial plants, bushes, or trees capable of supplying electrical power to a dwelling, building, or community while not detracting from the appearance of the environment. These wind power generator devices 116 can be fashioned to match or complement the flora and fauna of a given geographical environment, for instance in the case of coastal or tropical regions said 3MD networks could be fashioned in the design of palm tree groves or forests. Hence a multitude of such 3MD wind power generator artificial forests can be used to generate electrical power in poor, remote or isolated regions where electrical power utilities are often expensive or inaccessible. This 3MD technology also offers the capability of stealth applications such that said 3MD wind power generator devices 116 can be designed to blend in to a given locale or environment where covert operations may need to be performed. In a further application of this technology, 3MD flexible beam power generator devices 116 can be used to comprise arrays of flexible beam or artificial plant generator devices 116 located alongside highly trafficked roadways where the strong wind currents generated from passing vehicles could be used to produce electrical power or integrated with textiles and fabrics such that flags, banners, streamers and the like that would otherwise serve only in a decorative capacity could also be used to produce electricity by harnessing the kinetic energy of the flapping motions driven by the forces of the wind.

Similarly, arrays of 3MD flexible beam power generator devices 116 can be used to comprise clusters of flexible breakwater barriers, channel buoys, channel marker lines, water flaps, artificial reeds, or other artificial water plants and flora in order to harness the energy of water tides, flows and currents in the form of hydroelectric power generation. Said 3MD technology can also be coupled with other 3MD hydroelectric power generation devices 115 previously described in order to fully harness the abundant kinetic energy available in large bodies of water.

In a further development, 3MD flexible beam power generator devices 116 integrated with textiles and fabrics can be utilized in clothes, shoes, and other garments where the kinetic energy from human motions and movements can be converted into electrical energy to power small personal electronic or other such electrically powered devices. In yet another embodiment, 3MD flexible beam power generator devices 116 can be integrated with carpeting, flooring, subflooring, walkways, sidewalks, and roadways where the abundant kinetic energy from pedestrian and vehicular traffic can be harnessed and converted into electrical energy to power any number of power storage or electrical devices.

In addition to power generation applications involving the harnessing of power of naturally occurring flows and processes, 3MD technology can also be used to recover energy from man made systems and operations. In a manner similar to the applications just described, 3MD turbine power generators 117 can be used in any process flow stream to convert the flow of transportable media into electrical power generation in order to recover some of the energy utilized in a given process or operation. For example, a 3MD turbine power generator module 400 can be used in a water tower to convert the flow of water exiting the water tank or reservoir into hydroelectric power. In this manner, some of the energy usurped in pumping the water up to the water tower can be recovered with the use of a replaceable 3MD turbine power module 400 that requires no dynamic seals and can operate with very low frictional losses and no loss in water head pressure. Hence, the power generated with 3MD generator modules 400 can be restored to the water pumping process or utilized in a different operation or function. In a similar fashion, 3MD turbine power modules 400 can be used in any number of industrial processes or operations involving the flow or recirculation of transportable media to recover some of the energy used in conveying said media. Likewise, 3MD power generator modules 400 can be utilized in flow collection and waste water drainage conduits such that the gravity fed flows passing through the drainage pipes and plumbing networks can actually be used to generate electrical power. The use of said devices could be particularly beneficial in the case of large buildings and factories where such drainage flows are almost continuous. Furthermore, said 3MD power generator devices 103 strategically located within a drainage network can also be configured to serve in a dual role by operating in an active pumping mode to provide positive pressure driven flow to, assist in the removal of drain blockages and flow restrictions.

With reference now to FIG. 27, direct drive 3MD power generator modules 400 can be used to recover energy from the motion of any mechanical assemblies, equipment or machinery with applications representing almost limitless energy recovery possibilities. By fastening the movable magnetic element(s) 401 of the 3MD to a movable drive assembly, motion of said drive assembly causes motion of the associated magnetic field within the enveloping 3MD conductor coil 209 thereby inducing an electrical current within the 3MD power generator device 103. In this manner, detachable 3MD power generator modules 400 can be attached to the moving or rotating shaft of any motor, engine, equipment, apparatus, or machinery such that the kinetic energy from said devices can be used to recover some of the power required to drive said devices with no mechanical or frictional losses associated therewith, thereby improving the overall power consumption and efficiency of said devices.

With reference now to FIG. 26, 3MD technology can also be used in other non-conventional power generation applications where the kinetic energy from a process or flow stream can be converted into electrical power. For instance, 3MD turbine power generator modules 400 can be used in thermally driven recirculation flow loops, as depicted in FIG. 26. In such cases, thermal energy supplied to the heating zone of a recirculation loop can cause a density gradient within a given fluid or fluidic compound system used for driving a buoyant fluid flow within the loop which in turn can propel the rotors of one or more 3MD turbine generators 117 thereby generating electrical power. As the thermally energized fluid circulates around the loop it cools, losing its buoyancy, ready to be re-energized upon reentry into the heating zone. In this manner, self contained, hermetically sealed fluid recirculation loops driven by thermal gradients and containing one or more 3MD turbine generator modules 400 can be used to produce electrical power in environments having limited power generation alternatives. The thermal energy source for said 3MD thermodynamic recirculation loops can be driven by solar energy collectors or similar heat transfer conduits from integrated heat exchanger devices from a variety of naturally occurring or man-made energy streams. Said self contained 3MD thermodynamic recirculation loop devices 118 can be used in any combination of terrestrial, marine, or celestial environments. The thermal density transitions of the fluid contained within said devices can be optimized with regard to seasonal variations and/or the normal temperature gradients indigenous to the geographical region of installation.

Any of the above 3MD power generation applications can also be applied for use with any multitude of gas, fluid, or fluid-like flows, kinematics and operations involving the conversion or recovery of kinetic or thermal energy. Those skilled in the art will recognize that other conceivable 3MD power generation applications not described herein may also be implemented with regard to the conversion and recovery of kinetic and thermal energy into electrical power.

Chemical, Food & Pharmaceutical—Manufacturing and Production Applications

In addition to all of the applications just described, 3MD technology can be used for a multitude of manufacturing applications such as for production operations in the chemical, food, and pharmaceutical industries. Chemical, gas, petroleum, polymer, food, beverage, and pharmaceutical manufacturing requires the use of contamination-free processing and conveying devices, however because many of these manufacturing operations are carried out under high pressures over a very wide range of temperatures much of the conventional processing equipment require the use of dynamic motor or pumping seals that may become contaminated with production line changeovers and may potentially leak thereby affecting production and/or posing serious risks in terms of hazards and damage to human health and the environment. Such leakage risks may be potentially fatal and/or environmentally devastating when said processes involve the manufacture and handling of flammable, explosive, hazardous, and/or toxic materials.

Although magnetic coupling driven pump devices are presently used for seal-free industrial pumping applications, said devices require the use of a separate drive motor in addition to an electromagnetic coupling in order to operate the pump assembly. While 3MD modules 400 can also operate without the need for dynamic motor or pumping seals, they don't require the use of a separate drive motor and can be configured as modular replaceable/interchangeable cartridges of any shape or size that can be easily inserted within pipes, conduits, or processing lines and disposed of or easily removed for subsequent cleaning, de-contamination, sterilization and reuse. In this manner, 3MD modules 400 can be configured to perform one or a multitude of functional operations as previously described which may include pumping, conveying, recirculation, dispensing, regulating, filtering, separating, agitating, and mixing applications involving solids, liquids, and gases that are inherently required in the manufacture of chemicals, gases, pharmaceuticals, polymers, foods, beverages, and petroleum based products. Because they can be configured for any size or shape application, 3MD modules 400 can be used for any scale manufacturing and production line operation from microfluidic to large scale processes regardless of processing environment, pressure or temperature. Furthermore, the electrical 3MD control assembly 500 can be hermetically sealed from the processing stream environment and easily mounted on the outside wall of the vessel, container, pipe, or conduit in order to wirelessly control the operation of the 3MD module 400 contained therein. In addition, since they employ a wireless and brushless mode of motor technology, 3MD devices 100 inherently do not generate the electrical sparks typically produced with conventional motor technology, and hence they do not run the risk of igniting an explosion in the event of a leak in a processing line containing flammable or explosive materials. And, since 3MD devices 100 don't require the use of separate drive motors or couplings for functional operation, 3MD devices 100 can inherently operate with lower inertia, friction and mechanical losses thereby minimizing the power consumption associated therewith. In addition, because the moving elements of a 3MD device 100 can be wholly contained within the production line vessel, container, pipe, or conduit, 3MD devices 100 can be operated more silently than conventional production line equipment, thereby minimizing the harmful noise levels that are typically inherent in manufacturing and production environments. Any number of 3MD devices 100 can be operated and controlled independently or as an integrated network system defining a 3MD workflow capable of performing a multitude of operations and functions in the manufacturing process line.

3MD devices 100 can be particularly useful in production and manufacturing operations involving corrosive, caustic, erosive, or abrasive transportable media. Conventional pumping, conveying, mixing, and separating devices used with such media commonly exhibit premature and excessive wear and must be frequently replaced, often at significant production expense and downtime. Although 3MD modules 400 may exhibit similar wear cycles, they could be manufactured and replaced at a fraction of the expense and time of conventional processing equipment. For example, highly abrasive slurries are often generated in the petroleum industry during secondary and tertiary oil well recovery as well as in bitumen recovery from tar sand deposits. As an alternative to the frequent and costly replacement of the processing equipment used to convey these highly caustic and erosive slurries, a network of 3MD pumping and conveying devices 105, 111 employing staged pumping principles can be utilized as replaceable pump cartridges controllably regulating flow directly inline to the petroleum pipeline production stream.

Mobile 3MD devices 119 can be used to work with blockages or restrictions in the manufacturing production line. In this manner, mobile 3MD devices 119 can be inserted into the production line conduit, controllably made to travel to a specific location within the network of vessels and conduits, and used to perform one or a multitude of functional operations such as pumping, conveying, or diverting flow through or around the flow restriction or removing, dissipating, breaking apart, grinding, honing, or pulverizing accumulated wall residue, restrictions, and blockages present in the production line. Hence, restrictions and blockages in the production flow stream can be accommodated for, circumvented, removed or dramatically reduced in size with the use of mobile 3MD modules 400 strategically located throughout the flow network thus minimizing and/or negating their adverse effect on the rest of the manufacturing production line.

When operated in a passive mode, 3MD modules 400 can also be used as in-situ flow meters within a gas, fluid, or fluid-like manufacturing process line. By actively monitoring 3MD spindle 202 motion and/or induced current generation as the 3MD spindle 202 mechanically responds to the process line flow stream passing through the 3MD module 400, volumetric flow rate can be precisely determined by the external 3MD device control assembly 500. In this manner, said 3MD devices 100 can be used to actively monitor flow rates locally within the process line and responsively regulate the process flow stream accordingly throughout the 3MD flow network during the manufacturing process.

3MD devices 100 can also be configured to operate as online viscosity and rheology sensors for a fluid or semi-fluid manufacturing process line. The electromagnetic force required to cause 3MD spindle 202 motion can either be precisely controlled for stress controlled rheological measurements or precisely measured for rate controlled rheological measurements. In this manner, fluid viscosity and rheology can be continually or periodically monitored as a function of applied deformation rate and/or applied stress in-situ to the manufacturing flow stream in order to assess fluid physical condition, the extent of reaction of a given reactive process operation, and/or the state of mixing of a given mixing operation. With 3MD modules 400 also configured to generate onboard electricity, 3MD rheology sensor devices 113 can also be integrated with any number of wireless communication devices, electrical sensors, chemical analyzers and other such analytical sensing devices for the purposes of providing a more comprehensive material analysis for in-situ assessment of chemical and physical material condition and/or the state of mixing or reaction.

3MD technology can also be utilized in any number of post-production operations such as in the handling and dispensing of liquids, gases, and solid particles and powders. Again, because chemical, gas, petroleum, polymer, food, beverage, and drug handling and dispensing must involve contamination-free operations, 3MD modules 400 can be configured as modular conveying and dispensing cartridges that can be inserted within pipes, conduits, vessels, valves, or container lids and can be easily removed for disposal or subsequent cleaning, de-contamination, or sterilization. As well, the 3MD control assembly 500 can be hermetically sealed from the handling and dispensing stream environment, can be easily mounted on the outside wall of where the 3MD module 400 is contained, and is permanently reusable to wirelessly control the operation of any number of 3MD handling and dispensing modules 400.

Any of the above 3MD manufacturing, production, and post-production applications can also be applied for use with any multitude of manufacturing operations and industries. Those skilled in the art will recognize that other conceivable 3MD applications not described herein may also be implemented with regard to any chemical, food, and pharmaceutical manufacturing, production, or post-production operations.

Agricultural and Dairy Applications

In addition to the chemical and food industry applications just described, 3MD technology can also be utilized in a multitude of agricultural and dairy applications. With regard to specific farming processes, animal waste streams, fertilizers, pesticides, herbicides, organic slurries, and other agricultural chemicals represent potentially hazardous and/or toxic exposure risks to human contact and the environment. Because 3MD modules 400 do not require dynamic seals, potentially hazardous leaks and spills can be prevented in said processes with the use of 3MD pumping and conveying devices 105, 111 that can be configured as easily removable/interchangeable cartridges that can be disposed of or cleaned for reuse. Conversely, 3MD modules 400 can also be used in contamination-free dairy applications as interchangeable cartridges that can be disposed of or easily removed and subsequently sterilized for reuse. In this manner 3MD devices 100 can be used for the handling, dispensing, conveying, pumping, homogenizing, or separating of agricultural and dairy products and byproducts. Those skilled in the art will recognize that other conceivable 3MD applications not described herein may also be implemented with regard to any agricultural and dairy related operations.

INDUSTRIAL APPLICATIONS

In addition to the manufacturing, processing, production, and post-production operation applications described earlier, 3MD technology can be used for a number of other industrial applications. Similar to the pumping and conveying applications previously described, 3MD modules 400 can be configured as removable modular cartridges of any shape or size that can be easily inserted into hoses, pipes, or conduits for the pumping and conveying of water, powder, chemicals, solid and fluid suspensions, slurries, oil, and other hydraulic fluids.

With regard to deep well/hole fluid and water extraction applications that are inaccessible with conventional vacuum or suction pumping equipment, one or more 3MD modules 400 can be configured to operate in series or in parallel within a flexible line, hose, or conduit of any shape or size for use in the pumping of fluids from the farthest depths of a deep well/hole back up to the earth's surface. The 3MD control assembly 500 for said applications can be positioned external to the wall of said conduits such that it is shockproof or entirely hermetically sealed and protected from said fluid environments. In this manner one or more portable 3MD-equipped fluid extraction lines can be supplied with electrical power, attached end-to-end, and used in a staged pumping configuration in order to pump water and other fluids from extremely deep locations with otherwise limited accessibility. Multiple 3MD-equipped fluid extraction lines could also be attached to extract water in emergency situations where flooding has occurred. Similar shockproof 3MD devices 120 can also be operated on a permanent or semi-permanent basis while fully submersed in a fluid making them ideally suited for sump pump-type applications specifically designed for flood prevention.

Said 3MD-equipped extraction devices 121 can also be used in the handling, extraction, recovery, and remediation of hazardous and/or toxic media. In this manner, portable 3MD-equipped extraction devices 121 can be used to handle, pump, and convey hazardous and/or toxic media from a remediation site, cesspool, septic tank, or similar hazardous material reservoir. The 3MD modules 400 utilized in such applications can be configured to be removable for subsequent disposal, replacement, or reuse.

As previously described, similar 3MD pumping devices 105 can also be utilized as inserted cartridges in legacy pipes, conduits, and plumbing installations where internal blockages or flow restrictions are inaccessible or in which the pipe conduits may not be conducible to conventional chemical or mechanical blockage removal techniques. In this manner, a replaceable 3MD pumping device cartridge can be easily inserted immediately below a drain entrance in order to provide a pressure assisted flow during drainage that would otherwise be encumbered by the presence of a downstream flow restriction. A network of 3MD pumping devices 105 strategically positioned throughout a plumbing installation can also be used to divert flows or to controllably agitate and/or circulate pressure driven flows in order to assist in the removal of blockages and flow restrictions. Similarly, said 3MD devices 100 can also be used in supply flow conduits and configured to controllably regulate the pressure and flow from one or more flow outlets in order to boost outlet pressure, increase flow rate, or to eliminate pressure fluctuations during flow.

3MD modules 400 can also be configured to operate with fluidic sprayers. In this manner, inherently seal-free 3MD pumping devices 105 can be used to safely convey potentially hazardous and/or toxic chemicals from a reservoir for subsequent spraying broadcast to a specified target. Alternatively, 3MD modules 400 can also be configured to operate within the conduit directly preceding the fluid broadcast.

Because 3MD modules 400 can be utilized in any fluid or gas environment regardless of operating temperature or pressure, 3MD technology can also be used in cryogenic or superheated transportable media applications. Similar to the manner previously described, 3MD devices 100 can be configured as replaceable cartridges 407 for insertion within any sized or shaped fluid conduit to handle, pump, convey, or perform any number of functional operations involving superheated steam and gases as well as cryogenic fluids.

Figure 47:
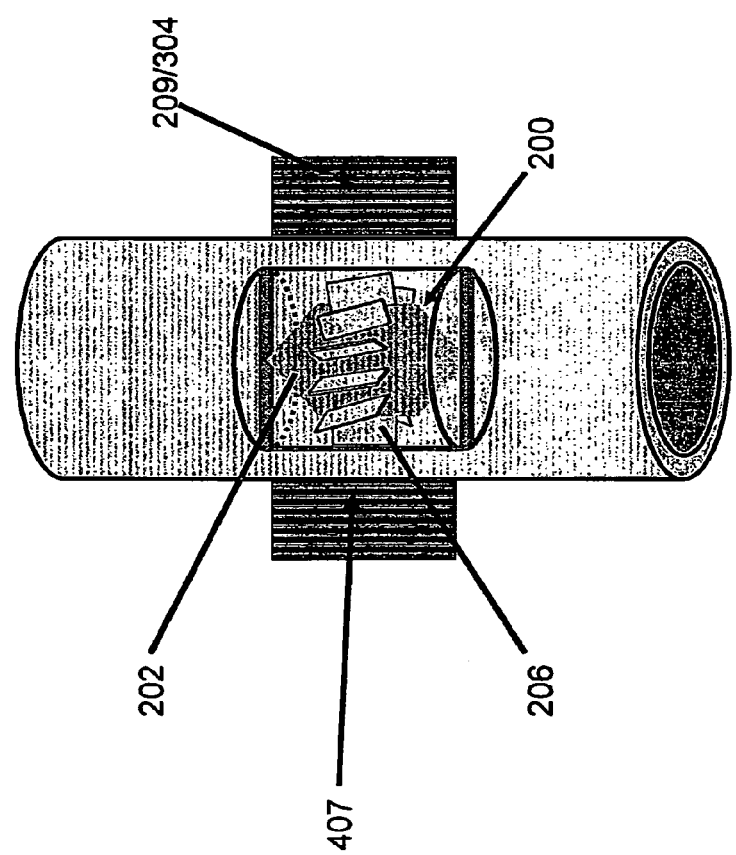
FIG. 47 is a perspective view of a modular magneto-mechanical device module that comprises a modular/interchangeable cartridge according to one embodiment of the invention.

With reference now to FIG. 47, a 3MD module can also be configured as a detachable magnetic sleeve containing one or more permanent magnet elements that can be attached to any beam member or shaft of a given piece of industrial machinery capable of rotation and/or linear motion. By enveloping the detachable 3MD sleeve with one or more electromagnetic coils, the magnetic field generated by the electromagnet coil(s) and a controllable electrical current source may be used to either attract or repel the respective magnetic poles of the magnetic sleeve, thereby driving motion of the magnetic sleeve and the beam member attached therein. In this manner, said detachable 3MD magnetic sleeve device can be used as a portable, quick-disconnect brushless motor device capable of being utilized in temporary, supplemental or emergency situations as required in an industrial environment and with the benefit of no further frictional contribution or losses associated therewith to the moving shaft assembly. Those skilled in the art will recognize that other conceivable 3MD applications not described herein may also be implemented with regard to any industrial processes and operations.

Laboratory and Clean Room Applications

In addition to all of the applications involving unregulated environmental conditions, 3MD technology can also be utilized in laboratory and clean room applications where environmental parameters are often precisely regulated. As previously described, 3MD modules 400 can be configured to perform any number of functional operations required in a laboratory, and unlike conventional pumping, conveying, and dispensing devices used in most laboratories, 3MD modules 400 can operate seal-free thereby eliminating the risks associated with contamination and leakage. Said 3MD modules 400 can also be configured to be removable cartridges that can be scaled to operate in microfluidic or larger pilot scale applications and easily disposed of or reused depending on the utility and the quantity of material specimens passing through each laboratory operation. This removable 3MD cartridge utility is particularly useful in laboratory and clean room applications where post contamination remediation is often costly requiring the complete replacement of equipment and instrument assemblies as a result of said contamination. For instance, whereas conventional positive pressure pumps, vacuum pumps, mixers, and agitators are often quite difficult to decontaminate and/or sterilize after the repeated process stream changeovers that are inherent with laboratory scale operations, 3MD pumping, mixing, and agitating cartridges 407 can be easily removed, sterilized and reused, or discarded. And, because these cartridges 407 can be utilized for any transportable media regardless of temperature or pressure, 3MD technology can be used in a multitude of laboratory applications ranging from the cryogenic to the superheated or from vacuum to hyper pressure. Those skilled in the art will recognize that other conceivable 3MD applications not described herein may also be implemented with regard to any laboratory and clean room operations.

HVAC Applications

Figure 44:
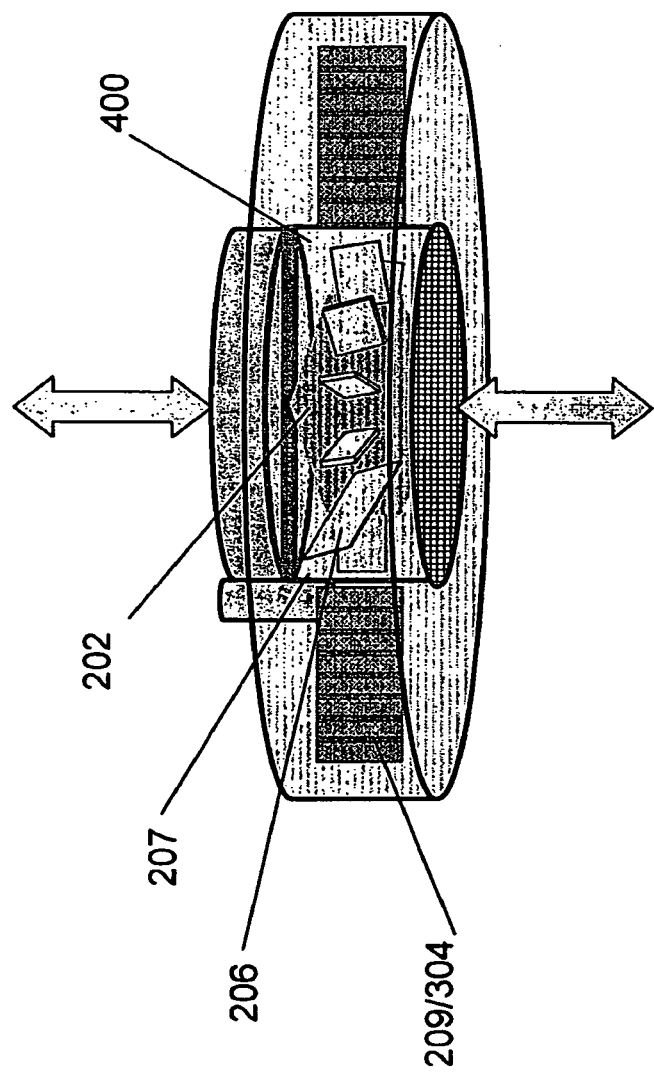
FIG. 44 is a modular magneto-mechanical device module according to one embodiment of the invention.
Figure 45:
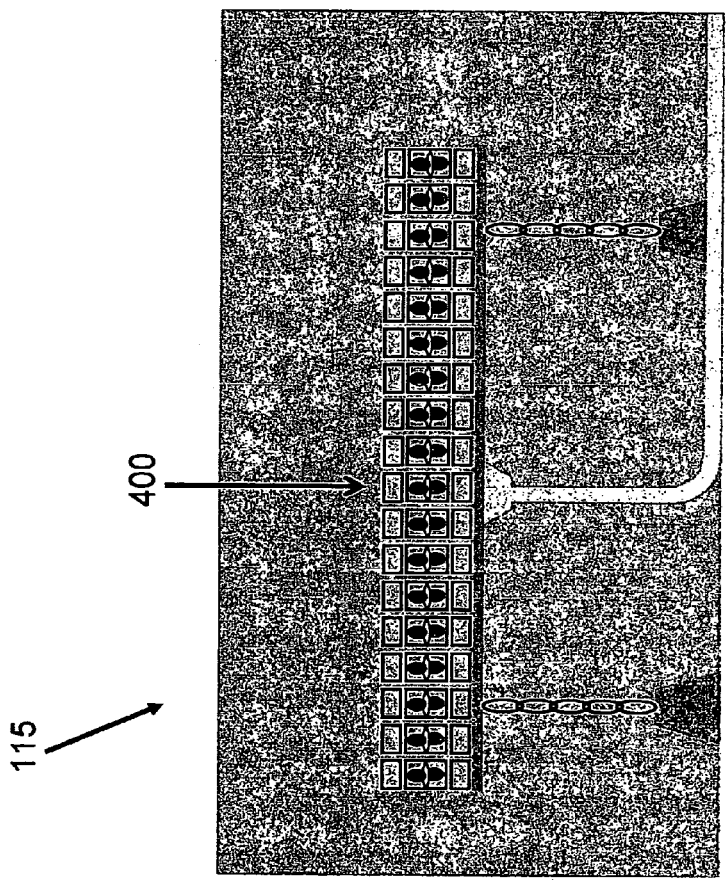
FIG. 45 is a perspective view of an array of modular magneto-mechanical device modules that may be used for hydroelectric power generation according to one embodiment of the invention.
Figure 46:
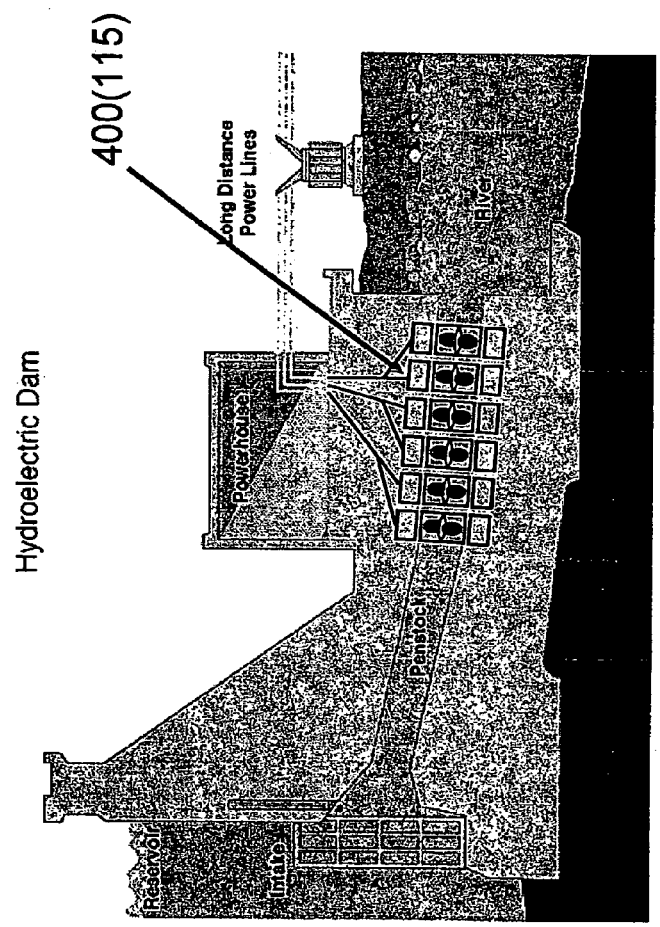
FIG. 46 is a perspective view of an array of modular magneto-mechanical device modules that may be used for hydroelectric power generation according to one embodiment of the invention.

With reference now to FIG. 44, 3MD technology can also be utilized in heating, ventilation, and air conditioning (HVAC) applications where operational efficiency and cleanliness often comes at a premium. Because they can operate at very low inertia and noise levels, can be easily inserted into existing ductwork, and can be easily removed for subsequent cleaning, 3MD modules 400 are well-suited for air blower, circulation and ventilation applications. Furthermore, the 3MD's control assembly 500 and other electrical components are hermetically sealed from the dust, dirt, and soot that typically collects and flows in ventilation ductwork and which often plagues the operation and durability of conventional blower motors and actuators used in HVAC applications. As well, because it does not require a drive motor, drive belt, or other mechanical couplings, a low-profile, ultra-thin 3MD circulator/impeller module 400 can be used in confined spaces and other HVAC applications where low-profiles may be warranted. In addition, since it can be inserted within conduits of various size and shape, 3MD modules can be used in small diameter tubes, pipes, and conduits that are frequently utilized to retrofit older dwellings and buildings that have no pre-existing ductwork for central air conditioning and heating. Moreover, individual 3MD circulator modules 400 inserted near the exit of each circulation conduit/vent can be used to individually control the air flow from each vent. An array of said 3MD circulator vent modules 400 equipped with wireless communication devices and operating independently or in collaboration with one another can then be used to comprise an integrated 3MD airflow network that can be controlled wirelessly from one or more centralized locations.

In addition to blower and ventilator applications, 3MD technology can also be incorporated for use in refrigeration and boiler systems. Unlike conventional air conditioning refrigeration pump equipment that always run the risk of refrigerant leakage and environmental exposure hazards, 3MD pump modules 400 can operate seal-free regardless of temperature hermetically sealed from the external environment. Similarly, these hermetically sealed 3MD pump modules 400 can be used to circulate heated water or fluids to and from boilers for radiant heating applications. Those skilled in the art will recognize that other conceivable 3MD applications not described herein may also be implemented with regard to any HVAC operations.

Electronics Applications

Figure 48:
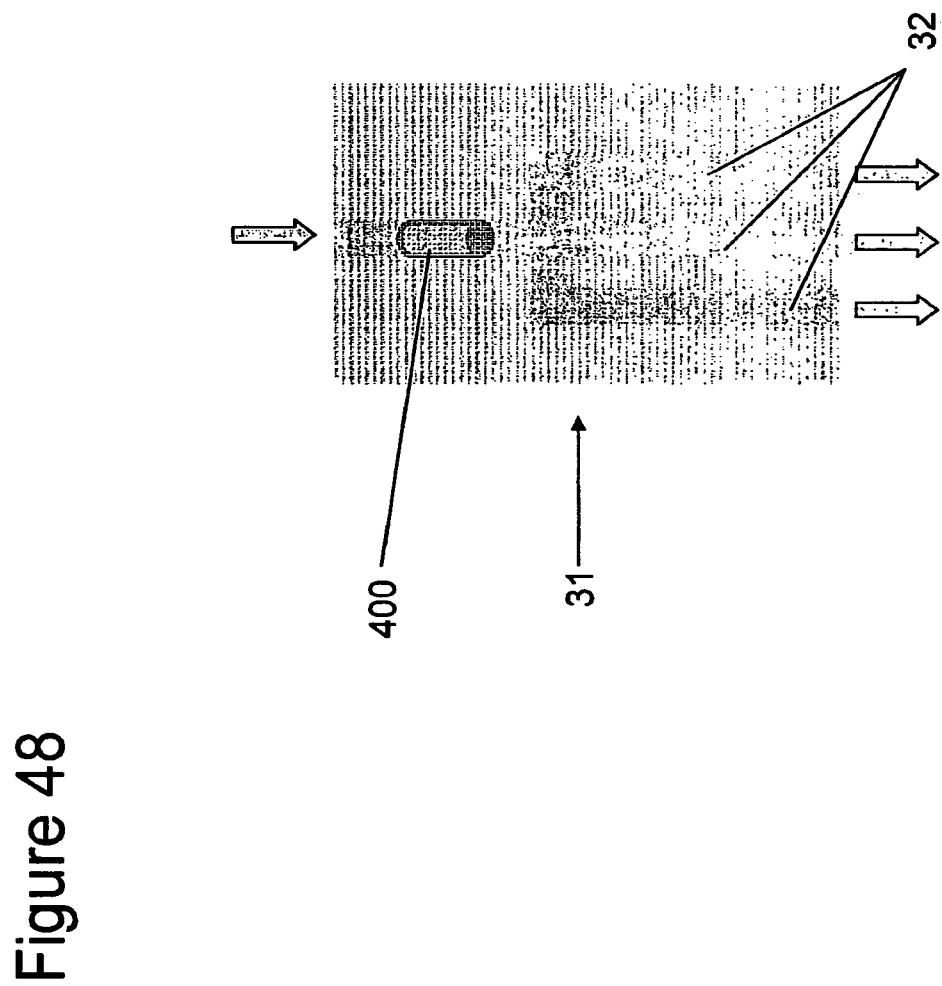
FIG. 48 is a perspective view of a modular magneto-mechanical device module integrated with an electronic microchip equipped with microfluidic flow channels according to one embodiment of the invention.
Figure 49:
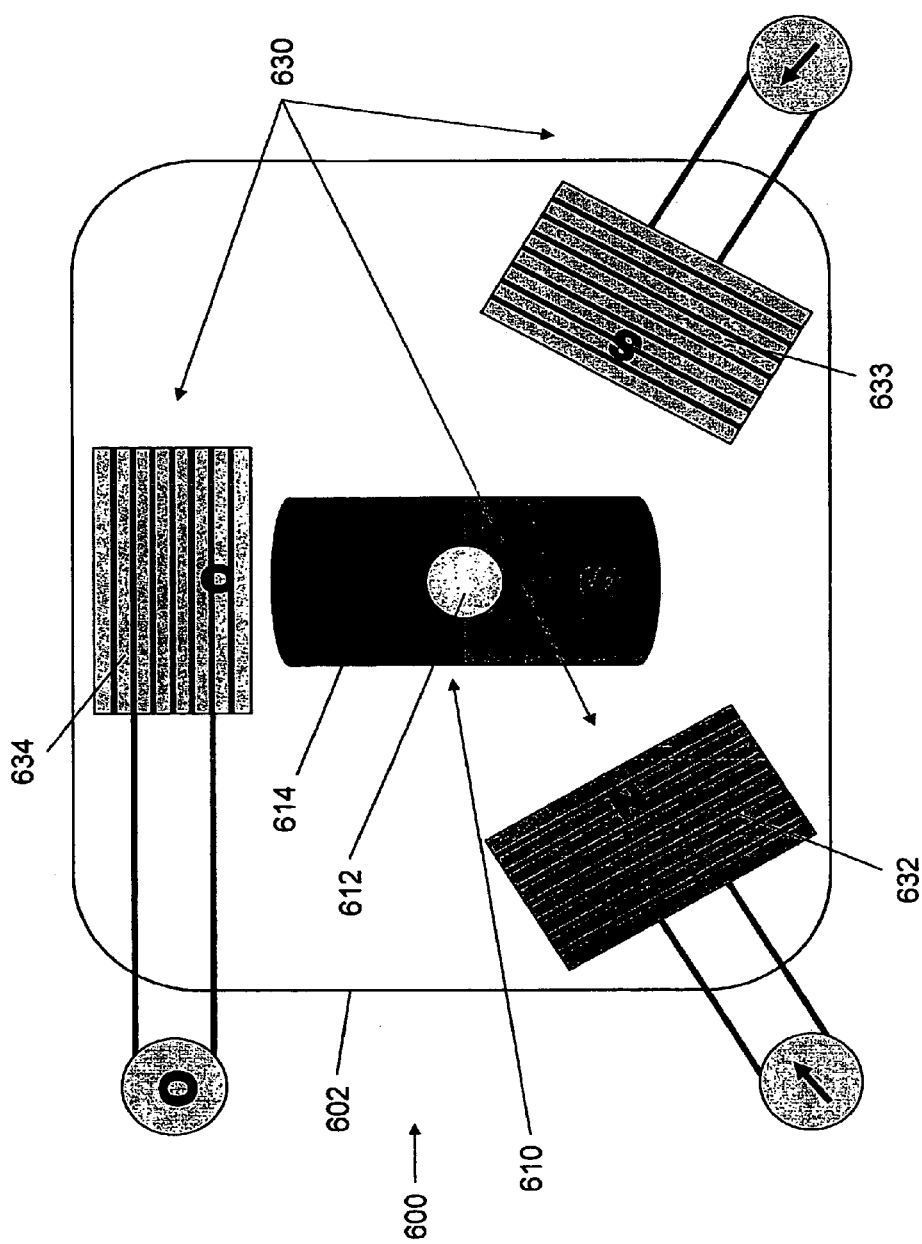
FIG. 49 is a perspective view of a prior art brushless motor.

With reference now to FIG. 48, as described previously, 3MD technology can be used for a multitude of functions and operations across a broad spectrum of industries, including those involving electronics applications. In addition to all of the 3MD wireless motor module operations that can be conceivably implemented with regard to electronic product and component applications, the microfluidic pumping and conveying capabilities offered by 3MD technology present unique opportunities in the field of electronics. Although most electronic microchips and components are air cooled, fluids naturally provide better heat transfer properties which would serve to reduce the heat build-up and thereby improve the efficiency of electronic circuitry. As described earlier, an array of microfluidic 3MD pump modules 400 can be integrated with electronic microchips and components 31 equipped with microfluidic flow channels 32 in order to pump cooling fluid through the 3MD workflow and dramatically improve the heat transfer from the electronic circuitry. Microfluidic 3MD pumping, conveying, and mixing devices can also be used on microchip reactors and sensors to control and regulate the flow and interaction of media at microfluidic and microscopic levels. These microfluidic 3MD devices 112 can also be used to control and regulate the flow of microfluidic media in biological computers. Those skilled in the art will recognize that other conceivable 3MD applications not described herein may also be implemented with regard to any electronics operations.

Consumer Goods Applications

In addition to the numerous applications already described, 3MD technology can also be used for a multitude of consumer goods applications. In general, 3MD devices 100 can be utilized for any disposable or reusable consumer product application or operation that requires or could potentially benefit from wireless motor technology. For instance, removable 3MD turbine modules 400 configured as disposable or reusable cartridges 407 can be used in portable or centralized vacuum cleaning systems where dirt and dust residue often deteriorates the electrical components of conventional vacuum motors. Similarly, because the 3MD control assembly 500 can be hermetically sealed from any potentially wet, harsh, or hazardous environment, 3MD pump modules 400 can be used in a multitude of consumer goods and appliance applications including but not limited to water jet and recirculation sources for hot tubs and swimming pools, washing machines, dishwashers, as well as pumping/conveying sources for water and beverage dispensers, chemical and paint sprayers, water and confectionery fountains, power washers and other fluid pumps, dispensers and sprayers. 3MD turbine modules 400 can also be used as blowers for hair dryers, portable heaters, fans and air pumps. Furthermore, as previously described, 3MD modules 400 can be configured to operate as refrigeration pumps for portable air conditioning units, dehumidifiers, refrigerators, freezers, refrigerated vending machines, and other refrigeration products and appliances.

As described earlier, direct drive 3MD power generator modules 400 can be incorporated into the design of any number of motorized consumer goods or appliances in order to recover some of the power required to drive said devices with no mechanical or frictional losses associated therewith, thereby improving the overall power consumption and efficiency of said devices. Those skilled in the art will recognize that other conceivable 3MD applications not described herein may also be implemented with regard to any consumer goods products.

Automotive, Marine, and Aerospace Applications

In addition to the many applications described previously, 3MD technology can also be used for a multitude of automotive, marine, and aerospace applications. 3MD modules 400 can be configured to operate in a number of functional roles and vehicular operations that include but are not limited to fuel pumps, fuel injectors, oil pumps, water pumps and dispensers, chemical pumps, fuel injectors, power steering pumps, hydraulic fluid system pumps and actuators, fluid dispensers, refrigeration pumps, as well as waste pumps for onboard toilets and lavatories.

3MD turbine modules 400 can also be used as propulsion devices for automotive, marine and aerospace applications of any size, shape or scale. In this manner, 3MD propulsion modules 400 can be configured to operate seal-free without the need for a separate drive motor or engine from an electrical power source hermetically sealed from said water and/or air environments. Said 3MD propulsion devices 122 can be incorporated for use in a number of transportation related applications that include but are not limited to air-propelled automobiles, road vehicles, off-road vehicles, hovercraft, ice runners/gliders, airplanes, blimps, air gliders, balloons, unmanned aircrafts, as well as water-propelled boats, ships, submarines, amphibious vehicles, recreational water vehicles, underwater auto propulsion units for swimmers and divers, and other forms of watercraft.

Similar to what has been described previously, 3MD technology can also be utilized for power generation in a multitude of automotive, marine, and aerospace applications to recover energy from the motion or rotation of any related mechanical components and assemblies. In this manner direct drive 3MD power generator modules 400 can be incorporated for use on rotating engine shafts, drive/transmission shafts, axle shafts or wheel assemblies in order to recover some of the power required to drive said devices with no mechanical or frictional losses associated therewith, thereby improving the overall power consumption and efficiency of said devices. Such 3MD power generator modules would be particularly useful in power generation applications involving non-driven wheel assemblies on 2-wheel drive vehicles and tractor trailers that would otherwise only function in a vehicular braking and stability capacity. 3MD flexible beam power generators 117 can also be used to recover the kinetic energy from the inherent motion of vehicular components such as in the flexure of air foils, wings, suspension assemblies, tires, and mud flaps that would otherwise provide no contribution to vehicular energy recovery. Those skilled in the art will recognize that other conceivable 3MD applications not described herein may also be implemented with regard to any automotive, marine, and aerospace operations and processes.

Various embodiments have been described, hereinabove. It will be apparent to those skilled in the art that the above methods and apparatuses may incorporate changes and modification without departing from the general scope of this invention. It is intended to include all such modifications and alterations in so far as they come within the scope of the appended claims or equivalents thereof.

Having described the invention, it is now claimed:

1. A method for moving a transportable medium, comprising:
    providing an electromechanical device comprising a rotor, a stator, and a module that at least partially houses the rotor; wherein during operation of the electromechanical device, the module is contained within a conduit or vessel and the stator is positioned external to and separate from the conduit or vessel, and wherein operation of the electromechanical device moves a transportable medium.

2. The method of claim 1, wherein the electromechanical device is a brushless electric motor, and wherein the rotor comprises a first magnet and the stator comprises a second magnet; and wherein the device comprises a control assembly for use in controlling the motion of the rotor by controlling polarity of the second magnet.

3. The method of claim 2, wherein the rotor comprises a first permanent magnet and the stator comprises a second electromagnet.

4. The method of claim 2, wherein the rotor comprises a first electromagnet.

5. The method of claim 2, wherein the control assembly controls orientation of the second magnet with respect to the first magnet.

6. The method of claim 2, wherein the device further comprises a conductive coil, wherein motion of the rotor induces an electric current in the conductive coil.

7. The method of claim 1, wherein the electromechanical device is an electromotive device and wherein the rotor comprises a first magnet and the stator comprises a first electromagnetic induction coil, and wherein during operation of the electromotive device motion of the rotor induces a current in the first electromagnetic induction coil.

8. The method of claim 7, wherein the rotor comprises a first permanent magnet.

9. The method of claim 2, wherein the module comprises a first conduit for passage of a transportable media through the module for contact with the rotor.

10. The method of claim 9, wherein motion of the rotor at least partially assists in passage of the transportable media through the first conduit.

11. The method of claim 9, wherein the module further comprises an adjustable aperture for use in controlling flow of the transportable media through the first conduit.

12. The method of claim 11, wherein motion of the rotor at least partially controls opening and closing of the adjustable aperture.

13. The method of claim 9 wherein the rotor further comprises a spindle comprising:
    (a) a magnet receiving portion that at least partially receives the first magnet;
    (b) a shaft about which the rotor rotates with respect to the module; and,
    (c) a second conduit for passage of the transportable media through the module for contact with the rotor, wherein the second conduit and the first conduit define a coaxial portal.

14. The method according to claim 1, wherein the module is suitable for implantation into a conduit or vessel in a human body.

15. The method according to claim 1, wherein movement of the transportable medium permits sensing or measuring viscosity or rheology of the medium as it passes through the module.

16. The method according to claim 1, wherein the transportable medium is a gas or a liquid.

17. The method according to claim 16, wherein movement of the transportable medium achieves power generation.

18. The method according to claim 16, wherein the transportable medium is blood.

* * * * *